United States Patent
Lynch et al.

(10) Patent No.: US 7,638,637 B2
(45) Date of Patent: Dec. 29, 2009

(54) ORALLY AVAILABLE SPHINGOSINE 1-PHOSPHATE RECEPTOR AGONISTS AND ANTAGONISTS

(75) Inventors: Kevin R. Lynch, Charlottesville, VA (US); Timothy L. Macdonald, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 233 days.

(21) Appl. No.: 10/578,216

(22) PCT Filed: Nov. 3, 2004

(86) PCT No.: PCT/US2004/036563

§ 371 (c)(1), (2), (4) Date: May 3, 2006

(87) PCT Pub. No.: WO2005/041899

PCT Pub. Date: May 12, 2005

(65) Prior Publication Data

US 2007/0088002 A1 Apr. 19, 2007

Related U.S. Application Data

(60) Provisional application No. 60/516,887, filed on Nov. 3, 2003.

(51) Int. Cl.
C07D 233/61 (2006.01)
C07D 277/22 (2006.01)
C07D 263/32 (2006.01)
A61K 31/4164 (2006.01)
A61K 31/421 (2006.01)
A61K 31/426 (2006.01)

(52) U.S. Cl. .................... 548/340.1; 548/205; 548/235; 548/335.1; 514/365; 514/374; 514/396

(58) Field of Classification Search ............... 548/340.1
See application file for complete search history.

(56) References Cited

U.S. PATENT DOCUMENTS

| | | | |
|---|---|---|---|
| 3,153,092 A | 10/1964 | Burger | |
| 4,939,130 A | 7/1990 | Jaeggi et al. | |
| 5,405,988 A | 4/1995 | Klar et al. | |
| 5,773,475 A | 6/1998 | Kohn | |
| 6,069,251 A | 5/2000 | Thurkauf et al. | |
| 6,875,757 B2 | 4/2005 | Miller et al. | |
| 7,060,697 B2 | 6/2006 | Marsilje et al. | |
| 7,064,217 B2 | 6/2006 | Macdonald et al. | |
| 7,241,790 B2 | 7/2007 | Lynch et al. | |
| 2004/0224941 A1 | 11/2004 | Seko et al. | |
| 2005/0032744 A1 | 2/2005 | Michaelis et al. | |
| 2005/0043386 A1 | 2/2005 | Nishi et al. | |
| 2005/0107447 A1 | 5/2005 | Lynch et al. | |
| 2006/0046979 A1 | 3/2006 | Foster et al. | |
| 2006/0122181 A1 | 6/2006 | Ikemoto et al. | |
| 2006/0135786 A1 | 6/2006 | Saha et al. | |
| 2006/0211656 A1 | 9/2006 | Albert et al. | |
| 2006/0223866 A1 | 10/2006 | Evindar et al. | |
| 2007/0088002 A1 | 4/2007 | Lynch et al. | |
| 2007/0191313 A1 | 8/2007 | Beard et al. | |

FOREIGN PATENT DOCUMENTS

| | | |
|---|---|---|
| EP | 1 553 091 A1 | 7/2005 |
| EP | 1602660 A1 | 12/2005 |
| GB | 950388 | 2/1964 |
| JP | 06135935 | 5/1994 |
| JP | 06135936 | 5/1994 |
| JP | 2002-316985 | 10/2002 |
| JP | 2004 307442 | 4/2004 |
| WO | WO 99/35259 | 7/1999 |
| WO | WO 01/60819 A1 | 8/2001 |
| WO | WO 02/064616 A2 | 8/2002 |
| WO | WO 02/076995 A2 | 10/2002 |
| WO | WO 02/092068 A1 | 11/2002 |
| WO | WO 03/059880 A1 | 7/2003 |
| WO | WO 03/061567 A2 | 7/2003 |

(Continued)

OTHER PUBLICATIONS

International Search Report for PCT/US2004/036563.

(Continued)

*Primary Examiner*—Kamal A Saeed
*Assistant Examiner*—Shawquia Young
(74) *Attorney, Agent, or Firm*—Prout International IP, LLC

(57) ABSTRACT

The present invention relates to S1P analogs that have activity as S1P receptor modulating agents and the use of such compounds to treat diseases associated with inappropriate S1P receptor activity. The compounds have the general structure (I) wherein $R_{11}$ is $C_5$-$C_{18}$ alkyl or $C_5$-$C_{18}$ alkenyl; Q is selected from the group consisting of $C_3$-$C_6$ optionally substituted cycloalkyl, $C_3$-$C_6$ optionally substituted heterocyclic, $C_3$-$C_6$ optionally substituted aryl $C_3$-$C_6$ optionally substituted heteroaryl and; $R_2$ is selected from the group consisting of H, $C_1$-$C_4$ alkyl, ($C_1$-$C_4$ alkyl)OH and ($C_1$-$C_4$ alkyl)NH$_2$; $R_{23}$ is H or $C_1$-$C_4$ alkyl, and $R_{15}$ is a phosphonate ester or a phosphate ester or a pharmaceutically acceptable salt or tautomer thereof.

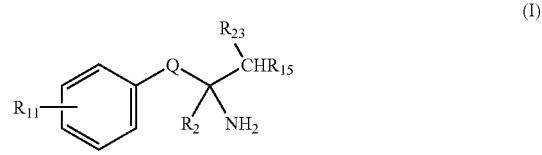

(I)

25 Claims, 14 Drawing Sheets

FOREIGN PATENT DOCUMENTS

| WO | WO 2004/010987 A2 | 7/2003 |
|---|---|---|
| WO | WO 2004/017917 A2 | 3/2004 |
| WO | WO 2004/024673 A1 | 3/2004 |
| WO | WO 2004/028521 A2 | 4/2004 |
| WO | WO 2004/047743 A2 | 6/2004 |
| WO | WO 2004/096752 A1 | 11/2004 |
| WO | WO 2004/096757 A1 | 11/2004 |
| WO | WO 2004/103279 A2 | 12/2004 |
| WO | WO 2004/103306 A2 | 12/2004 |
| WO | WO 2005/032465 A2 | 4/2005 |
| WO | WO 2005/118523 A1 | 12/2005 |
| WO | WO 2006/001463 A1 | 1/2006 |
| WO | WO 2006/020951 A1 | 2/2006 |
| WO | WO 2006/063033 A2 | 6/2006 |
| WO | WO 2006/088944 A1 | 8/2006 |
| WO | WO 2007/085451 A2 | 8/2007 |
| WO | WO 2007/086001 A2 | 8/2007 |
| WO | WO 2007/091396 A1 | 8/2007 |
| WO | WO 2007/092638 A1 | 8/2007 |
| WO | WO 2008/064315 A1 | 5/2008 |
| WO | WO 2008/064320 A2 | 5/2008 |
| WO | WO 2008/064337 A2 | 5/2008 |
| WO | WO 2009/023854 A1 | 2/2009 |
| WO | WO 2009/043013 A2 | 4/2009 |

OTHER PUBLICATIONS

Bandini, Marco et al., "An Effective and Useful Synthesis of Enantiomerically Enriched Arylglycinols", *Eur. J. Chem.* 2001, 1937-1942.
Beilstein, XP-002380276.
Bertus, Phillipe et al., "New and easy route to primary cyclopropylamines from nitriles", *Chem Commun*, 2001, 1792-1793.
Brinkmann, V. et al., V., Davis, M. D., Heise, C. E., Albert, R., Cottens, S., Hof, R., Bruns, C., Prieschl, E., Baumruker, T., Hiestand, P., Foster, C. A., Zollinger, M., and Lynch, K. R. (2002) *J Biol Chem* 277, 21453-21457.
Brinkmann, V., Pinschewer, D. D., Feng, L., and Chen, S. (2001) *Transplantation* 72, 764-769.
Burger, Alfred et al., "1-Methyl-2-phenylcyclopropylamine", *Journal of Medicine and Pharmaceutical Chemistry*, vol. 4, No. 3, 1961.
Chiba, K., Yanagawa, Y., Masubuchi, Y., Kataoka, H., Kawaguchi, T., Ohtsuki, M., and Hoshino, Y. (1998) *J Immunol* 160, 5037-5044.
Clair, T., Aoki, J., Koh, E., Bandle, R. W., Nam, S. W., Ptaszynska, M. M., Mills, G. B., Schiffmann, E., Liotta, L. A., and Stracke, M. L. (2003).
Choi, D. et al., "Synthesis and Anticonvulsant Activities of N-Benzyl-2-acetamidopropionamide", *J Med Chem* 39, 1996, 1907-1916.
Foss, F. et al., "Synthesis, stability, and implications of phosphothioate agonists of sphingosine-1-phosphate receptors", *Bioorganic & Medicinal Chemistry* 15, 2005, 4470-4474.
Im, D. S. et al., "Characterization of the Human and Mouse Sphingsine 1-Phosphate Receptor, $S1P_5$ (Edg-8): Structure—Activity Replationship of Sphingosine 1-Phosphate Receptors", Biochemistry 40, 2001, 14053-14060.
Maki, T. et al., "Prevention of Autoimmune Diabetes By FTY720 in Nonobese Diabetic Mice", (2002) *Transplantation* 74, 1684-1686.
Maki, T. et al., "Prevention and Cure of Autoimmune Diabetes in Nonobese Diabetic Mice by Continuous Administration of FTY720", (2005) *Transplantation* 77, 1051-1055.
Clemens, J. et al., Bioorg. Med. Chem. Lett. 2004, vol. 14, pp. 4903-4906.
Kotera et al., Chem. Abst.: Registry Record 19352-04-6, (2008).
Brinkmann, V., Pinschewer, D. D., Feng, L., and Chen, S. (2001) *Transplantation* 72, 764-769.
Maki, T., Gottschalk, R., and Monaco, A.P. (2002) *Transplantation* 74, 1684-1686.
International Search Report for PCT/US2004/036563, (2006).

Clair, T., Aoki, J., Koh, E., Bandle, R. W., Nam, S. W., Ptaszynska, M. M., Mills, G. B., Schiffmann, E., Liotta, L. A., and Stracke, M. L. (2003) *Cancer Res* 63, 5446-5453.
Clemens, J. J., Davis, M. D., Lynch, K. R., and Macdonald, T. L. (2003) *Bioorg Med Chem Lett* 13, 3401-3404.
Clemens, Jeremy et al., "Synthesis of 4(5)-phenylimidazole-based analogs of sphingosine-1-phosphate and FTY720: Discovery of potent $S1P_1$ receptor agonists", *Bioorganic & Medicinal Chemistry Letters* 15 (2005) 3568-3572.
Crosignani, Stefano et al., "4-Naphthyl-Substituted Bis(Oxazoline): a New Easily Recoverable and Efficient Chiral Ligand in Asymetric Catalysis of the Diels-Alder Reaction", *Tetrahedron* 54 (1998) 15721-15730.
Davis, Michael D. et al., "Sphingosine 1-Phosphate Analogs as Receptor Antagonists", *The Journal of Biological Chemistry*, vol. 280, No. 11, 2005, 9833-9841.
Forrest, M., Sun, S. Y., Hajdu, R., Bergstrom, J., Card, D., Doherty, G., Hale, J., Keohane, C., Meyers, C., Milligan, J., Mills, S., Nomura, N., Rosen, H., Rosenbach, M., Shei, G. J., Singer, II, Tian, M., West, S., White, V., Xie, J., Proia, R. L., and Mandala, S. (2004) *J Pharmacol Exp Ther* 309, 758-768.
Foss, Frank W. et al., "Synthesis and biological evaluation of γ-aminophosphonates as potent, subtype-selective sphingosine 1-phosphate receptor agonists and antagonists", *Bioorganic & Medicinal Chemistry* 15, 2007, 663-677.
Fujino, M., Funeshima, N., Kitazawa, Y., Kimura, H., Amemiya, H., Suzuki, S., and Li, X. K. (2003) *J Pharmacol Exp Ther* 305, 70-77.
Graler, M. H., and Goetzl, E. J. (2004) *FASEB* 18, 551-553.
Hale, Jeffrey J. et al., "Potent S1P receptor agonists replicate the pharmacologic actions of the novel immune modulator FTY720", *Bioorganic & Medicinal Chemistry Letters* 14, 2004, 3351-3355.
Hale, J. J., Doherty, G., Toth, L., Mills, S. G., Hajdu, R., Ann Keohane, C., Rosenbach, M., Milligan, J., Shei, G. J., Chrebet, G., Bergstrom, J., Card, D., Forrest, M., Sun, S. Y., West, S., Xie, H., Nomura, N., Rosen, H., and Mandala, S. (2004) *Bioorg Med Chem Lett* 14, 3501-3505.
Hale, J. J., Doherty, G., Toth, L., Li, Z., Mills, S. G., Hajdu, R., Ann Keohane, C., Rosenbach, M., Milligan, J., Shei, G. J., Chrebet, G., Bergstrom, J., Card, D., Rosen, H., and Mandala, S. (2004) *Bioorg Med Chem Lett* 14, 3495-3499.
Hale, Jeffrey J. et al., "A Rational Utilization of High-Throughput Screening Affords Selective, Orally Bioavailable 1-Benzyl-3-carboxyazetidine Sphingosine-1-phophate-1 Receptor Agonists", *J Med Chem*, 2004, 47, 6662-6665.
Hanessian, Stephen et al., Constrained azacyclic analogues of the immunomodulatory agent FTY270 as molecular probes for sphingosine 1-phosphate receptors:, *Bioorganic & Medicinal Chemistry Letters* 17, 2007, 491-494.
Hoshino, Y., Yanagawa, Y., Ohtsuki, M., Nakayama, S., Hashimoto, T., and Chiba, K. (1999) *Transplant Proc* 31, 1224-1226.
Im, D. S., Heise, C. E., Ancellin, N., O'Dowd, B. F., Shei, G. J., Heavens, R. P., Rigby, M. R., Hla, T., Mandala, S., McAllister, G., George, S. R., and Lynch, K. R. (2000) *J Biol Chem* 275, 14281-14286.
Jones, L., Schumm, J. S., and Tour, J. M. (1997) *J Org Chem* 62, 1388-1410.
Kaiser, Carl et al., "2-Substituted Cyclopropylamines. I. Derivatives and Analogs of 2-Phenylcyclopropylamine", XP009032189, Nov. 1962, 1243-1265.
Kawasaki, Ken-ichi et al., "Enantioselective Allylic Oxidation of Cycloalkenes by Using Cu(II)-Tris(oxazoline) Complex as a Catalyst", *Tetrahedron*, vol. 53, No. 18, 1997, 6337-6350.
Kharel, Yugesh et al., "Sphingosine Kinase 2 Is Required for Modulation of Lymphocyte Traffic by FTY 720", *J Bio Chem*, vol. 280, No. 44, Nov. 4, 2005, 36865-36872.
Kimura, T., Sato, K., Malchinkhuu, E., Tomura, H., Tamama, K., Kuwabara, A., Murakami, M., and Okajima, F. (2003) *Arterioscler Thromb Vasc Biol* 23, 1283-1288.
Kiuchi, M., Adachi, K., Kohara, T., Minoguchi, M., Hanano, T., Aoki, Y., Mishina, T., Arita, M., Nakao, N., Ohtsuki, M., Hoshino, Y., Teshima, K., Chiba, K., Sasaki, S., and Fujita, T. (2000) *J Med Chem* 43, 2946-2961.

Kon, J., Sato, K., Watanabe, T., Tomura, H., Kuwabara, A., Kimura, T., Tamama, K., Ishizuka, T., Murata, N., Kanda, T., Kobayashi, I., Ohta, H., Ui, M., and Okajima, F. (1999) *J Biol Chem* 274, 23940-23947.

Lee, M. J., Van Brocklyn, J. R., Thangada, S., Liu, C. H., Hand, A. R., Menzeleev, R., Spiegel, S., and Hla, T. (1998) *Science* 279, 1552-1555.

Lew, M. J., and Angus, J. A. (1995) *Trends Pharmacol Sci* 16, 328-337.

Li, Zhen et al., "Discovery of Potent 3,5-Diphenyl-1,2,4-oxadiazole Sphingosine-1-phosphate-1 ($S1P_1$) Receptor Agonists with Exceptional Selectivity against $S1P_2$ and $S1P_3$", *Journal of Medicinal Chemistry*, vol. 48, No. 20, Oct. 6, 2005, 6169-6173.

Maki, T., Gottschalk, R., and Monaco, A. P. (2002) *Transplantation* 74, 1684-1686.

Mandala, S., Hajdu, R., Bergstrom, J., Quackenbush, E., Xie, J., Milligan, J., Thornton, R., Shei, G. J., Card, D., Keohane, C., Rosenbach, M., Hale, J., Lynch, C. L., Rupprecht, K., Parsons, W., and Rosen, H. (2002) *Science* 296, 346-349.

Matloubian, M., Lo, C. G., Cinamon, G., Lesneski, M. J., Xu, Y., Brinkmann, V., Allende, M. L., Proia, R. L., and Cyster, J. G. (2004) *Nature* 427, 355-360.

Sanchez, T., Estrada-Hernandez, T., Paik, J. H., Wu, M. T., Venkataraman, K., Brinkmann, V., Claffey, K., and Hla, T. (2003) *J Biol Chem* 278, 47281-47290.

Sanna, M. Germana et al., "Enhancement of capillary leakage and restoration of lymphocyte egress by a chiral $S1P_1$ antagonist in vivo", *Nature Chemical Biology*, vol. 2, Aug. 2006, 434-441.

Sanna, M. G., Liao, J., Jo, E., Alfonso, C., Ahn, M. Y., Peterson, M. S., Webb, B., Lefebvre, S., Chun, J., Gray, N., and Rosen, H. (2004) *J Biol Chem* 279, 13839-13848.

Suzuki, S., Enosawa, S., Kakefuda, T., Li, X. K., Mitsusada, M., Takahara, S., and Amemiya, H. (1996) *Transpl Immunol* 4, 252-255.

Van Brocklyn, J. R., Tu, Z, Edsall, L. C., Schmidt, R. R., and Spiegel, S. (1999) *J Biol Chem* 274, 4626-4632.

Vogler, Rüdiger et al., "Sphingosine-1-Phosphate and Its Paradoxical Effects on Critical Parameters of Cutaneous Wound Healing", *The Journal of Investigative Dermatology*, vol. 48, No. 20, 2005, 6169-6173.

Xie, J. H., Nomura, N., Koprak, S. L., Quackenbush, E. J.; Forrest, M. J., and Rosen, H. (2003) *J Immunol* 170, 3662-3670.

Yanagawa, Y., Hoshino, Y., and Chiba, K. (2000) *Int J Immunopharmacol* 22, 597-602.

Yanagawa, Y., Hoshino, Y., Kataoka, H., Kawaguchi, T., Ohtsuki, M., Sugahara, K., and Chiba, K. (1999) *Transplant Proc* 31, 1227-1229.

Yang, Z., Chen, M., Fialkow, L. B., Ellett, J. D., Wu, R., Brinkmann, V., Nadler, J. L., and Lynch, K. R. (2003) *Clin Immunol* 107, 30-35.

Zhang, T., Nanney, L. B, Luongo, C., Lamps, L., Heppner, K. J., DuBois, R. N., and Beauchamp, R. D. (1997) *Cancer Res* 57, 169-175.

Zhang, Y. H. et al., "Sphingosine-1-Phosphate Via Activation of a G-Protein-Coupled Receptor(s) Enhances the Excitability of Rat Sensory Neurons", *J Neurophysiol* 96, 2006, 1042-1052.

Zhang, Y. H. et al., "Intracellular sphingosine 1-phosphate mediates the increased excitability produced by nerve growth factor in rat sensory neurons", *J Physiol* 575.1, 2006, 101-113.

ORALLY AVAILABLE SPHINGOSINE 1-PHOSPHATE RECEPTOR AGONISTS AND ANTAGONISTS

CROSS REFERENCE TO RELATED APPLICATIONS

The present application is a national stage filing of International Application No. PCT/US2004/036563, filed on Nov. 3, 2004, which claims priority under 35 U.S.C. § 119(e) to U.S. Provisional Application No. 60/516,887 filed on Nov. 3, 2003 the entire disclosures of which are hereby incorporated by reference herein in their entirety.

US GOVERNMENT RIGHTS

This invention was made with United States Government support under Grant No. NIH R01 GM52722 and NIH R01 CA88994 awarded by National Institutes of Health. The United States Government has certain rights in the invention.

BACKGROUND

Sphingosine-1-phosphate (S1P) has been demonstrated to induce many cellular effects, including those that result in platelet aggregation, cell proliferation, cell morphology, tumor-cell invasion, endothelial cell chemotaxis and endothelial cell in vitro angiogenesis. For these reasons, S1P receptors are good targets for therapeutic applications such as wound healing and tumor growth inhibition. Sphingosine-1-phosphate signals cells in part via a set of G protein-coupled receptors named S1P1, S1P2, S1P3, S1P4, and S1P5 (formerly Edg-1, Edg-5, Edg-3, Edg-6, and Edg-8, respectively). These receptors share 50-55% identical amino acids and cluster with three other receptors (LPA1, LPA2, and LPA3 (formerly Edg-2, Edg-4 and Edg-7)) for the structurally related lysophosphatidic acid (LPA).

A conformational shift is induced in the G-Protein Coupled Receptor (GPCR) when the ligand binds to that receptor, causing GDP to be replaced by GTP on the α-subunit of the associated G-proteins and subsequent release of the G-proteins into the cytoplasm. The α-subunit then dissociates from the βγ-subunit and each subunit can then associate with effector proteins, which activate second messengers leading to a cellular response. Eventually the GTP on the G-proteins is hydrolyzed to GDP and the subunits of the G-proteins reassociate with each other and then with the receptor. Amplification plays a major role in the general GPCR pathway. The binding of one ligand to one receptor leads to the activation of many G-proteins, each capable of associating with many effector proteins leading to an amplified cellular response.

S1P receptors make good drug targets because individual receptors are both tissue and response specific. Tissue specificity of the S1P receptors is desirable because development of an agonist or antagonist selective for one receptor localizes the cellular response to tissues containing that receptor, limiting unwanted side effects. Response specificity of the S1P receptors is also of importance because it allows for the development of agonists or antagonists that initiate or suppress certain cellular responses without affecting other responses. For example, the response specificity of the S1P receptors could allow for an S1P mimetic that initiates platelet aggregation without affecting cell morphology.

Sphingosine-1-phosphate is formed as a metabolite of sphingosine in its reaction with sphingosine kinase and is stored in abundance in the aggregates of platelets where high levels of sphingosine kinase exist and sphingosine lyase is lacking. S1P is released during platelet aggregation, accumulates in serum, and is also found in malignant ascites. Biodegradation of S1P most likely proceeds via hydrolysis by ectophosphohydrolases, specifically the sphingosine 1-phosphate phosphohydrolases.

The physiologic implications of stimulating individual S1P receptors are largely unknown due in part to a lack of receptor type selective ligands. Isolation and characterization of S1P analogs that have potent agonist or antagonist activity for S1P receptors has been limited due to the complication of synthesis derived from the lack of solubility of S1P analogs. Therefore, there is a need for compounds that have strong affinity and high selectivity for S1P receptor subtypes. The present invention satisfies these needs.

SUMMARY OF VARIOUS EMBODIMENTS OF THE INVENTION

One embodiment of the present invention is directed to novel phosphate esters of sphingosine-1-phosphate analogs, compositions comprising such analogs, and methods of using such analogs as agonist or antagonists of sphingosine-1-phosphate receptor activity to treat a wide variety of human disorders. The phosphate ester analogs of the present invention have improved oral availability, and include compounds that function as agonists, with various degrees of selectivity at individual S1P receptor subtypes, as well as compounds that function as antagonists at S1P receptors. In one embodiment, the S1P analogs of the present invention include compounds with the general structure:

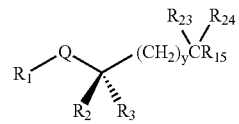

I wherein Q is selected from the group consisting of $C_3$-$C_6$ optionally substituted cycloalkyl, $C_3$-$C_6$ optionally substituted heterocyclic, $C_3$-$C_6$ optionally substituted aryl, $C_3$-$C_6$ optionally substituted heteroaryl and

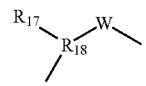

$R_1$ is selected from the group consisting of alkyl, alkenyl, alkynyl, alkyl(optionally substituted aryl), arylalkyl, and arylalkyl(optionally substituted)aryl;

$R_{17}$ is H, alkyl, alkylaryl or alkyl(optionally substituted aryl);

$R_{18}$ is N, O, S, CH or together with $R_{17}$ form a carbonyl group or a bond;

W is NH, $CH_2$, or $(CH_2)_n NH(CO)$;

$R_2$ and $R_3$ are independently selected from the group consisting of H, $NH_2$, C1-$C_6$ alkyl, ($C_1$-$C_4$ alkyl)OH, and ($C_1$-$C_4$ alkyl)$NH_2$, with the proviso that $R_2$ and $R_3$ are not the same and either $R_2$ or $R_3$ is $NH_2$.

$R_{23}$ is selected from the group consisting of H, F, $NH_2$, OH, $CO_2H$, $C_1$-$C_6$ alkyl, ($C_1$-$C_4$ alkyl)OH, and ($C_1$-$C_4$ alkyl)$NH_2$;

$R_{24}$ is selected from the group consisting of H, F, $CO_2H$, OH and $PO_3H_2$, or $R_{23}$ together with $R_{24}$ and the carbon to which they are attached form a carbonyl group;

$R_{15}$ is selected from the group consisting of hydroxy,

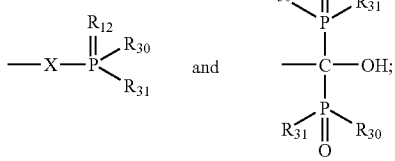

wherein $R_{12}$ is selected from the group consisting of O and S;

X is selected from the group consisting of O, NH, S, $CH_2$, CHOH, CHF, $CF_2$, and

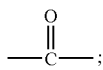

and $R_{30}$ and $R_{31}$ are independently selected from the group consisting of alkoxy, alkenyloxy, alkynyloxy, aryloxy,

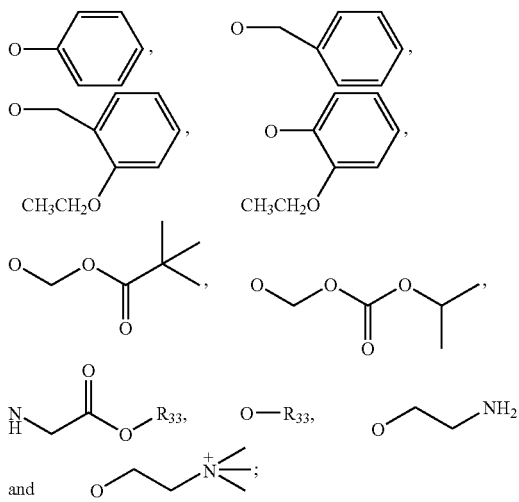

wherein $R_{33}$ is selected from the group consisting of $C_1$-$C_4$ alkyl, $C_2$-$C_4$ alkenyl, $C_2$-$C_4$ alkynyl and optionally substituted aryl;

y is an integer ranging from 0-10; n is an integer ranging from 0-4; and pharmaceutically acceptable salts and tautomers of such compounds. Selective agonists and antagonists at S1P receptors, and their corresponding prodrug derivatives, will be useful as therapeutics for treating a wide variety of human disorders.

BRIEF DESCRIPTION OF THE DRAWINGS

FIG. 1A=S1P1 receptor, FIG. 1B=S1P3 receptor, FIG. 1C=S1P2 receptor, FIG. 1D=S1P4 receptor, FIG. 1E=S1P5 receptor, and FIG. 1F=S1P3 receptor. Each data point represents the mean of three determinations (CPM=counts per minute).

FIG. 2A=S1P1 receptor, FIG. 2B=S1P3 receptor, FIG. 2C=S1P2 receptor, FIG. 2D=S1P4 receptor, and FIG. 2E=S1P5 receptor. Each data point represents the mean of three determinations (CPM=counts per minute).

FIG. 3A=S1P1 receptor, FIG. 3B=S1P3 receptor, FIG. 3C=S1P2 receptor, FIG. 3D=S1P4 receptor, and FIG. 3E=S1P5 receptor. Each data point represents the mean of three determinations (CPM=counts per minute).

FIG. 4A=S1P1 receptor, FIG. 4B=S1P3 receptor, FIG. 4C=S1P2 receptor, FIG. 4D=S1P4 receptor, and FIG. 4E=S1P5 receptor. Each data point represents the mean of three determinations (CPM=counts per minute).

FIG. 5A is a graphic representation of [γ-$^{35}$S]GTP binding to HEK293T cell membranes containing the S1P1 receptor, in response to S1P, VPC23087 and VPC23087+S1P. FIG. 5B is a graphic representation of [γ-$^{35}$S]GTP binding to HEK293T cell membranes containing the S1P3 receptor, in response to S1P, VPC23089 and VPC23089+S1P. Each data point represents the mean of three determinations (CPM=counts per minute).

FIG. 6A=S1P1 receptor, FIG. 6B=S1P3 receptor, FIG. 6C=S1P4 receptor, and FIG. 6D=S1P5 receptor. Each data point represents the mean of three determinations, wherein the activity of VPC24289 and VPC24287 is measured relative to S1P activity at the specific receptor subtype.

DETAILED DESCRIPTION OF EMBODIMENTS

Definitions

Figure 1A:
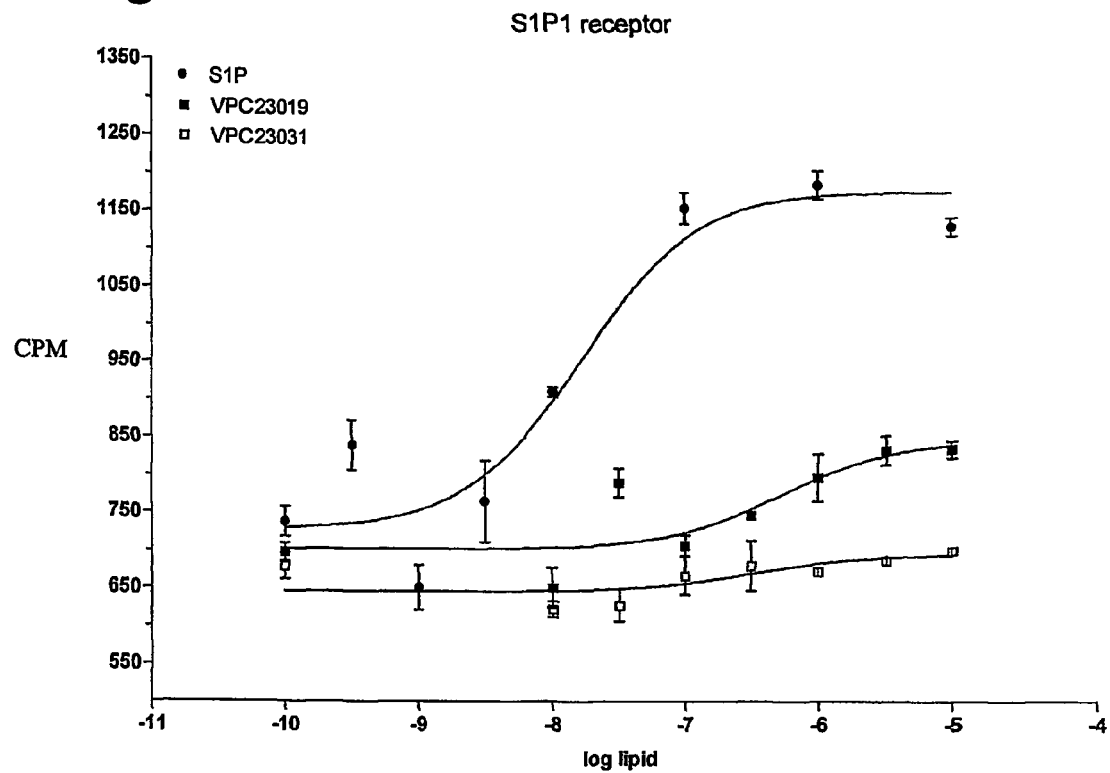
FIG. 1A-1F are graphic representations of [γ-$^{35}$S]GTP binding to HEK293T cell membranes (containing different S1P receptors) in response to S1P, VPC23019 and VPC23031.
Figure 1B:
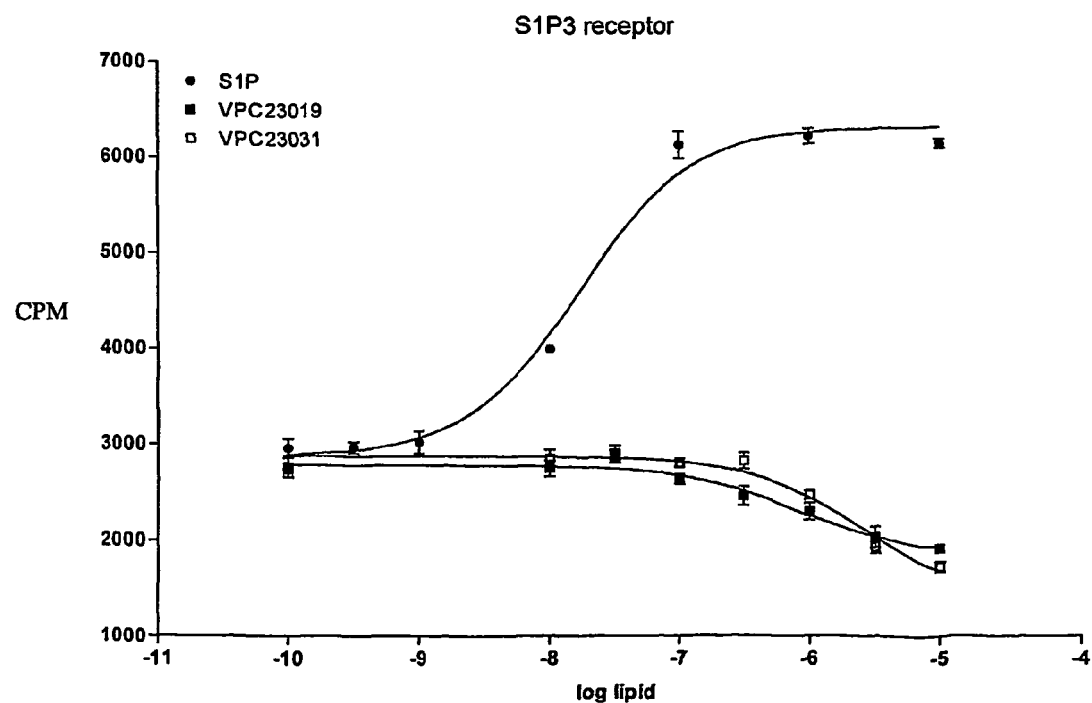
Figure 1C:
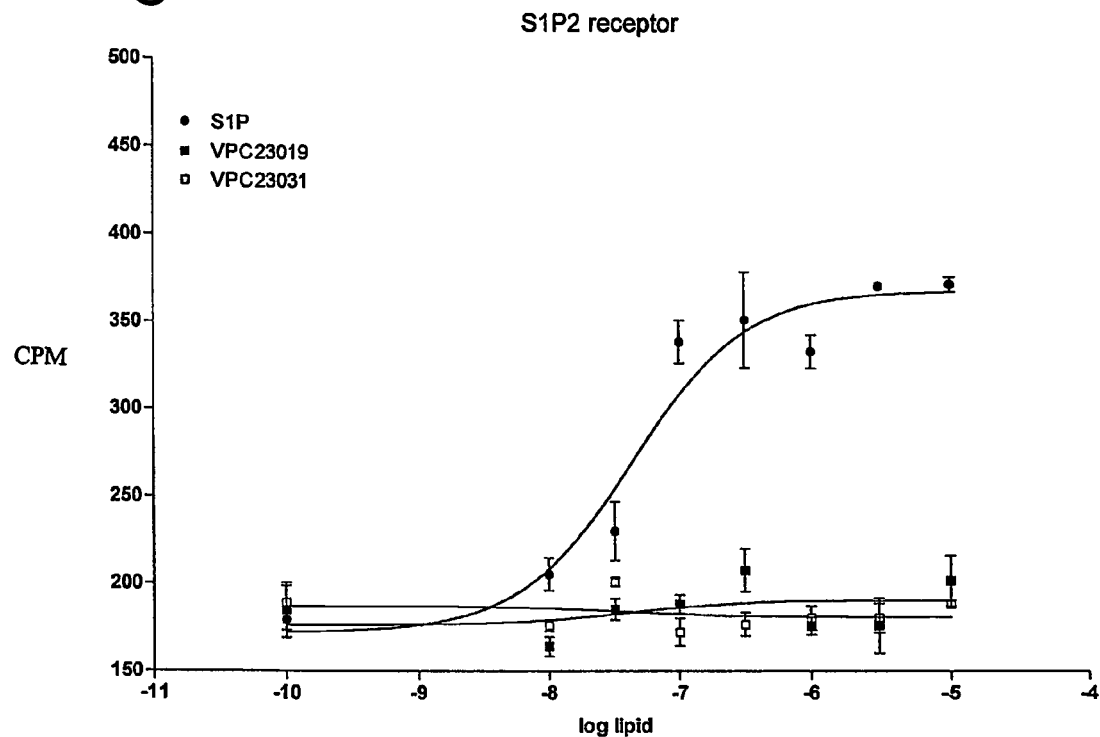
Figure 1D:
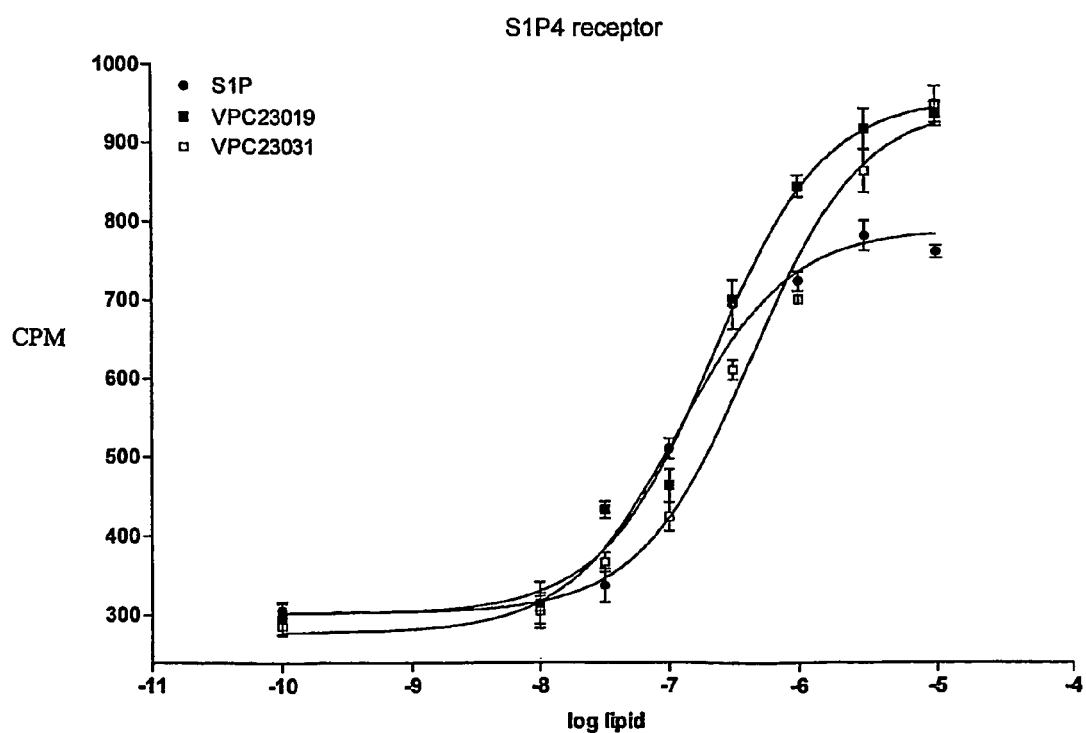
Figure 1E:
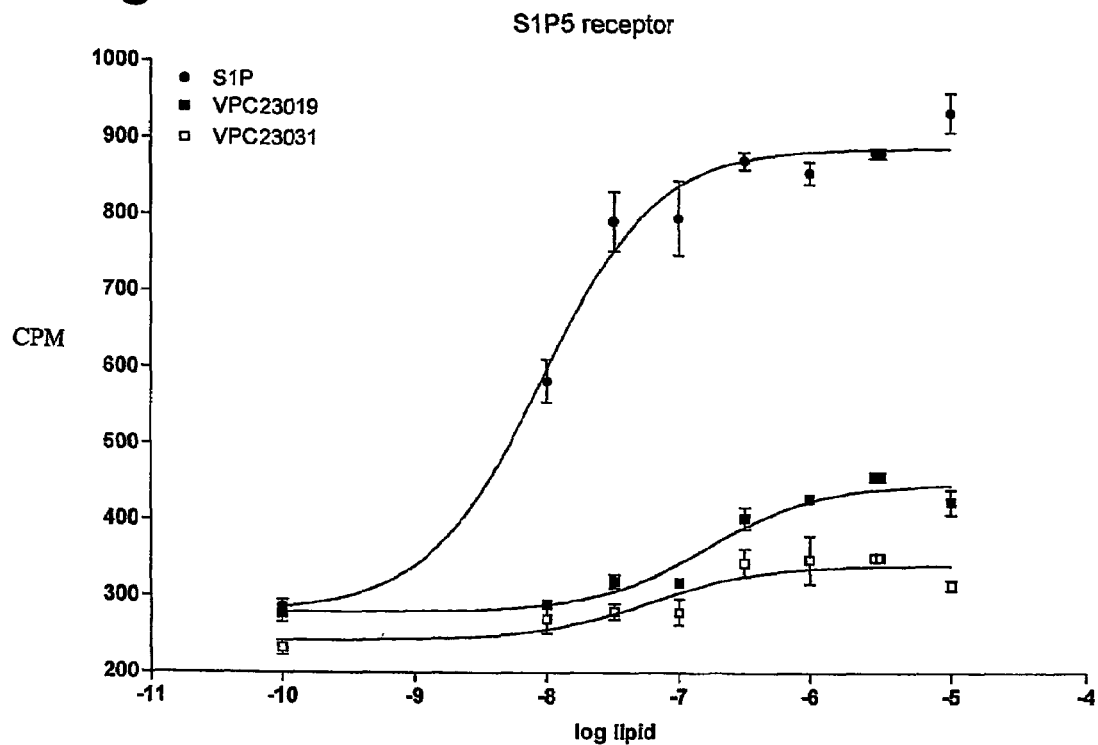
Figure 1F:
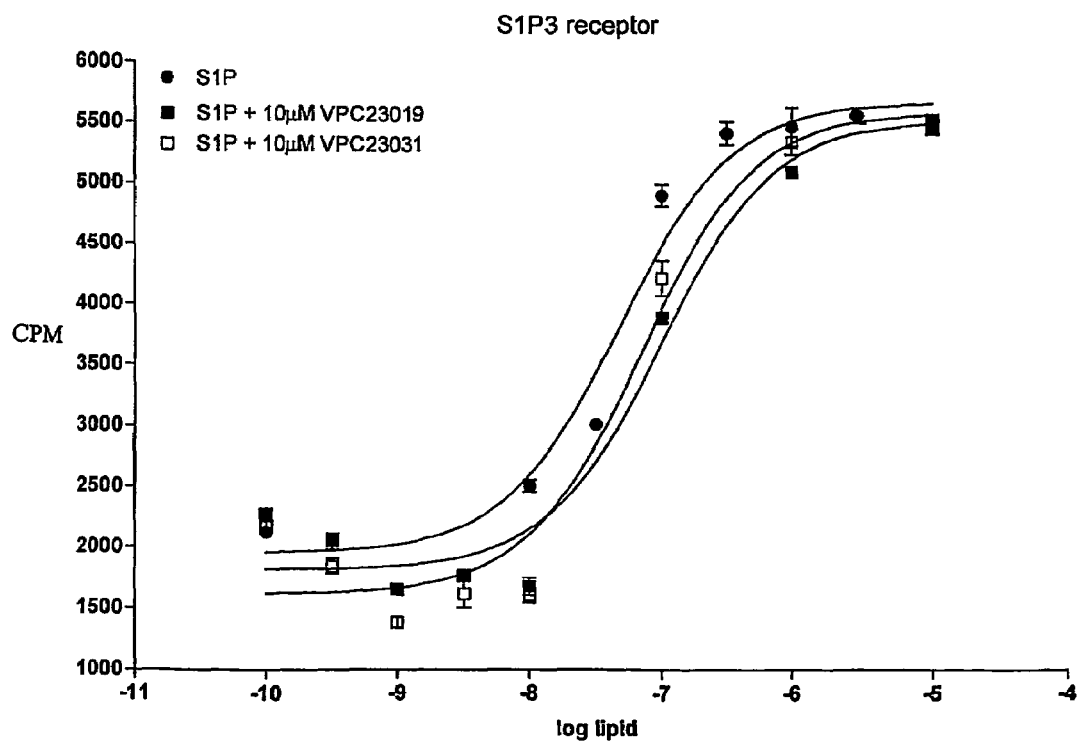

Unless defined otherwise, all technical and scientific terms used herein have the same meaning as commonly understood by one of ordinary skill in the art to which this invention belongs.

In describing and claiming the invention, the following terminology will be used in accordance with the definitions set forth below.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "treating" includes prophylaxis of the specific disorder or condition, or alleviation of the symptoms associated with a specific disorder or condition and/or preventing or eliminating said symptoms.

As used herein, an "effective amount" means an amount sufficient to produce a selected effect. For example, an effective amount of an S1P receptor antagonist is an amount that decreases the cell signaling activity of the S1P receptor.

As used herein, the term "halogen" or "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "$C_1$-$C_n$ alkyl" wherein n is an integer, as used herein, represents a branched or linear alkyl group having from one to the specified number of carbon atoms. Typically $C_1$-$C_6$ alkyl groups include, but are not limited to, methyl, ethyl, n-propyl, iso-propyl, butyl, iso-butyl, sec-butyl, tert-butyl, pentyl, hexyl and the like.

The term "$C_2$-$C_n$ alkenyl" wherein n is an integer, as used herein, represents an olefinically unsaturated branched or linear group having from 2 to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "$C_2$-$C_n$ alkynyl" wherein n is an integer refers to an unsaturated branched or linear group having from 2 to the specified number of carbon atoms and at least one triple bond. Examples of such groups include, but are not limited to, 1-propynyl, 2-propynyl, 1-butynyl, 2-butynyl, 1-pentynyl, and the like.

The term "$C_3$-$C_n$ cycloalkyl" wherein n=8, represents cyclopropyl, cyclobutyl, cyclopentyl, cyclohexyl, cycloheptyl, and cyclooctyl.

As used herein, the term "optionally substituted" refers to from zero to four substituents, wherein the substituents are each independently selected. Each of the independently selected substituents may be the same or different than other substituents.

As used herein the term "aryl" refers to a mono- or bicyclic carbocyclic ring system having one or two aromatic rings including, but not limited to, phenyl, benzyl, naphthyl, tetrahydronaphthyl, indanyl, indenyl, and the like. "Optionally substituted aryl" includes aryl compounds having from zero to four substituents, and "substituted aryl" includes aryl compounds having one to three substituents, wherein the substituents, including alkyl, halo or amino substituents. The term ($C_5$-$C_8$ alkyl)aryl refers to any aryl group which is attached to the parent moiety via the alkyl group, and the term ($C_5$-$C_8$ alkyl)($C_5$-$C_6$ aryl) refers to a five or six membered aromatic ring that is attached to the parent moiety via the $C_5$-$C_8$ alkyl group.

The term "heterocyclic group" refers to a mono- or bicyclic carbocyclic ring system containing from one to three heteroatoms wherein the heteroatoms are selected from the group consisting of oxygen, sulfur, and nitrogen.

As used herein the term "heteroaryl" refers to a mono- or bicyclic carbocyclic ring system having one or two aromatic rings containing from one to three heteroatoms and includes, but is not limited to, furyl, thienyl, pyridyl and the like.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The term "lower alkyl" as used herein refers to branched or straight chain alkyl groups comprising one to eight carbon atoms, including methyl, ethyl, propyl, isopropyl, n-butyl, t-butyl, neopentyl and the like.

The terms 16:0, 18:0, 18:1, 20:4 or 22:6 hydrocarbon refers to a branched or straight alkyl or alkenyl group, wherein the first integer represents the total number of carbons in the group and the second integer represent the number of double bonds in the group.

As used herein, an "S1P modulating agent" refers a compound or composition that is capable of inducing a detectable change in S1P receptor activity in vivo or in vitro (e.g., at least 10% increase or decrease in S1P activity as measured by a given assay such as the bioassay described in Example 4). "S1P receptor," as used herein, refers to all of the S1P receptor subtypes (for example, the S1P receptors S1P1, S1P2, S1P3, S1P4, and S1P5), unless the specific subtype is indicated.

As used herein, the term "$EC_{50}$ of an agent" refers to that concentration of an agent at which a given activity, including binding of sphingosine or other ligand of an S1P receptor and/or a functional activity of a S1P receptor (e.g., a signaling activity), is 50% maximal for that S1P receptor. Stated differently, the $EC_{50}$ is the concentration of agent that gives 50% activation, when 100% activation is set at the amount of activity of the S1P receptor which does not increase with the addition of more ligand/agonist and 0% is set at the amount of activity in the assay in the absence of added ligand/agonist.

As used herein, the term "phosphate analog" and "phosphonate analog" comprise analogs of phosphate and phosphonate wherein the phosphorous atom is in the +5 oxidation state and one or more of the oxygen atoms is replaced with a non-oxygen moiety, including for example, the phosphate analogs phosphorothioate, phosphorodithioate, phosphoroselenoate, phosphorodiselenoate, phosphoroanilothioate, phosphoranilidate, phosphoramidate, boronophosphates, and the like, including associated counterions, e.g., H, $NH_4$, Na, and the like if such counterions are present.

The S1P analogs of the present invention contain one or more asymmetric centers in the molecule. In accordance with the present invention a structure that does not designate the stereochemistry is to be understood as embracing all the various optical isomers, as well as racemic mixtures thereof.

The compounds of the present invention may exist in tautomeric forms and the invention includes both mixtures and separate individual tautomers. For example the following structure:

is understood to represent a mixture of the structures:

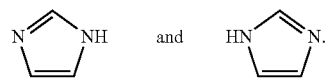

The term "pharmaceutically-acceptable salt" refers to salts which retain the biological effectiveness and properties of the S1P analogs of the present invention and which are not biologically or otherwise undesirable. In many cases, the S1P analogs of the present invention are capable of forming acid and/or base salts by virtue of the presence of amino and/or carboxyl groups or groups similar thereto.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl)amines, tri(substituted alkyl)amines, alkenyl amines, dialkenyl amines, trialkenyl amines, substituted alkenyl amines, di(substituted alkenyl)amines, tri(substituted alkenyl)amines, cycloalkyl amines, di(cycloalkyl)amines, tri(cycloalkyl)amines, substituted cycloalkyl amines, disubstituted cycloalkyl amine, trisubstituted cycloalkyl amines, cycloalkenyl amines, di(cycloalkenyl)amines, tri(cycloalkenyl)amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and triamines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Examples of suitable amines include, by way of example only, isopropylamine, trimethyl amine, diethyl amine, tri(iso-propyl)amine, tri(n-propyl)amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

EMBODIMENTS

One aspect of the present invention is directed to novel S1P analogs that have activity as modulators of S1P receptor activity. Modulators of S1P activity include agents that have either agonist or antagonist activity at the S1P receptor as well as analogs of those compounds that have been modified to resist enzymatic modification (i.e. block modification of the compounds by phosphohydrolases, sphingosine lyases or sphingosine kinases), or provide a suitable substrate for sphingosine kinases to convert an administered form into a more active form.

One embodiment of the present invention is directed to improved S1P modulating compound derivatives, wherein the compounds have been modified to enhance their oral availability and thus increase their efficacy in oral pharmaceutical formulations. The compounds of the present invention modulate S1P receptor function through a variety of different mechanisms including their functioning as a receptor antagonist, receptor agonist (full or partial), or as inhibitors of S1P phosphatases or synthetic enzymes such as sphingosine kinase or autotoxin. More particularly, the prodrug derivatives of the present invention are phospho-ester derivatives that have enhanced oral availability relative to the parent compound. After the compounds are absorbed from the alimentary canal of the animal being administered the compound, the phospho-ester is cleaved to regenerate the active form of the compound.

In accordance with one embodiment, an S1P receptor-modulating compound is provided wherein the compound has the general structure:

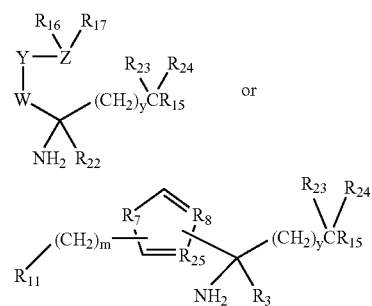

wherein

W is $CR_{27}R_{28}$ or $(CH_2)_n NH(CO)$;

wherein $R_{27}$ and $R_{28}$ are independently selected from the group consisting of H, halo and hydroxy;

Y is selected from the group consisting of a bond, $CR_9R_{10}$, carbonyl, NH, O or S;

wherein $R_9$ and $R_{10}$ are independently selected from the group consisting of H, halo, hydroxy and amino;

Z is $CH_2$, aryl, flourine substituted aryl or heteroaryl;

$R_{11}$ and $R_{16}$ are independently selected from the group consisting of $C_1$-$C_{18}$ alkyl, $C_2$-$C_{18}$ alkenyl, $C_2$-$C_{18}$ alkynyl, $C_5$-$C_{18}$ alkoxy, $(CH_2)_p O(CH_2)_q$, $C_1$-$C_8$ alkyl($C_5$-$C_{10}$ aryl)$R_{40}$, $C_1$-$C_8$ alkyl($C_5$-$C_{10}$ heteroaryl)$R_{40}$, $C_1$-$C_8$ alkyl($C_5$-$C_{10}$ cycloalkyl)$R_{40}$, $C_1$-$C_{10}$ alkoxy($C_5$-$C_{10}$ aryl)$R_{40}$, $C_1$-$C_{10}$ alkoxy($C_5$-$C_{10}$ heteroaryl)$R_{40}$ and $C_1$-$C_{10}$ alkoxy($C_5$-$C_{10}$ cycloalkyl)$R_{40}$;

wherein $R_{40}$ is selected from the group consisting of H, $C_1$-$C_{12}$ alkyl, $C_2$-$C_{12}$ alkenyl, ($C_5$-$C_{10}$ cycloalkyl)$R_{20}$, $C_1$-$C_{10}$ alkoxy($C_5$-$C_{10}$ aryl)$R_{20}$, $C_1$-$C_{10}$ alkoxy($C_5$-$C_{10}$ heteroaryl)$R_{20}$ and $C_1$-$C_{10}$ alkoxy($C_5$-$C_{10}$ cycloalkyl)$R_{20}$;

wherein $R_{20}$ is H or $C_1$-$C_{10}$ alkyl;

$R_{17}$ is selected from the group consisting of H, halo, $NH_2$, $C_1$-$C_6$ alkyl, $C_1$-$C_6$ alkoxy, $C_1$-$C_6$ alkylamino, $C_1$-$C_6$ alkylcyano and $C_1$-$C_6$ alkylthio;

$R_3$ is selected from the group consisting of H, $C_1$-$C_6$ alkyl, ($C_1$-$C_4$ alkyl)OH, ($C_1$-$C_4$ alkyl)$NH_2$, ($C_1$-$C_4$ alkyl)aryl($C_0$-$C_4$ alkyl) and ($C_1$-$C_4$ alkyl)aryloxyaryl($C_0$-$C_4$ alkyl);

$R_{22}$ is selected from the group consisting of $C_1$-$C_6$ alkyl, ($C_1$-$C_4$ alkyl)OH, ($C_1$-$C_4$ alkyl)$NH_2$, ($C_1$-$C_4$ alkyl)aryl($C_0$-$C_4$ alkyl) and ($C_1$-$C_4$ alkyl)aryloxyaryl($C_0$-$C_4$ alkyl);

$R_{23}$ is selected from the group consisting of H, F, $NH_2$, OH, $CO_2H$, $C_1$-$C_6$ alkyl, ($C_1$-$C_4$ alkyl)OH, and ($C_1$-$C_4$ alkyl)$NH_2$;

$R_{24}$ is selected from the group consisting of H, F, $CO_2H$, OH and $PO_3H_2$, or $R_{23}$ together with $R_{24}$ and the carbon to which they are attached form a carbonyl group;

$R_{25}$, $R_7$ and $R_8$ are independently selected from the group consisting of O, S, $CHR_{26}$, $CR_{26}$, $NR_{26}$, and N;

wherein $R_{26}$ is H or $C_1$-$C_4$ alkyl;

$R_{15}$ is selected from the group consisting of hydroxy, phosphonate, and $$-X-\overset{\overset{R_{12}}{\|}}{P}\overset{R_{30}}{\underset{R_{31}}{\diagdown}};$$

wherein $R_{12}$ is selected from the group consisting of O, NH and S;

X is selected from the group consisting of O, NH, S, $CH_2$, CHOH, CHF, $CF_2$, and $$-\overset{O}{\overset{\|}{C}}-;$$

and $R_{30}$ and $R_{31}$ are independently selected from the group consisting of $C_1$-$C_2$ alkoxy, hydroxy,

[chemical structures]

y and m are integers independently ranging from 0 to 4;
p and q are integers independently ranging from 1 to 10;
n is an integer ranging from 0 to 10;

or a pharmaceutically acceptable salt or tautomer thereof, with the proviso that when W and Y are both methylene, $R_{30}$ and $R_{31}$ are independently selected from the group consisting of

[chemical structures]

In one embodiment the present invention is directed to a S1P receptor modulating compound is represented by the formula:

$$\text{II}$$

[chemical structure showing formula II with $R_{16}$, $R_{17}$, Z, $(CH_2)_n$, N, H, $R_{21}$, $NH_2$, O, $(CH_2)_y$, $CR_{15}$, $R_{23}$, $R_{24}$]

wherein

Z is $CH_2$, $C_5$-$C_{10}$ aryl or $C_5$-$C_{10}$ heteroaryl;

$R_{16}$ is selected from the group consisting of $C_1$-$C_{18}$ alkyl, $C_2$-$C_{18}$ alkenyl, $C_2$-$C_{18}$ alkynyl, $C_5$-$C_{18}$ alkoxy, $(CH_2)_pO(CH_2)_q$, $C_1$-$C_8$ alkyl($C_5$-$C_{10}$ aryl)$R_{20}$, $C_1$-$C_8$ alkyl($C_5$-$C_{10}$ heteroaryl)$R_{20}$, $C_1$-$C_8$ alkyl($C_5$-$C_{10}$ cycloalkyl)$R_{20}$, $C_1$-$C_{10}$ alkoxy($C_5$-$C_{10}$ aryl)$R_{20}$, $C_1$-$C_{10}$ alkoxy($C_5$-$C_{10}$ heteroaryl)$R_{20}$ and $C_1$-$C_{10}$ alkoxy($C_5$-$C_{10}$ cycloalkyl)$R_{20}$, wherein $R_{20}$ is H or $C_1$-$C_{10}$ alkyl;

$R_{17}$ is selected from the group consisting of H, halo, $NH_2$, $C_1$-$C_6$ alkyl, $C_1$-$C_6$ alkoxy, $C_1$-$C_6$ alkylamino, $C_1$-$C_6$ alkylcyano and $C_1$-$C_6$ alkylthio;

$R_{21}$ is selected from the group consisting of $NH_2$, OH, $C_1$-$C_6$ alkyl, ($C_1$-$C_4$ alkyl)OH, ($C_1$-$C_4$ alkyl)$NH_2$, ($C_1$-$C_4$ alkyl)aryl($C_0$-$C_4$ alkyl) and ($C_1$-$C_4$ alkyl)aryloxyaryl($C_0$-$C_4$ alkyl), with the proviso that $R_2$ or $R_3$ is $NH_2$;

$R_{15}$ is $$-X-\overset{\overset{R_{12}}{\|}}{P}\overset{R_{30}}{\underset{R_{31}}{\diagdown}};$$

wherein $R_{12}$ is selected from the group consisting of O and S;

X is selected from the group consisting of S, $CH_2$, CHOH, CHF, $CF_2$, and

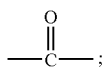

and $R_{30}$ and $R_{31}$ are independently selected from the group consisting of $C_1$-$C_2$ alkoxy, hydrogen, hydroxy,

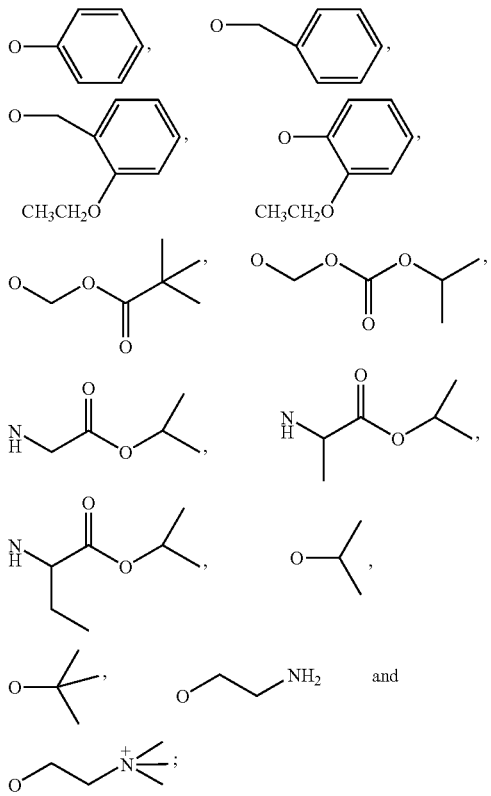

$R_{23}$ is selected from the group consisting of H, F, $NH_2$, OH, $CO_2H$, $C_1$-$C_6$ alkyl, ($C_1$-$C_4$ alkyl)OH, and ($C_1$-$C_4$ alkyl)$NH_2$;

$R_{24}$ is selected from the group consisting of H, F, $CO_2H$, OH and $PO_3H_2$, or $R_{23}$ together with $R_{24}$ and the carbon to which they are attached form a carbonyl group; p and q are integers independently ranging from 1 to 10;

y is an integer ranging from 0 to 4; and n is an integer ranging from 0 to 10;

or a pharmaceutically acceptable salt or tautomer thereof. In one embodiment the compound of Formula II is provided wherein Z is $CH_2$, y is 0, n is 1-10, $R_{23}$, $R_{24}$ and $R_{17}$ are each H. In another embodiment, the compound of Formula II is provided wherein Z is $C_5$-$C_6$ aryl or $C_5$-$C_6$ heteroaryl, y is 0, n is 0, $R_{23}$, $R_{24}$ and $R_{17}$ are each H and $R_{16}$ is selected from the group consisting of $C_5$-$C_{12}$ alkyl, $C_2$-$C_{12}$ alkenyl or $C_5$-$C_{12}$ alkoxy. In another embodiment, the compound of Formula II is provided wherein Z is $C_5$-$C_6$ aryl or $C_5$-$C_6$ heteroaryl, y is 0, n is 0, $R_{17}$, $R_{23}$ and $R_{24}$ are each H, $R_{16}$ is selected from the group consisting of $C_5$-$C_{12}$ alkyl, $C_2$-$C_{12}$ alkenyl or $C_5$-$C_{12}$ alkoxy and $R_{15}$ is

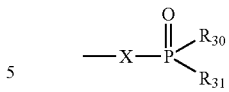

wherein X is $CH_2$, CHOH or CHF, and $R_{30}$ and $R_{31}$ are independently selected from the group consisting of

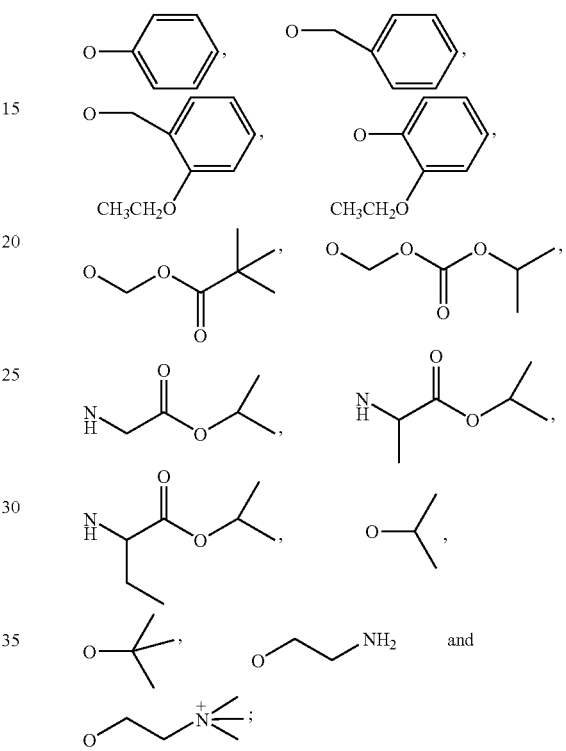

In another embodiment of the present invention a S1P receptor modulating compound is provided wherein the compound is represented by the formula:

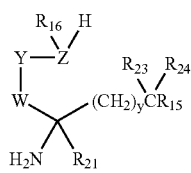

III wherein Z is $C_5$-$C_{10}$ aryl or $C_5$-$C_{10}$ heteroaryl;

$R_{16}$ is selected from the group consisting of $C_5$-$C_{18}$ alkyl, $C_5$-$C_{18}$ alkenyl, $C_5$-$C_{18}$ alkynyl and $C_5$-$C_{18}$ alkoxy;

Y is selected from the group consisting of CHOH, $CF_2$, CFH, carbonyl, NH, O and S;

W is $CR_{27}R_{28}$, wherein $R_{27}$ and $R_{28}$ are independently selected from the group consisting of H, halo and hydroxy;

$R_{21}$ is selected from the group consisting of $NH_2$, OH, $C_1$-$C_6$ alkyl, ($C_1$-$C_4$ alkyl)OH, ($C_1$-$C_4$ alkyl)$NH_2$, ($C_1$-$C_4$ alkyl)aryl($C_0$-$C_4$ alkyl) and ($C_1$-$C_4$ alkyl)aryloxyaryl($C_0$-$C_4$ alkyl);

$R_{23}$ is selected from the group consisting of H, F, $NH_2$, OH, $CO_2H$, $C_1$-$C_6$ alkyl, ($C_1$-$C_4$ alkyl)OH, and ($C_1$-$C_4$ alkyl)$NH_2$;

$R_{24}$ is selected from the group consisting of H, F, $CO_2H$, OH and $PO_3H_2$, or $R_{23}$ together with $R_{24}$ and the carbon to which they are attached form a carbonyl group;

$R_{15}$ is

[Structure: —X—P(=R_{12})(R_{30})(R_{31})]

wherein $R_{12}$ is selected from the group consisting of O and S;

X is selected from the group consisting of S, $CH_2$, CHOH, CHF, $CF_2$, and

[Structure: —C(=O)—]

and $R_{30}$ and $R_{31}$ are independently selected from the group consisting of

[Structures: O-phenyl; O-CH2-phenyl; O-CH2-(2-ethoxyphenyl); O-(2-ethoxyphenyl); O-CH2-O-C(=O)-C(CH3)3; O-CH2-O-C(=O)-O-CH(CH3)2; NH-CH2-C(=O)-O-CH(CH3)2; NH-CH2-C(=O)-O-CH2CH3; NH-CH(CH3)-C(=O)-O-CH(CH3)2; NH-CH(CH2CH3)-C(=O)-O-CH(CH3)2; O-CH(CH3)2; O-C(CH3)3; O-CH2CH2-NH2 and O-CH2CH2-N+(CH3)3];

and y is an integer ranging from 0 to 4;

or a pharmaceutically acceptable salt or tautomer thereof. In one embodiment the compound of Formula III is provided wherein Z is $C_5$-$C_6$ aryl or $C_5$-$C_6$ heteroaryl, $R_{23}$ and $R_{24}$ are both H, $R_{21}$ is selected from the group consisting of OH, $C_1$-$C_4$ alkyl, and ($C_1$-$C_3$ alkyl)OH; and y is 0.

In another embodiment, the compound is represented by the formula:

[Structure showing $R_{16}$-phenyl-Y-CH2-C(NH2)(R_{21})-C(R_{23})(R_{24})-R_{15}]   or

[Structure showing $R_{16}$-phenyl-Y-CH(R_{21})-C(NH2)-C(R_{23})(R_{24})-R_{15}]

wherein $R_{16}$ is selected from the group consisting of $C_5$-$C_{12}$ alkyl, $C_5$-$C_{12}$ alkenyl and $C_5$-$C_{12}$ alkynyl;

Y is selected from the group consisting of carbonyl, NH and O;

$R_{15}$ is

[Structure: —X—P(=R_{12})(R_{30})(R_{31})]

wherein $R_{12}$ is selected from the group consisting of O and S;

X is selected from the group consisting of S, $CH_2$, CHOH, CHF, $CF_2$, and

[Structure: —C(=O)—]

and $R_{30}$ and $R_{31}$ are independently selected from the group consisting of

[Structures: O-phenyl; O-CH2-phenyl; O-CH2-(2-ethoxyphenyl); O-(2-ethoxyphenyl); O-CH2-O-C(=O)-C(CH3)3; O-CH2-O-C(=O)-O-CH(CH3)2; NH-CH2-C(=O)-O-CH(CH3)2; NH-CH(CH3)-C(=O)-O-CH(CH3)2; NH-CH(CH2CH2-)-C(=O)-O-CH(CH3)2; O-CH(CH3)2; O-C(CH3)3; O-CH2CH2-NH2 and]

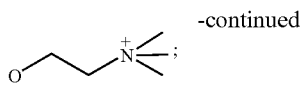

$R_{21}$ is selected from the group consisting of $C_1$-$C_6$ alkyl, ($C_1$-$C_4$ alkyl)OH and ($C_1$-$C_4$ alkyl)$NH_2$; $R_{23}$ and $R_{24}$ are independently selected from the group consisting of H, OH, F, $CO_2H$ or $PO_3H_2$ or $R_{23}$ together with $R_{24}$ and the carbon to which they are attached form a carbonyl group, as well as pharmaceutically acceptable salts and tautomers thereof.

In another embodiment, the compound of Formula III is provided wherein Z is $C_5$-$C_6$ aryl;

$R_{16}$ is selected from the group consisting of $C_5$-$C_{18}$ alkyl and $C_5$-$C_{18}$ alkenyl;

Y is selected from the group consisting of $CF_2$, CFH, carbonyl, NH, O and S;

W is $CH_2$;

$R_{21}$ is selected from the group consisting of $C_1$-$C_6$ alkyl, ($C_1$-$C_4$ alkyl)OH and ($C_1$-$C_4$ alkyl)$NH_2$;

$R_{23}$ and $R_{24}$ are both H; y is 0; and $R_{15}$ is

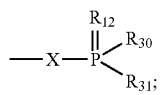

wherein $R_{12}$ is selected from the group consisting of O and S;

X is selected from the group consisting of S, $CH_2$, CHOH, CHF, $CF_2$, and

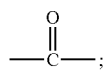

and $R_{30}$ and $R_{31}$ are independently selected from the group consisting of

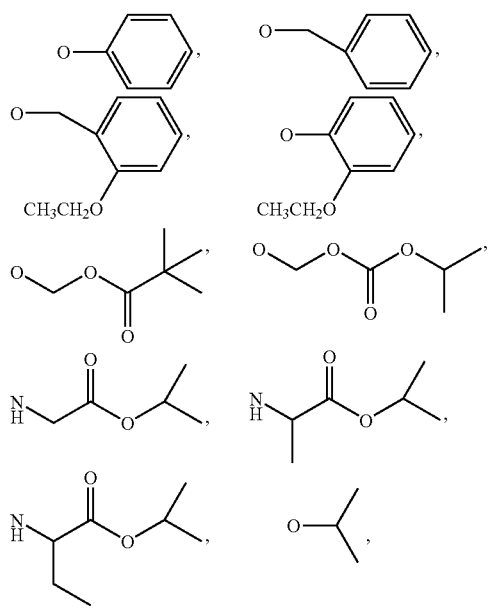

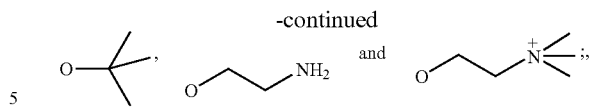

or a pharmaceutically acceptable salt or tautomer thereof.

In another embodiment of the present invention, a S1P receptor-modulating compound is provided wherein the compound is represented by the formula:

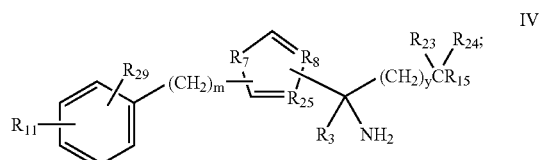

IV

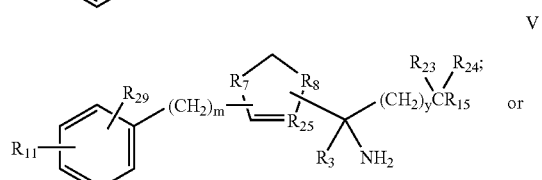

V or

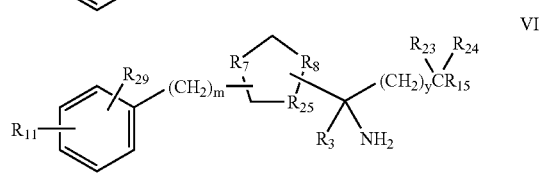

VI wherein $R_{11}$ is selected from the group consisting of $C_5$-$C_{12}$ alkyl, $C_5$-$C_{12}$ alkenyl and $C_5$-$C_{12}$ alkynyl;

$R_{29}$, is H or halo;

$R_{25}$, $R_7$ and $R_8$ are independently selected from the group consisting of O, S, $CHR_{26}$, $CR_{26}$, $NR_{26}$, and N;

wherein $R_{26}$ is H, F or $C_1$-$C_4$ alkyl;

$R_3$, is selected from the group consisting of H, $NH_2$, OH, $C_1$-$C_6$ alkyl, ($C_1$-$C_4$ alkyl)OH, ($C_1$-$C_4$ alkyl)$NH_2$, ($C_1$-$C_4$ alkyl)aryl($C_0$-$C_4$ alkyl) and ($C_1$-$C_4$ alkyl)aryloxyaryl($C_0$-$C_4$ alkyl);

$R_{15}$ is

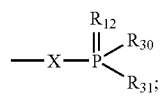

wherein $R_{12}$ is selected from the group consisting of O and S;

X is selected from the group consisting of O, S, $CH_2$, CHOH, CHF, $CF_2$, and

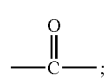

and $R_{30}$ and $R_{31}$ are independently selected from the group consisting of

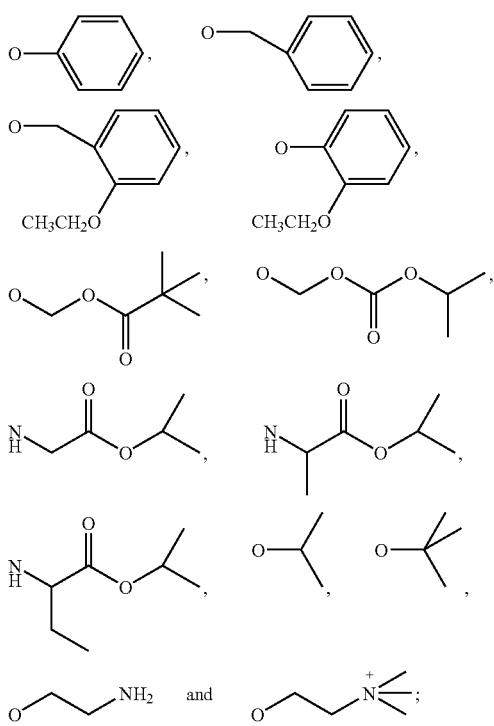

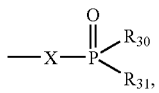

$R_{23}$ and $R_{24}$ are independently selected from the group consisting of H, OH, F, $CO_2H$, $C_1$-$C_3$ alkyl or $PO_3H_2$ or $R_{23}$ together with $R_{24}$ and the carbon to which they are attached form a carbonyl group;

m is 1 or 0; and y is an integer ranging from 0 to 4;

or a pharmaceutically acceptable salt or tautomer thereof. In one embodiment $R_{29}$ is H or F; m is 0; y is 1 or 0; $R_3$ is selected from the group consisting of $C_1$-$C_6$ alkyl and ($C_1$-$C_4$ alkyl)OH; $R_{24}$ and $R_{23}$ are both H. In accordance with one embodiment of the present invention a compound of Formula IV, V or VI is provided wherein $R_{23}$ and $R_{29}$ are both H; m is 0; $R_{25}$ is $CH_2$ or CH; $R_7$ and $R_8$ are independently selected from the group consisting of O, $CH_2$ or CH, NH, and N; $R_3$ is selected from the group consisting of $C_1$-$C_4$ alkyl and ($C_1$-$C_4$ alkyl)OH; $R_{24}$ is selected from the group consisting of H, F, $C_1$-$C_3$ alkyl; and y is 1 or 0. In accordance with one embodiment of the present invention a compound of Formula IV, V or VI is provided wherein $R_{23}$, $R_{24}$ and $R_{29}$ are each H; m is 0; $R_{25}$ is $CH_2$ or CH; $R_7$ and $R_8$ are independently selected from the group consisting of O, $CH_2$ or CH, NH, and N; $R_3$ is selected from the group consisting of $C_1$-$C_4$ alkyl and ($C_1$-$C_4$ alkyl)OH; $R_{15}$ is

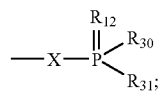

wherein X is O, $CH_2$ CHF or CHOH, $R_{30}$ and $R_{31}$ are independently selected from the group consisting of

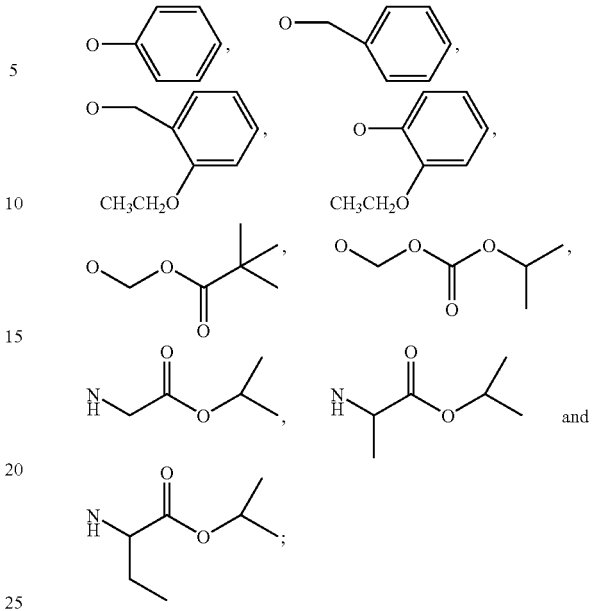

and y is 1 or 0.

In one embodiment of the present invention, a S1P receptor-modulating compound is provided wherein the compound is represented by the formula:

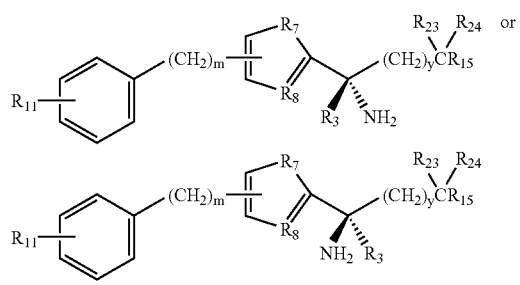

wherein $R_{11}$ is selected from the group consisting of $C_5$-$C_{18}$ alkyl, $C_5$-$C_{18}$ alkenyl and $C_5$-$C_{18}$ alkynyl;

$R_7$ and $R_8$ are independently selected from the group consisting of O, S, NH, and N;

$R_3$ is selected from the group consisting of H, $C_1$-$C_6$ alkyl, ($C_1$-$C_4$ alkyl)OH, and ($C_1$-$C_4$ alkyl)$NH_2$;

$R_{15}$ is

—X—P(=$R_{12}$)($R_{30}$)($R_{31}$);

wherein $R_{12}$ is selected from the group consisting of O and S;

X is selected from the group consisting of O, S, $CH_2$, CHOH, CHF, $CF_2$, and

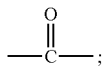

and $R_{30}$ and $R_{31}$ are independently selected from the group consisting of

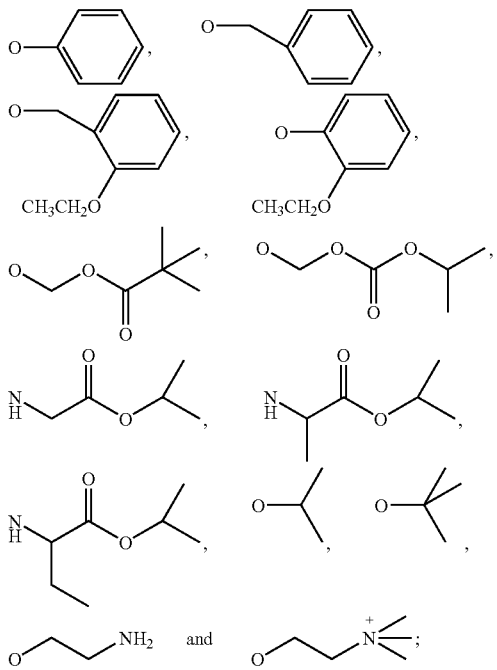

$R_{23}$ is selected from the group consisting of H, F, and OH;
$R_{24}$ is selected from the group consisting of H, F, OH and $PO_3H_2$, or $R_{23}$ together with $R_{24}$ and the carbon to which they are attached form a carbonyl group;
m is 0; and
y is an integer ranging from 0 to 4;
or a pharmaceutically acceptable salt or tautomer thereof.

In one embodiment of the present invention, a S1P receptor-modulating compound is provided wherein the compound is represented by the formula:

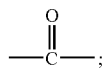

VII wherein $R_{11}$ is selected from the group consisting of $C_5$-$C_{12}$ alkyl, $C_5$-$C_{12}$ alkenyl and $C_5$-$C_{12}$ alkynyl;
$R_7$ and $R_8$ are independently selected from the group consisting of O, S, $CH_2$, CH, NH, and N;
$R_2$ and $R_3$ are independently selected from the group consisting of H, $NH_2$, OH, $C_1$-$C_6$ alkyl, ($C_1$-$C_4$ alkyl)OH, ($C_1$-$C_4$ alkyl)$NH_2$, ($C_1$-$C_4$ alkyl)aryl($C_0$-$C_4$ alkyl) and ($C_1$-$C_4$ alkyl)aryloxyaryl($C_0$-$C_4$ alkyl), with the proviso that $R_2$ and $R_3$ are not the same and either $R_2$ or $R_3$ is $NH_2$;

y is 1 or 0
$R_{15}$ is

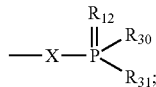

wherein $R_{12}$ is selected from the group consisting of O and S;
X is selected from the group consisting of O, S, $CH_2$, CHOH, CHF, $CF_2$, and

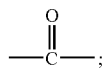

and $R_{30}$ and $R_{31}$ are independently selected from the group consisting of

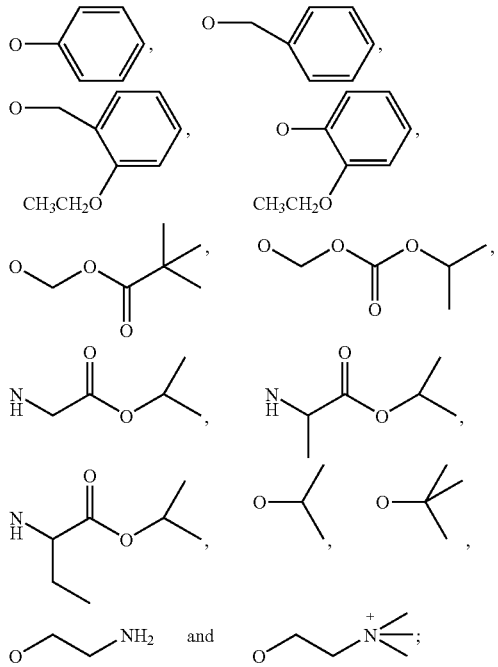

$R_{23}$ is selected from the group consisting of H, F, $CO_2H$, $C_1$-$C_4$ alkyl and OH;
$R_{24}$ is selected from the group consisting of H, F, $C_1$-$C_4$ alkyl and $PO_3H_2$, or $R_{23}$ together with $R_{24}$ and the carbon to which they are attached form a carbonyl group; as well as pharmaceutically acceptable salts or tautomers thereof.

In accordance with one embodiment of the present invention a compound of Formula VII is provided wherein $R_{23}$ is H; $R_{24}$ is selected from the group consisting of H, F, $C_1$-$C_4$ alkyl; and $R_7$ and $R_8$ are independently selected from the group consisting of O, NH and N. In another embodiment, a compound of Formula VII is provided wherein $R_{23}$ is H; $R_2$ is $NH_2$; and $R_3$ is selected from the group consisting of H, $C_1$-$C_4$ alkyl, ($C_1$-$C_4$ alkyl)OH and ($C_1$-$C_4$ alkyl)$NH_2$. Alternatively, in one embodiment a compound of Formula VII is provided wherein $R_{23}$ is H; $R_3$ is $NH_2$; and $R_2$ is selected from the group consisting of H, $C_1$-$C_4$ alkyl, ($C_1$-$C_4$ alkyl)OH and ($C_1$-$C_4$ alkyl)NH$_2$. In another embodiment, a compound of Formula VII is provided wherein R$_{23}$ is H; R$_2$ is NH$_2$; and R$_3$ is selected from the group consisting of H, C$_1$-C$_4$ alkyl, (C$_1$-C$_4$ alkyl)OH and (C$_1$-C$_4$ alkyl)NH$_2$; R$_{24}$ is selected from the group consisting of H, F, C$_1$-C$_4$ alkyl; and R$_7$ and R$_8$ are independently selected from the group consisting of O, NH and N. In another embodiment a compound of Formula VII is provided wherein R$_{11}$ is selected from the group consisting of C$_5$-C$_{12}$ alkyl or C$_5$-C$_{12}$ alkenyl; R$_7$ and R$_8$ are independently selected from the group consisting of O, NH and N; R$_2$ and R$_3$ are independently selected from the group consisting of H, NH$_2$, C$_1$-C$_6$ alkyl and (C$_1$-C$_4$ alkyl)OH, with the proviso that R$_2$ and R$_3$ are not the same and either R$_2$ or R$_3$ is NH$_2$; y is 0; R$_{15}$ is hydroxy; R$_{23}$ is H; and R$_{24}$ is H, F or C$_1$-C$_4$ alkyl; as well as pharmaceutically acceptable salts or tautomers thereof.

In one embodiment of the present invention, a S1P receptor-modulating compound is provided wherein the compound is represented by the formula:

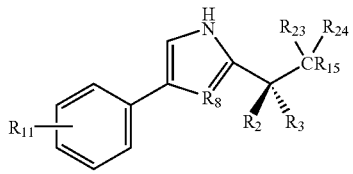

VIII wherein R$_{11}$ is selected from the group consisting of C$_5$-C$_{12}$ alkyl, C$_5$-C$_{12}$ alkenyl and C$_5$-C$_{12}$ alkynyl;

R$_8$ is O or N;

R$_2$ and R$_3$ are independently selected from the group consisting of NH$_2$, C$_1$-C$_6$ alkyl and (C$_1$-C$_4$ alkyl)OH, with the proviso that R$_2$ and R$_3$ are not the same and either R$_2$ or R$_3$ is NH$_2$;

R$_{15}$ is

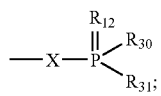

wherein R$_{12}$ is selected from the group consisting of O and S;

X is selected from the group consisting of O, S, CH$_2$, CHOH, CHF, CF$_2$, and

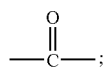

and R$_{30}$ and R$_{31}$ are independently selected from the group consisting of

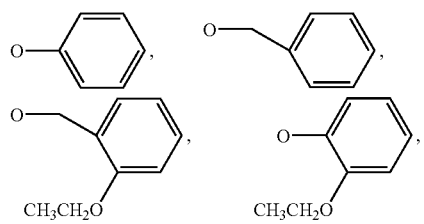

-continued

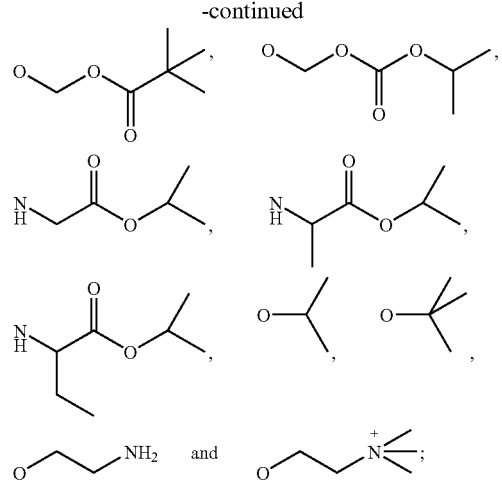

R$_{23}$ is H or F; and

R$_{24}$ is H, F or C$_1$-C$_4$ alkyl; as well as pharmaceutically acceptable salts or tautomers thereof. In one embodiment the compound of Formula VIII is provided wherein R$_{11}$ is C$_5$-C$_{12}$ alkyl or C$_5$-C$_{12}$ alkenyl; R$_8$ is N; R$_2$ and R$_3$ are independently selected from the group consisting of NH$_2$, CH$_3$ and (C$_1$-C$_3$ alkyl)OH, with the proviso that R$_2$ and R$_3$ are not the same and either R$_2$ or R$_3$ is NH$_2$; and R$_{15}$ is hydroxy; R$_{23}$ is H; and R$_{24}$ is H or C$_1$-C$_4$ alkyl as well as pharmaceutically acceptable salts or tautomers thereof. In another embodiment the compound of Formula VIII is provided wherein R$_{11}$ is C$_5$-C$_{12}$ alkyl or C$_5$-C$_{12}$ alkenyl; R$_8$ is N; R$_2$ and R$_3$ are independently selected from the group consisting of NH$_2$, CH$_3$ and (C$_1$-C$_3$ alkyl)OH, with the proviso that R$_2$ and R$_3$ are not the same and either R$_2$ or R$_3$ is NH$_2$; and R$_{15}$ is hydroxy; R$_{23}$ is H; and R$_{24}$ is H or CH$_3$ as well as pharmaceutically acceptable salts or tautomers thereof. In another embodiment the compound of Formula VIII is provided wherein R$_{11}$ is C$_5$-C$_{12}$ alkyl; R$_8$ is N; R$_2$ is NH$_2$; R$_3$ is selected from the group consisting of CH$_3$ and (C$_1$-C$_3$ alkyl)OH; R$_{23}$ and R$_{24}$ are each H; R$_{15}$ is

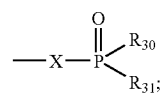

wherein X is selected from the group consisting of O, CH$_2$, CHOH, CHF, CF$_2$, and

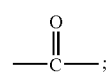

and R$_{30}$ and R$_{31}$ are independently selected from the group consisting of

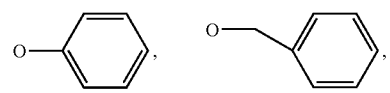

-continued

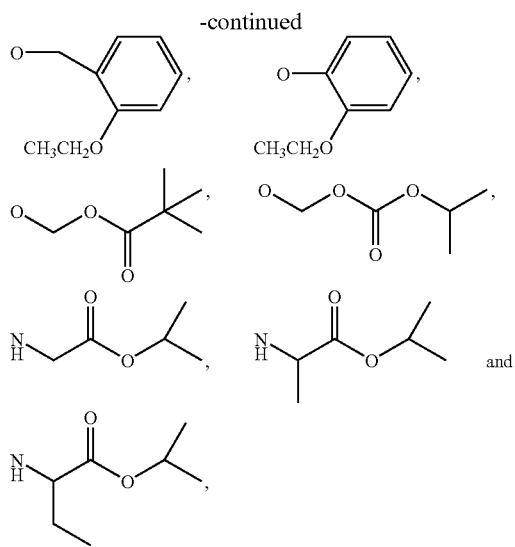

In another embodiment the compound of Formula VIII is provided wherein $R_{11}$ is $C_5$-$C_{12}$ alkyl; $R_8$ is N; $R_2$ is $NH_2$; $R_3$ is selected from the group consisting of $CH_3$ and ($C_1$-$C_3$ alkyl)OH; $R_{23}$ and $R_{24}$ are each H; $R_{15}$ is

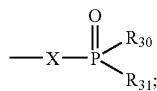

wherein X is selected from the group consisting of $CH_2$, and CHF; and $R_{30}$ and $R_{31}$ are each

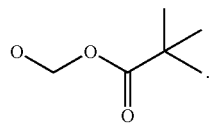

In one embodiment a S1P receptor modulating compound is provided wherein the compound is represented by the formula:

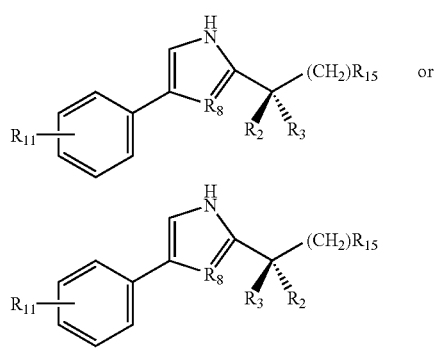

wherein $R_1$ is $C_5$-$C_{18}$ alkyl or $C_5$-$C_{18}$ alkenyl;
$R_8$ is N;
$R_2$ is $NH_2$;
$R_3$ is $CH_3$ or ($C_1$-$C_3$ alkyl)OH and $R_{15}$ is

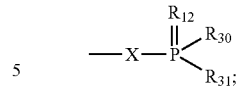

wherein $R_{12}$ is selected from the group consisting of O and S;
X is selected from the group consisting of O, S, $CH_2$, CHOH, CHF, $CF_2$, and

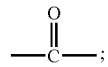

and $R_{30}$ and $R_{31}$ are independently selected from the group consisting of

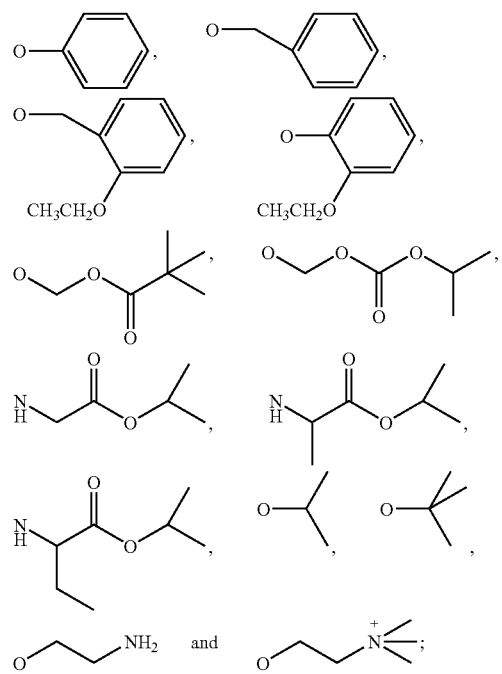

or a pharmaceutically acceptable salt or tautomer thereof.

In one embodiment, an S1P receptor-modulating compound is provided wherein the compound is represented by the structure

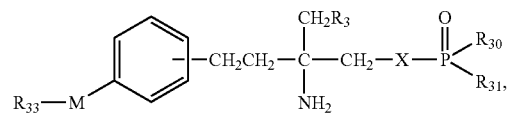

wherein $R_{33}$ is selected from the group consisting of H, $C_1$-$C_{12}$ alkyl, $C_1$-$C_{12}$ alkenyl, $C_1$-$C_{20}$ alkoxy, $C_1$-$C_{20}$ alkylthio, and $C_1$-$C_{20}$ alkylamino;
$R_3$ is selected from the group consisting of H, $NH_2$, OH, $C_1$-$C_6$ alkyl, —($C_1$-$C_4$ alkyl)OH, and —($C_1$-$C_4$ alkyl)$NH_2$
M and X are independently selected from the group consisting of O, S, $CH_2$, CHOH, CHF, $CF_2$, and

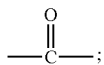

and $R_{30}$ and $R_{31}$ are independently selected from the group consisting of

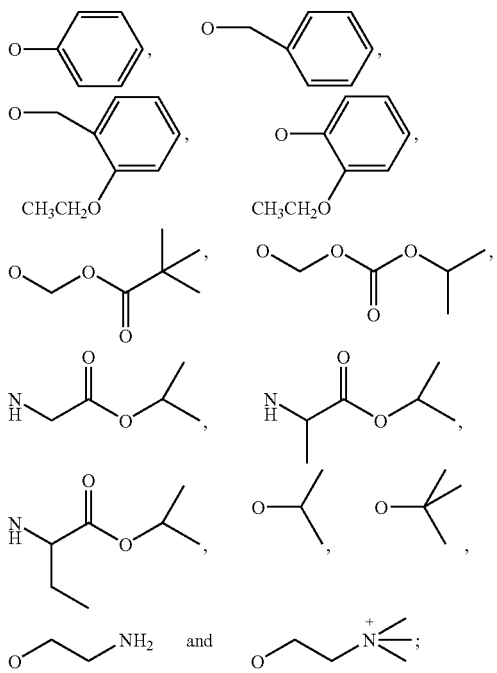

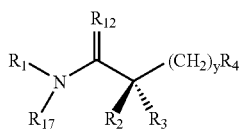

or a pharmaceutically acceptable salt or tautomer thereof.

In accordance with one embodiment, an S1P receptor-modulating compound is provided wherein the compound has the general structure:

XV wherein $R_1$ is selected from the group consisting of $C_5$-$C_{12}$ alkyl, $C_5$-$C_{12}$ alkenyl, $C_5$-$C_{12}$ alkynyl, $C_5$-$C_{12}$ alkoxy, $(CH_2)_p$ $O(CH_2)_q$, $C_1$-$C_8$ alkyl($C_5$-$C_{10}$ aryl)$R_{20}$, $C_1$-$C_8$ alkyl($C_5$-$C_{10}$ heteroaryl)$R_{20}$, $C_1$-$C_8$ alkyl($C_5$-$C_{10}$ cycloalkyl)$R_{20}$, $C_1$-$C_{10}$ alkoxy($C_5$-$C_{10}$ aryl)$R_{20}$, $C_1$-$C_{10}$ alkoxy($C_5$-$C_{10}$ heteroaryl)$R_{20}$ and $C_1$-$C_{10}$ alkoxy($C_5$-$C_{10}$ cycloalkyl)$R_{20}$;

$R_{12}$ is O, or $R_1$ and $R_{12}$ taken together form an optionally substituted heteroaryl;

$R_{17}$ is H, $C_1$-$C_4$ alkyl or $(CH_2)(C_5$-$C_6)$aryl;

$R_2$ and $R_3$ are independently selected from the group consisting of H, $NH_2$, OH, $C_1$-$C_6$ alkyl, —($C_1$-$C_4$ alkyl)OH, and —($C_1$-$C_4$ alkyl)$NH_2$; y is an integer from 1-10, and $R_4$ is selected from the group consisting of hydroxyl, phosphate esters, methylene phosphonate esters, α-substituted methylene phosphonate esters, phosphate analog esters and phosphonate analog esters or a pharmaceutically acceptable salt thereof. In one embodiment $R_4$ is represented by the formula

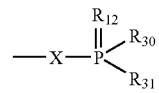

wherein $R_{12}$ is selected from the group consisting of O, NH, and S;

X is selected from the group consisting of O, NH, S, $CH_2$, CHOH, CHF, $CF_2$, and

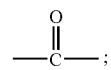

and $R_{30}$ and $R_{31}$ are independently selected from the group consisting of $C_1$-$C_2$ alkoxy, hydrogen, hydroxy,

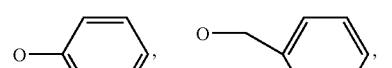

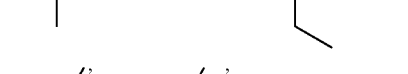

In one embodiment, one of the $R_2$ and $R_3$ substituents of Formula XV is $NH_2$. Examples of pharmaceutically acceptable salts of the compounds of the Formula XV include salts with inorganic acids, such as hydrochloride, hydrobromide and sulfate, salts with organic acids, such as acetate, fumarate, maleate, benzoate, citrate, malate, methanesulfonate and benzenesulfonate salts, and when a carboxy group is present, salts with metals such as sodium, potassium, calcium and aluminum, salts with amines, such as triethylamine and salts with dibasic amino acids, such as lysine. The compounds and salts of the present invention encompass hydrate and solvate forms.

In one embodiment, an S1P modulating compound is provided having the general structure:

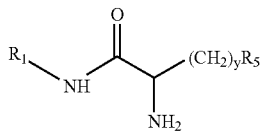

wherein $R_1$ is selected from the group consisting of $C_8$-$C_{22}$ alkyl, $C_8$-$C_{22}$ alkenyl, $C_8$-$C_{22}$ alkynyl and —$(CH_2)_n$—Z—$R_6$;

$R_5$ is represented by the formula

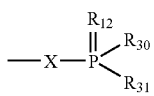

wherein $R_{12}$ is selected from the group consisting of O, NH and S;

X is selected from the group consisting of O, NH, S, $CH_2$, CHOH, $CO_2H$, $PO_3H_2$, CHF, $CF_2$, and

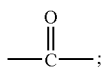

and $R_{30}$ and $R_{31}$ are independently selected from the group consisting of $C_1$-$C_2$ alkoxy, hydrogen, hydroxy,

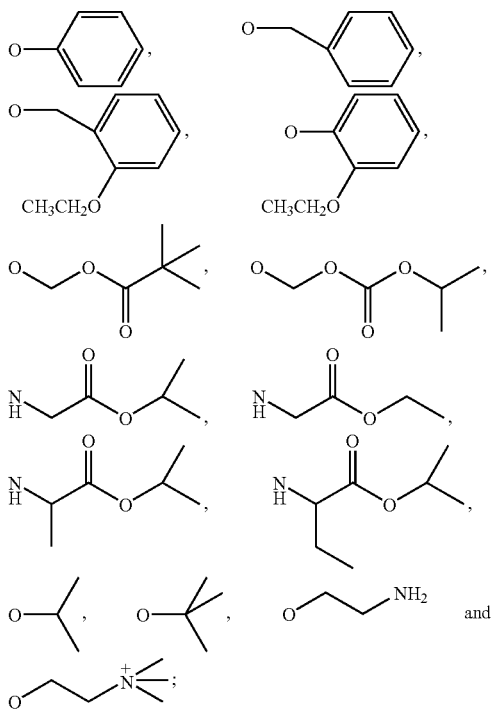

y is an integer ranging from 1 to 4;
n is an integer ranging from 0 to 10;

Z is selected from the group consisting of $C_5$-$C_{10}$ cycloalkyl, $C_5$-$C_{10}$ aryl and $C_5$-$C_{10}$ heteroaryl; and $R_6$ is selected from the group consisting of H, $C_1$-$C_2$ alkyl, $C_1$-$C_{20}$ alkoxy, $C_1$-$C_{20}$ alkylthio, and $C_1$-$C_{20}$ alkylamino or a pharmaceutically acceptable salt thereof. When $R_5$ is an alpha substituted phosphonate ester, the alpha carbon can be mono- or di-substituted, wherein the substitutions are independently selected from the group consisting of H, OH, F, $CO_2H$, $PO_3H_2$, or together with the attached carbon, form a carbonyl. In one embodiment, $R_1$ is $C_8$-$C_{22}$ alkyl, and more preferably $C_{12}$-$C_{16}$ alkyl, y is 1 or 2 and $R_5$ is hydroxy, phosphate or phosphonate. Alternatively, in one embodiment, $R_1$ is —$(CH_2)_n$—Z—$R_6$, wherein n is an integer ranging from 14, Z is $C_5$-$C_6$ aryl and $R_6$ is $C_1$-$C_{10}$ alkyl; more preferably, Z is phenyl, $R_5$ is a phosphate ester, a phosphonate ester or an alpha substituted phosphonate ester, and $R_6$ is $C_6$-$C_{10}$ alkyl.

The present invention also encompasses compounds of the general structure:

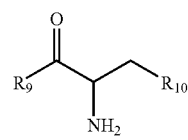

wherein $R_9$ is selected from the group consisting of —$NR_1$, and —$OR_1$;

$R_1$ is selected from the group consisting of $C_8$-$C_{22}$ alkyl and

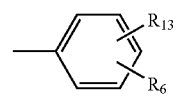

wherein $R_6$ and $R_{13}$ are independently selected from the group consisting of H, $C_1$-$C_{10}$ alkyl and $C_1$-$C_{20}$ alkoxy and $R_{10}$ is represented by the formula

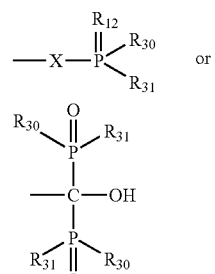

wherein X is selected from the group consisting of O, NH, S, $CH_2$, CHOH, $CO_2H$, CHF, $CF_2$, and

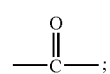

and $R_{30}$ and $R_{31}$ are independently selected from the group consisting of $C_1$-$C_2$ alkoxy, hydrogen, hydroxy,

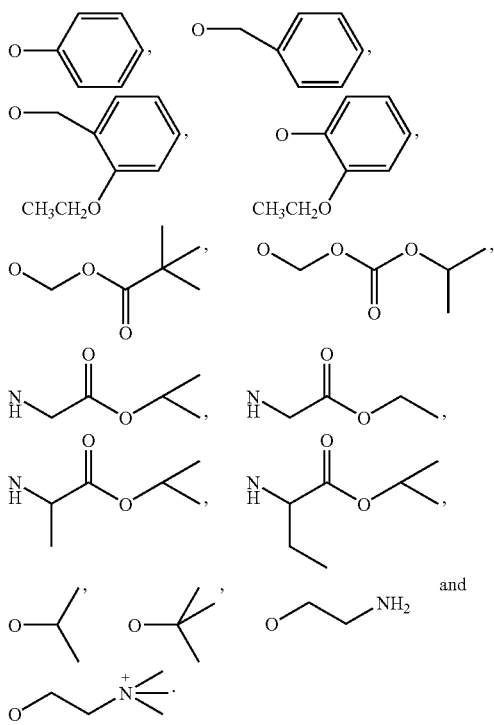

In one embodiment, $R_9$ is $-NR_1$, $R_6$ is $C_1$-$C_{10}$ alkyl, $R_{13}$ is H and $R_{10}$ represented by the formula

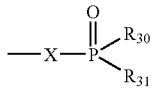

wherein X is selected from the group consisting of O, $CH_2$, CHOH, CHF, $CF_2$, and

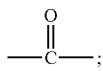

and $R_{30}$ and $R_{31}$ are independently selected from the group consisting of

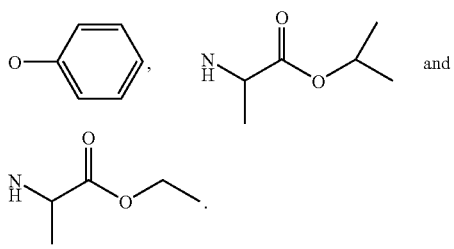

A GTP[γ35 S] binding assay was developed to analyze directly the activation of individual S1P receptors, and thus allow the identification of S1P receptor agonists and antagonists as well as determine the relative efficacies and potencies at each receptor in a common system. The same results were obtained regardless of whether the recombinant receptor used exogenous G proteins (HEK293T cells) or endogenous G proteins (RH7777 cells). In addition, insect Sf9 cells infected with recombinant baculovirus encoding receptors (e.g. LPA and S1P receptors) and G proteins can also serve as the source of membranes for the broken cells used in the GTPgammaS-35 binding assays. The Sf9 cell and HEK293T cell membranes gave similar results. Furthermore, the activities measured in the broken cell assay predicted the responses seen in whole cell assays. Thus, the primary assay used in the present invention for determining compound potency and efficacy is a valid measure of activity at the S1P receptors.

The GTP[γ35 S] binding assay has revealed that the compounds of the present invention have the ability to modulate S1P receptor activity (See Examples 2 and 3). More particularly, compounds represented by the following formula display activity as modulators of S1P activity. More particularly, such compounds include those having the structure

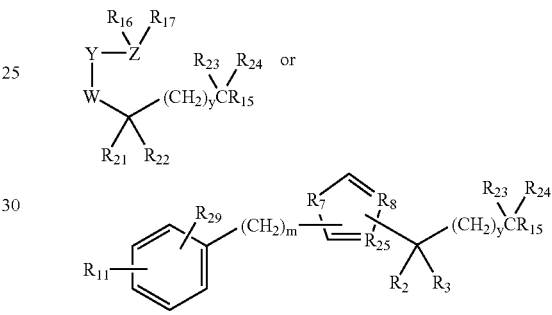

wherein
W is $CR_{27}R_{28}$ or $(CH_2)_n NH(CO)$;
  wherein $R_{27}$ and $R_{28}$ are independently selected from the group consisting of H, halo and hydroxy;
Y is selected from the group consisting of a bond, $CR_9R_{10}$, carbonyl, NH, O or S;
  wherein $R_9$ and $R_{10}$ are independently selected from the group consisting of H, halo, hydroxy and amino;
Z is $CH_2$, aryl, halo substituted aryl or heteroaryl;
$R_{11}$ and $R_{16}$ are independently selected from the group consisting of $C_5$-$C_{12}$ alkyl, $C_5$-$C_{12}$ alkenyl, $C_5$-$C_{12}$ alkynyl, $C_5$-$C_{12}$ alkoxy, $(CH_2)_pO(CH_2)_q$, $C_1$-$C_8$ alkyl($C_5$-$C_{10}$ aryl)$R_{20}$, $C_1$-$C_8$ alkyl($C_5$-$C_{10}$ heteroaryl)$R_{20}$, $C_1$-$C_8$ alkyl($C_5$-$C_{10}$ cycloalkyl)$R_{20}$, $C_1$-$C_{10}$ alkoxy($C_5$-$C_{10}$ aryl)$R_{20}$, $C_1$-$C_{10}$ alkoxy($C_5$-$C_{10}$ heteroaryl)$R_{20}$ and $C_1$-$C_{10}$ alkoxy($C_5$-$C_{10}$ cycloalkyl)$R_{20}$;
  wherein $R_{20}$ is H or $C_1$-$C_{10}$ alkyl;
$R_{29}$ is H or halo;
$R_{17}$ is selected from the group consisting of H, halo, $NH_2$, $C_1$-$C_6$ alkyl, $C_1$-$C_6$ alkoxy, $C_1$-$C_6$ alkylamino, $C_1$-$C_6$ alkylcyano and $C_1$-$C_6$ alkylthio;
$R_2$ and $R_{21}$ are both $NH_2$;
$R_3$ is selected from the group consisting of H, $C_1$-$C_6$ alkyl, ($C_1$-$C_4$ alkyl)OH, and ($C_1$-$C_4$ alkyl)$NH_2$;
$R_{22}$ is selected from the group consisting of $C_1$-$C_6$ alkyl, ($C_1$-$C_4$ alkyl)OH and ($C_1$-$C_4$ alkyl)$NH_2$;
$R_{23}$ is selected from the group consisting of H, F, $CO_2H$, OH, $C_1$-$C_6$ alkyl, ($C_1$-$C_4$ alkyl)OH, and ($C_1$-$C_4$ alkyl)$NH_2$;
$R_{24}$ is selected from the group consisting of H, F and $PO_3H_2$, or $R_{23}$ together with $R_{24}$ and the carbon to which they are attached form a carbonyl group;

$R_{25}$, $R_7$ and $R_8$ are independently selected from the group consisting of O, S, $CHR_{26}$, $CHR_{26}$, $NR_{26}$, and N;

wherein $R_{26}$ is H, F or $C_1$-$C_4$ alkyl;

$R_{15}$ is represented by the formula

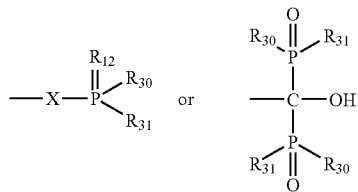

wherein X is selected from the group consisting of O, NH, S, $CH_2$, CHOH, $CO_2H$, CHF, $CF_2$, and

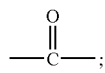

and $R_{30}$ and $R_{31}$ are independently selected from the group consisting of $C_1$-$C_2$ alkoxy, hydrogen, hydroxy,

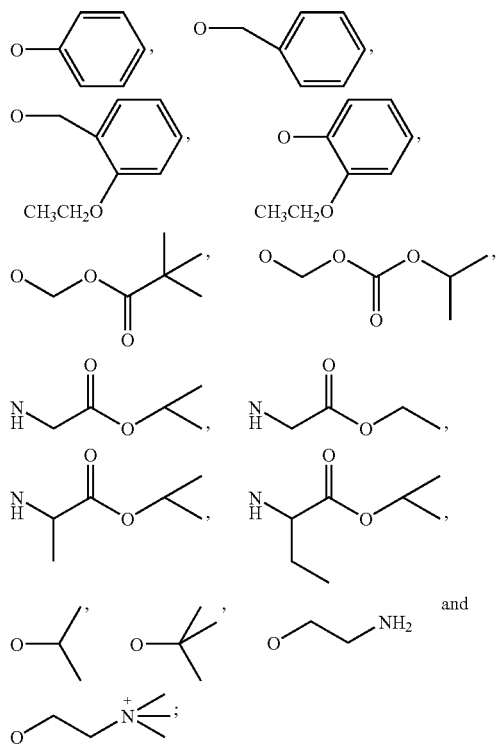

y and m are integers independently ranging from 0 to 4;

p and q are integers independently ranging from 1 to 10;

n is an integer ranging from 0 to 10;

or a pharmaceutically acceptable salt or tautomer thereof, with the proviso that W and Y are not both methylene.

As described in Example 2 compounds having the general structure

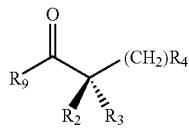

wherein $R_9$ is selected from the group consisting of —$NR_1$, and —$OR_1$, $R_1$ is $C_8$-$C_{22}$ alkyl, $R_2$ and $R_3$ are independently selected from the group consisting of H and $NH_2$, wherein at least one of $R_2$ and $R_3$ is $NH_2$ and $R_4$ is phosphate all display significant agonist activity at the S1P receptors tested (S1P1, S1P2, S1P3, S1P5), although none were as potent as S1P itself (See Table 1 of Example 2). However, one compound, VPC22135 (wherein $R_2$ is H, $R_3$ is $NH_2$, $R_4$ is phosphate and $R_9$ is —$N(CH_2)_{13}CH_3$), approached the potency of S1P at both the human S1P1 and Human S1P3 receptors. In accordance with one embodiment of the present invention, a phosphate or phosphonate ester derivative of compound VPC22135 is used as a selective agonist of human S1P1 and human S1P3 receptors. The phosphate and phosphonate esters of VPC22135 are anticipated to have enhanced oral availability relative to the parent compound and thus be more suited to an orally administered pharmaceutical formulation. Curiously, this compound has the amino group in the unnatural (R) configuration. Its enantiomer, VPC22053, was more than 1 log order less potent at both the S1P1 and S1P3 receptors.

An additional series of compounds have shown activity in modulating S1P receptor activity, however these compounds also displayed selectivity for certain S1P receptor subtypes (See Examples 1 and 3 and FIGS. 1-5). Each of these compounds (VPC 23019, 23031, 23065, 23069, 23087, 23089, 23075, 23079) are inactive at the S1P2 receptor. Furthermore, in accordance with the present invention, phosphate, phosphonate, and alpha substituted phosphonate ester derivatives of each of these compounds can be prepared and used in accordance with the present invention. Compounds VPC23031, 23019, 23089 are inverse agonists (antagonists of the S1P3) receptor, but this inverse agonism becomes agonism when the alkyl chain length is 9 carbons (VPC23079) or 10 (VPC23069). In accordance with one embodiment of the present invention, an antagonist of S1P activity is provided. In particular, a compound having the general structure:

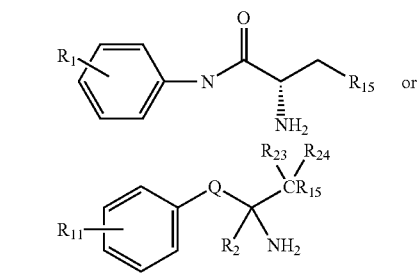

wherein $R_1$ and $R_{11}$ is $C_4$-$C_{12}$ alkyl and located in the meta or ortho position, Q is selected from the group consisting of $C_5$-$C_6$ optionally substituted cycloalkyl, $C_5$-$C_6$ optionally substituted heterocyclic, $C_5$-$C_6$ optionally substituted aryl and $C_5$-$C_6$ optionally substituted heteroaryl;

$R_2$ is selected from the group consisting of H, $C_1$-$C_4$ alkyl and ($C_1$-$C_4$ alkyl)OH;

$R_{23}$ is selected from the group consisting of H, F, $CO_2H$, OH, $C_1$-$C_6$ alkyl, ($C_1$-$C_4$ alkyl)OH, and ($C_1$-$C_4$ alkyl)$NH_2$;

$R_{24}$ is selected from the group consisting of H, F and $PO_3H_2$, or $R_{23}$ together with $R_{24}$ and the carbon to which they are attached form a carbonyl group; and $R_{15}$ is represented by the formula

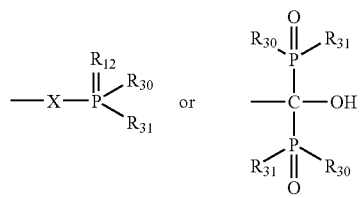

wherein X is selected from the group consisting of O, NH, S, $CH_2$, CHOH, $CO_2H$, CHF, $CF_2$, and

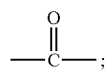

and $R_{30}$ and $R_{31}$ are independently selected from the group consisting of $C_1$-$C_2$ alkoxy, hydrogen, hydroxy,

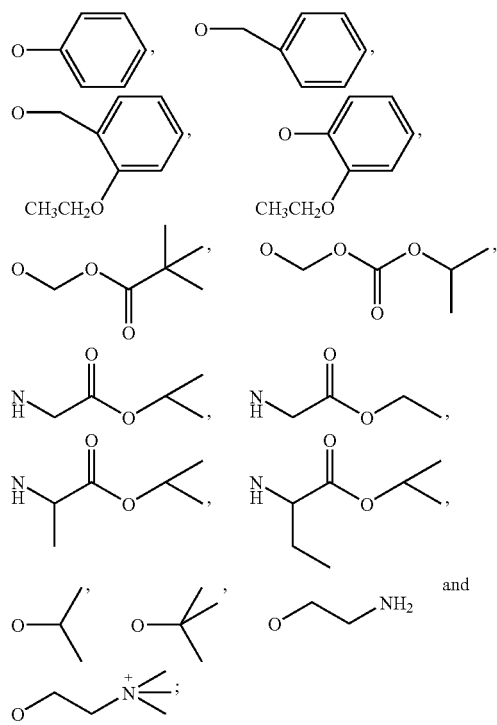

or a pharmaceutically acceptable salt or tautomer thereof are anticipated to have antagonist activity at the S1P3 receptor. In accordance with one embodiment $R_{15}$ is represented by the formula

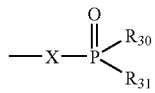

wherein X is selected from the group consisting of O, S, $CH_2$, CHOH and CHF; and $R_{30}$ and $R_{31}$ are independently selected from the group consisting of

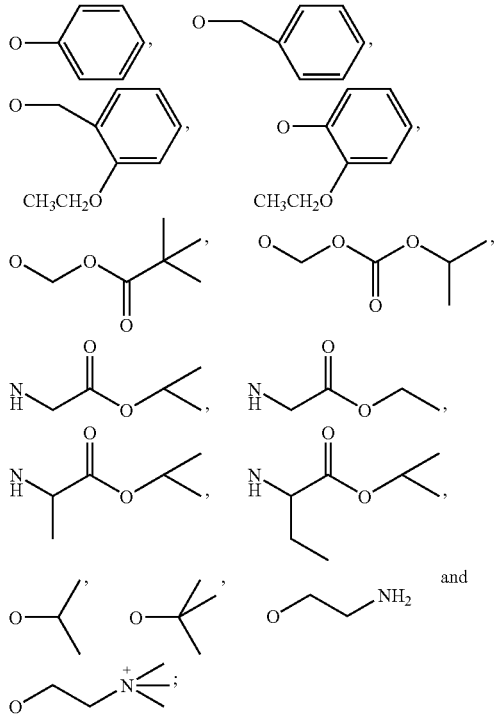

wherein the $R_1$ substituent is located in the ortho position on the phenyl ring, and in one embodiment the $R_1$ substituent is located in the meta position on the phenyl ring.

In one embodiment an S1P modulating compound is provided represented by the general formula:

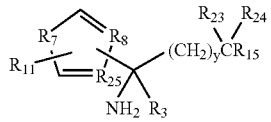

XI wherein $R_{11}$ is independently selected from the group consisting of $C_5$-$C_{12}$ alkyl, $C_5$-$C_{12}$ alkenyl, $C_5$-$C_{12}$ alkynyl, $C_5$-$C_{12}$ alkoxy, $(CH_2)_pO(CH_2)_q$, ($C_5$-$C_{10}$ aryl)$R_{40}$, ($C_5$-$C_{10}$ heteroaryl)$R_{40}$, ($C_5$-$C_{10}$ cycloalkyl)$R_{40}$;

wherein $R_{40}$ is selected from the group consisting of H, $C_1$-$C_{12}$ alkyl, $C_2$-$C_{12}$ alkenyl, ($C_5$-$C_{10}$ cycloalkyl)$R_{20}$, $C_1$-$C_{10}$ alkoxy($C_5$-$C_{10}$ aryl)$R_{20}$, $C_1$-$C_{10}$ alkoxy($C_5$-$C_{10}$ heteroaryl)$R_{20}$ and $C_1$-$C_{10}$ alkoxy($C_5$-$C_{10}$ cycloalkyl)$R_{20}$;

wherein $R_{20}$ is H or $C_1$-$C_{10}$ alkyl;

$R_{25}$, $R_7$ and $R_8$ are independently selected from the group consisting of O, S, $CHR_{26}$, $CHR_{26}$, $NR_{26}$, and N;

wherein $R_{26}$ is H, F or $C_1$-$C_4$ alkyl;

$R_3$ is selected from the group consisting of $C_1$-$C_6$ alkyl and ($C_1$-$C_4$ alkyl)OH;

$R_{15}$ is represented by the formula

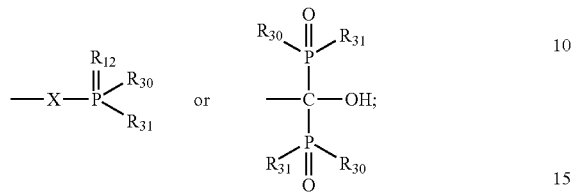

wherein $R_{12}$ is selected from the group consisting of O, NH and S;

X is selected from the group consisting of O, NH, S, $CH_2$, CHOH, CHF, $CF_2$, and

and $R_{30}$ and $R_{31}$ are independently selected from the group consisting of $C_1$-$C_2$ alkoxy,

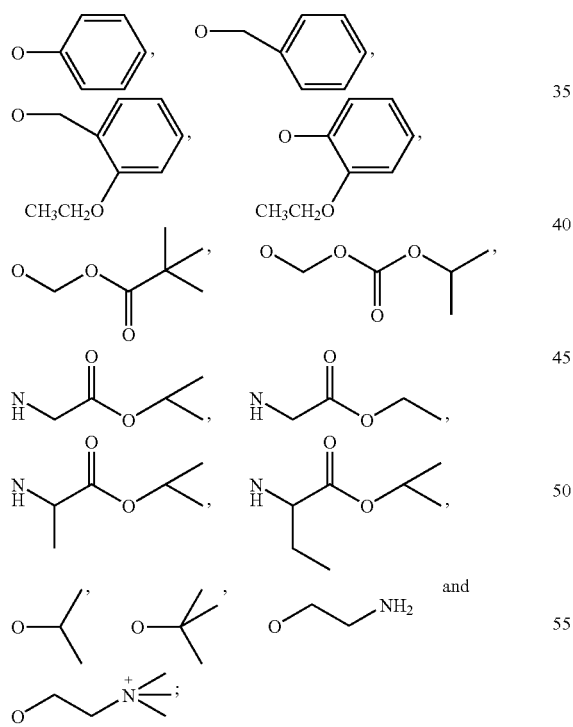

y is an integer ranging from 0 to 4;

p and q are integers independently ranging from 1 to 10;

or a pharmaceutically acceptable salt or tautomer thereof.

In one embodiment the compound of Formula XI is provided wherein y is 0; $R_3$ is selected from the group consisting of $C_1$-$C_3$ alkyl and ($C_1$-$C_3$ alkyl)OH; $R_{25}$ is CH, $R_7$ is NH; $R_8$ is N; and $R_{15}$ is represented by the formula

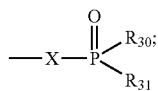

wherein X is selected from the group consisting of O, $CH_2$, CHOH, CHF, $CF_2$, and

In accordance with one embodiment $R_{25}$ is —CH—, $R_7$ is NH, $R_8$ is N, y is 0, $R_{23}$ and $R_{24}$ are each H, $R_{15}$ is represented by the formula

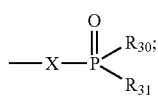

wherein X is selected from the group consisting of $CH_2$, CHOH, CHF, $CF_2$, and

and $R_{30}$ and $R_{31}$ are the same and selected from the group consisting of

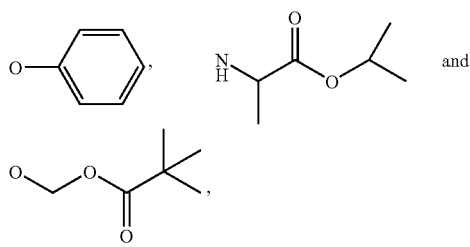

and in another embodiment $R_{30}$ and $R_{31}$ are both

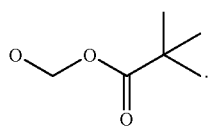

In accordance with one embodiment an S1P modulating compound is provided having the general structure

XII

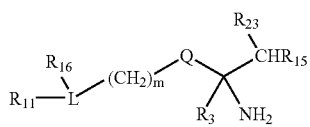

wherein $R_{11}$ is selected from the group consisting of $C_5$-$C_{18}$ alkyl, $C_5$-$C_{18}$ alkenyl, $C_5$-$C_{18}$ alkynyl, $C_5$-$C_{18}$ alkoxy, $(CH_2)_pO(CH_2)_q$, $C_1$-$C_{10}$ alkyl($C_5$-$C_6$ aryl)$R_{20}$, $C_1$-$C_{10}$ alkyl($C_5$-$C_6$ heteroaryl)$R_{20}$, $C_1$-$C_{10}$ alkyl($C_5$-$C_6$ cycloalkyl)$R_{20}$, $C_1$-$C_{10}$ alkoxy($C_5$-$C_6$ aryl)$R_{20}$, $C_1$-$C_{10}$ alkoxy($C_5$-$C_6$ heteroaryl)$R_{20}$ and $C_1$-$C_{10}$ alkoxy($C_5$-$C_6$ cycloalkyl)$R_{20}$;

wherein $R_{20}$ is H or $C_1$-$C_{10}$ alkyl;

p and q are integers independently ranging from 1 to 10;

$R_{16}$ is selected from the group consisting of H, $C_1$-$C_{18}$ alkyl, $C_2$-$C_{18}$ alkenyl, $C_2$-$C_{18}$ alkynyl, $C_1$-$C_{18}$ alkoxy, $(CH_2)_pO(CH_2)_q$ and $(CH_2)_pNH(CH_2)_q$;

Q is

wherein $R_{25}$, $R_7$ and $R_8$ are independently selected from the group consisting of O, S, $CR_{26}$, $CHR_{26}$, $NR_{26}$, and N, $R_{26}$ is H, F or $C_1$-$C_4$ alkyl, and m is an integer ranging from 0-4;

L is selected from the group consisting of a bond, $C_5$-$C_8$ aryl and $C_5$-$C_8$ heteroaryl;

$R_3$ is selected from the group consisting of $C_1$-$C_4$ alkyl and ($C_1$-$C_4$ alkyl)OH;

$R_{23}$ is H, F or $C_1$-$C_4$ alkyl, and $R_{15}$ is represented by the structure

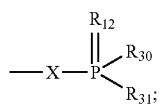

wherein $R_{12}$ is selected from the group consisting of O and S;

X is selected from the group consisting of O, S, $CH_2$, CHOH, CHF, $CF_2$, and

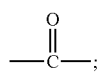

$R_{30}$ and $R_{31}$ are independently selected from the group consisting of $C_1$-$C_2$ alkoxy,

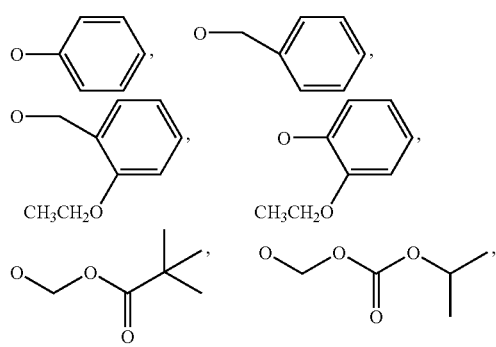

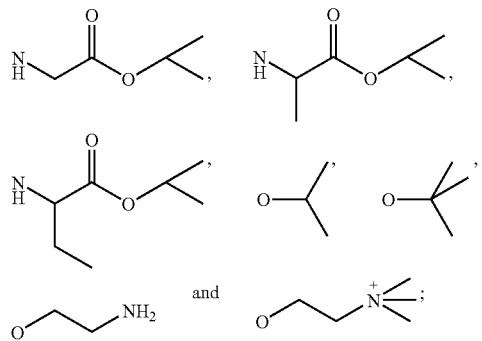

or a pharmaceutically acceptable salt or tautomer thereof.

In accordance with one embodiment a compound of Formula XII is provided wherein Q is

L is selected from the group consisting of —CH—,

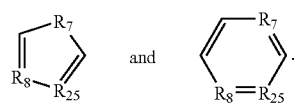

In another embodiment,

Q is selected from the group consisting of

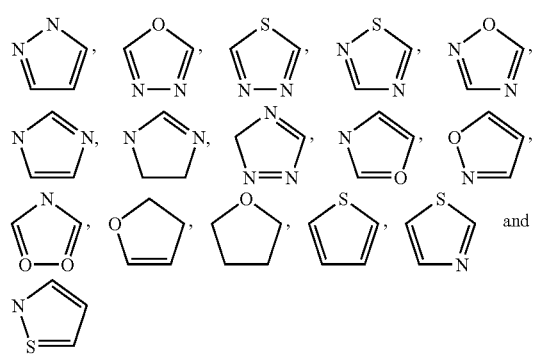

L is selected from the group consisting of

m is 0; and $R_{23}$ is H or F, and in a further embodiment Q is selected from the group consisting of

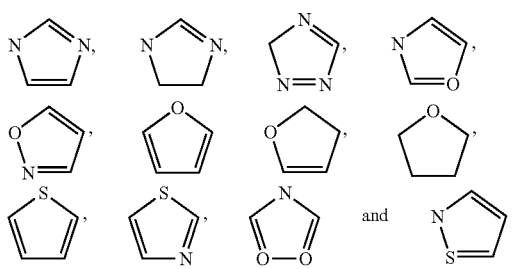

In accordance with one embodiment the compound is represented by the formula:

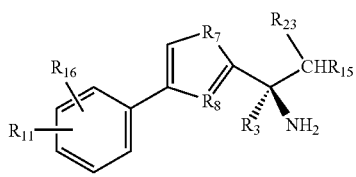
XIII wherein $R_{11}$ is selected from the group consisting of $C_5$-$C_{18}$ alkyl, $C_5$-$C_{18}$ alkenyl, $C_5$-$C_{18}$ alkynyl, $C_5$-$C_{18}$ alkoxy and $(CH_2)_pO(CH_2)_q$;

wherein p and q are integers independently ranging from 1 to 10; and $R_{16}$ is selected from the group consisting of H, $C_1$-$C_{10}$ alkyl, $C_2$-$C_{10}$ alkenyl and $C_2$-$C_{10}$ alkynyl;

$R_7$ and $R_8$ are independently selected from the group consisting of O, S, $CR_{26}$, $CHR_{26}$, $NR_{26}$, and N, $R_3$ is $C_1$-$C_4$ alkyl or ($C_1$-$C_4$ alkyl)OH, $R_{23}$ is H or F;

$R_{15}$ is represented by the formula

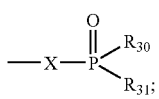

wherein X is selected from the group consisting of O, $CH_2$, CHOH, CHF, $CF_2$, and

and $R_{30}$ and $R_{31}$ are independently selected from the group consisting of

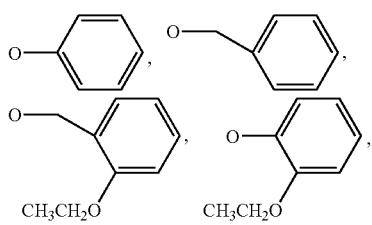

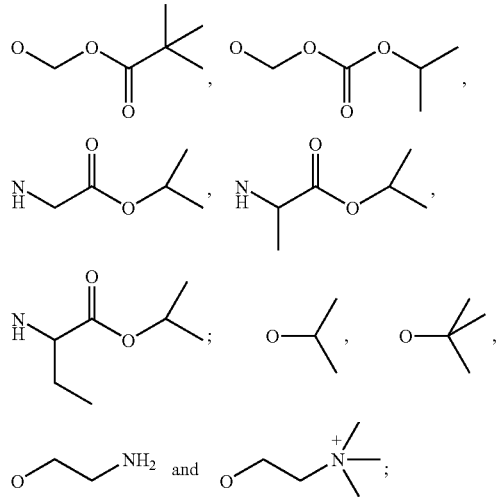

or a pharmaceutically acceptable salt or tautomer thereof. In one embodiment a compound of Formula XIII is provided wherein $R_{11}$ is selected from the group consisting of $C_5$-$C_{18}$ alkyl, $C_5$-$C_{18}$ alkenyl, $C_5$-$C_{18}$ alkynyl, $C_5$-$C_{18}$ alkoxy and $(CH_2)_pO(CH_2)_q$;

wherein p and q are integers independently ranging from 1 to 10; and $R_{16}$ and $R_{23}$ are both H; $R_7$ is NH; $R_8$ is N;

$R_3$ is $C_1$-$C_4$ alkyl or ($C_1$-$C_4$ alkyl)OH;

$R_{15}$ is represented by the formula

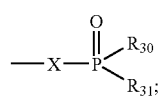

wherein X is selected from the group consisting of O, $CH_2$ and CHF and $R_{30}$ and $R_{31}$ are the same and are selected from the group consisting of

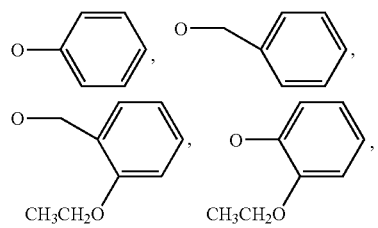

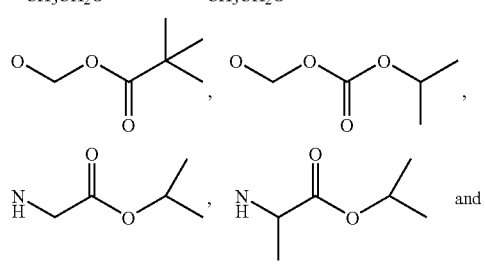

-continued

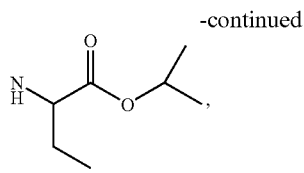

or a pharmaceutically acceptable salt or tautomer thereof. In another embodiment a compound of Formula XIII is provided wherein $R_{11}$ is selected from the group consisting of $C_5$-$C_{18}$ alkyl and $C_5$-$C_{18}$ alkenyl; $R_{16}$ and $R_{23}$ are both H; $R_7$ is NH; $R_8$ is N; $R_3$ is $C_1$-$C_2$ alkyl; and $R_{15}$ is represented by the formula

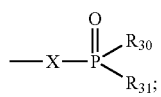

wherein X is selected from the group consisting of $CH_2$ and CHF; and $R_{30}$ and $R_{31}$ are independently selected from the group consisting of

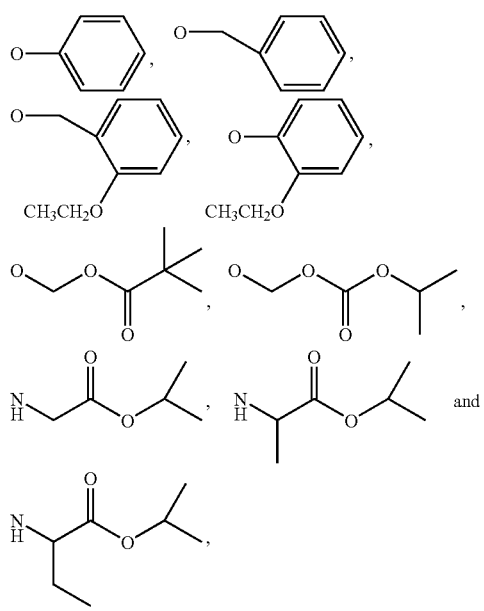

or a pharmaceutically acceptable salt or tautomer thereof. In another embodiment a compound of Formula XIII is provided wherein $R_{11}$ is selected from the group consisting of $C_5$-$C_{18}$ alkyl and $C_5$-$C_{18}$ alkenyl; $R_{16}$ and $R_{23}$ are both H; $R_7$ is NH; $R_8$ is N; $R_3$ is $C_1$-$C_2$ alkyl; and $R_{15}$ is represented by the formula

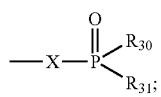

wherein X is selected from the group consisting of $CH_2$ and CHF; and $R_{30}$ and $R_{31}$ are each or a pharmaceutically acceptable salt or tautomer thereof.

In accordance with one embodiment an S1P modulating compound is provided represented by the formula:

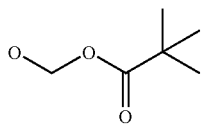

wherein $R_{11}$ is selected from the group consisting of $C_5$-$C_{18}$ alkyl and $C_5$-$C_{18}$ alkenyl;

$R_3$ is $CH_3$; and $R_{16}$ is selected from the group consisting of H, and $C_1$-$C_4$ alkyl;

$R_{15}$ is represented by the formula

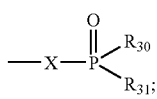

wherein X is selected from the group consisting of O, $CH_2$ and CHF; and $R_{30}$ and $R_{31}$ are independently selected from the group consisting of

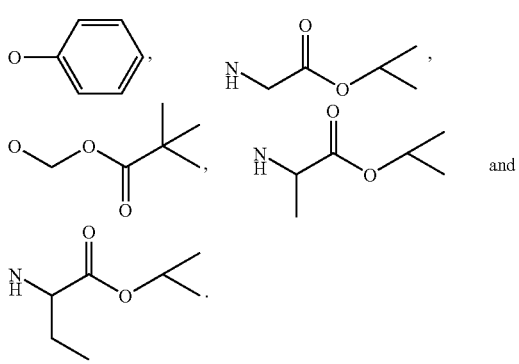

Compounds of the general structure:

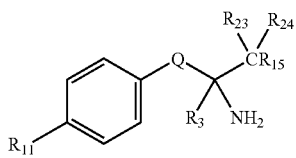

XIV (wherein $R_{11}$ is located in the para position) have exhibited activity as agonists of S1P activity. In particular, compounds of Formula XIII and XIV are provided as S1P agonists wherein $R_{11}$ is $C_5$-$C_{18}$ alkyl or $C_5$-$C_{18}$ alkenyl. In one embodiment a compound of Formula XIV is provided wherein $R_{11}$ is $C_5$-$C_{18}$ alkyl or $C_5$-$C_{18}$ alkenyl Q is selected from the group consisting of $C_5$-$C_6$ optionally substituted cycloalkyl, $C_5$-$C_6$ optionally substituted heterocyclic, $C_5$-$C_6$ optionally substituted aryl and $C_5$-$C_6$ optionally substituted heteroaryl;

$R_3$ is selected from the group consisting of H, $C_1$-$C_4$ alkyl and ($C_1$-$C_4$ alkyl)OH;

$R_{23}$ is selected from the group consisting of H, F, $CO_2H$, OH, $C_1$-$C_6$ alkyl, ($C_1$-$C_4$ alkyl)OH, and ($C_1$-$C_4$ alkyl)$NH_2$;

$R_{24}$ is selected from the group consisting of H, F and $PO_3H_2$, or $R_{23}$ together with $R_{24}$ and the carbon to which they are attached form a carbonyl group; and $R_{15}$ is represented by the formula

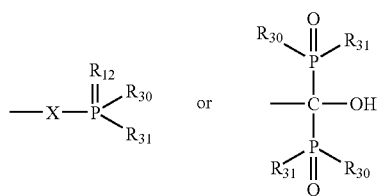

wherein $R_{12}$ is O or S;

X is selected from the group consisting of O, NH, S, $CH_2$, CHOH, $CO_2H$, CHF, $CF_2$, and

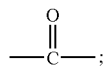

and $R_{30}$ and $R_{31}$ are independently selected from the group consisting of $C_1$-$C_2$ alkoxy, hydrogen, hydroxy,

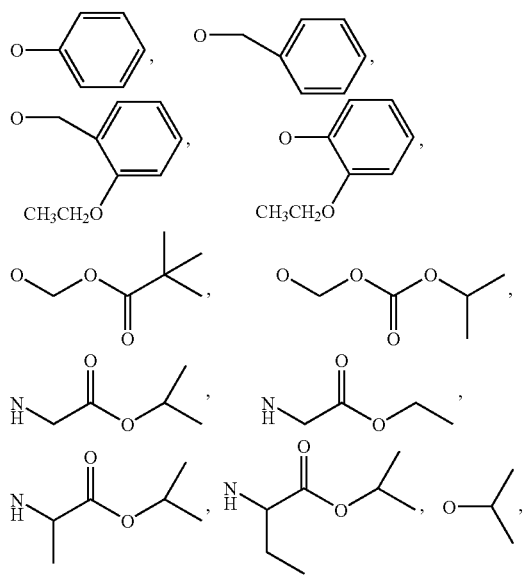

-continued

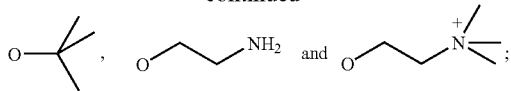

or a pharmaceutically acceptable salt or tautomer thereof and a pharmaceutically acceptable carrier. In one embodiment a compound represented by Formula XIV is provided as an S1P agonist wherein $R_{11}$ is $C_5$-$C_{18}$ alkyl or $C_5$-$C_{18}$ alkenyl;

Q is selected from the group consisting of —NH(CO)—,

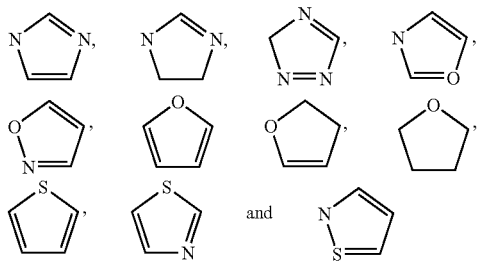

$R_2$ is selected from the group consisting of H, $C_1$-$C_4$ alkyl and ($C_1$-$C_4$ alkyl)OH;

$R_{24}$ is H;

$R_{23}$ is H or $C_1$-$C_4$ alkyl, and $R_{15}$ is represented by the formula

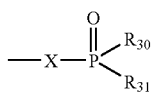

wherein X is selected from the group consisting of O, S, $CH_2$, CHOH, CHF, $CF_2$, and

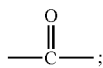

and $R_{30}$ and $R_{31}$ are independently selected from the group consisting of $C_1$-$C_2$ alkoxy,

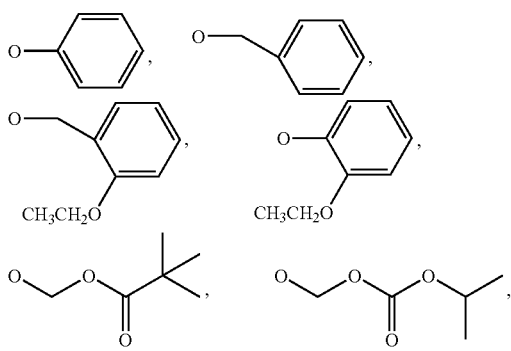

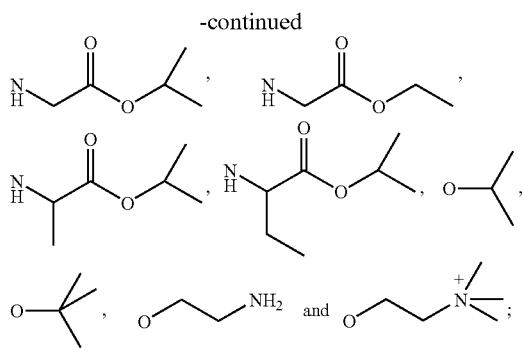

Compounds VPC23065, VPC23087 and VPC23075 are primary alcohols, i.e. $R_4$ of formula IX is hydroxy. These compounds demonstrate significant agonist activity at various S1P receptors. In particular, the S1P4 receptor binds to the primary alcohol S1P analogs with an $EC_{50}$ within a log order of the phosphorylated compounds. Since S1P4 is present on lymphocytes, the use of the primary alcohol analogs may be used for immuno-suppression. In addition, it is also hypothesized that the hydroxy moiety of the primary alcohols may be converted to phosphates in vivo. Therefore the primary alcohol S1P analogs of the present invention are all anticipated to serve as prodrug forms of active S1P receptor modulating compounds.

S1P is metabolized by a variety of conceivable routes including phosphatases, esterases or transported into cells. The S1P signal at receptors might be prolonged if the routes of degradation could be evaded or inhibited by S1P structural analogs. The S1P analogs of the present invention can be used, in accordance with one embodiment, to inhibit or evade endogenous S1P metabolic pathways including phosphotases, esterases, transporters, and S1P acyl transferases. For example, those S1P analogs that lack an ester bond would be resistant to degradation by endogenous esterases. One embodiment of the present invention is directed to compounds that function as a S1P receptor agonists and antagonists that are resistant to hydrolysis by lipid phosphate phosphatases (LPPs) or are sub-type selective inhibitors of LPPs, and in particular are resistant to hydrolysis by sphingosine 1-phosphate phosphohydrolase. Previously described S1P mimetics contain a phosphate group, and thus are likely susceptible to hydrolysis by LPPs.

Alpha hydroxy phosphonates are well known phosphate mimetics. For example, the compounds used clinically to treat osteoporosis (pamidronate, alendronate) are alpha hydroxy bisphosphonates that are analogs of pyrophosphate. S1P analogs can be prepared wherein the phosphate moiety is replaced by an alpha substituted phosphonate, wherein the substituents are selected from the group consisting of H, OH, F, $CO_2H$, $PO_3H_2$ or double bonded oxygen. Accordingly, one aspect of the present invention is directed to lipid phosphate phosphatase resistant S1P analogs having the general structures:

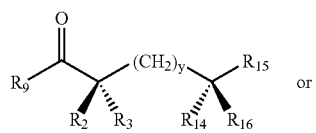

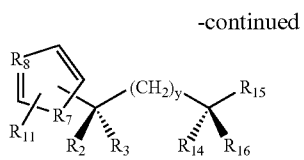

wherein $R_9$ is selected from the group consisting of —$NR_1$, and —$OR_1$;

$R_1$ is selected from the group consisting of $C_8$-$C_{22}$ alkyl, $C_8$-$C_{22}$ alkenyl, $C_8$-$C_{22}$ alkynyl and —$(CH_2)_n$—Z—$R_6$;

$R_{11}$ is —$(CH_2)_n$—Z—$R_6$; wherein n is an integer ranging from 0 to 10, Z is selected from the group consisting of aryl and heteroaryl and $R_6$ is selected from the group consisting of H, $C_1$-$C_{10}$ alkyl, $C_1$-$C_{20}$ alkoxy, $C_1$-$C_{20}$ alkylthio, and $C_1$-$C_{20}$ alkylamino;

$R_2$ and $R_3$ are independently selected from the group consisting of H, $NH_2$, OH, $C_1$-$C_6$ alkyl, —($C_1$-$C_4$ alkyl)OH, —($C_1$-$C_4$ alkyl)$NH_2$, —($C_1$-$C_4$ alkyl)aryl($C_0$-$C_4$ alkyl) and —($C_1$-$C_4$ alkyl)aryloxyaryl($C_0$-$C_4$ alkyl), wherein $R_2$ and $R_3$ are not the same and $R_2$ or $R_3$ is $NH_2$.

y is an integer from 0-10;

$R_{15}$ is represented by the formula

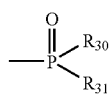

wherein $R_{30}$ is selected from the group consisting of $C_1$-$C_2$ alkoxy, hydrogen, hydroxy,

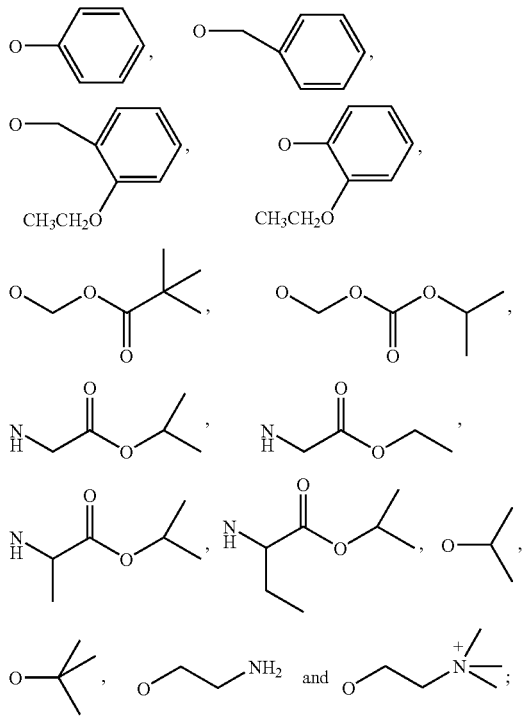

$R_{31}$ is selected from the group consisting of

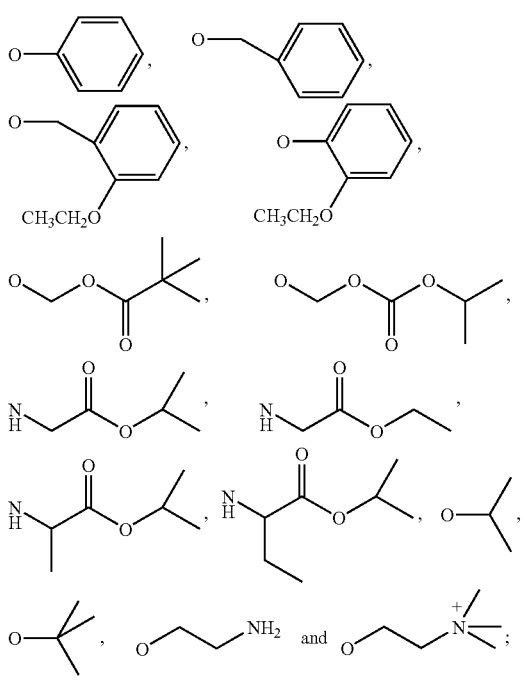

$R_{14}$ is selected from the group consisting of H, hydroxy, amino, COOH, halo, $PO_2H_2$; or $R_{14}$ and $R_{16}$ taken together form a keto group or a methylene group;

$R_{16}$ is selected from the group consisting of hydroxy, amino, COOH, halo, $PO_2H_2$; or $R_{14}$ and $R_{16}$ taken together with the carbon to which they are bound form a carbonyl or a methylene group; and $R_{17}$ is selected from the group consisting of O, S and NH. In one embodiment, $R_9$ is $-NR_1$, wherein $R_1$ is $C_8$-$C_{22}$ alkyl or $-(CH_2)_n-Z-R_6$, y is 0 or 1, $R_{14}$ and $R_{16}$ are independently H, $C_1$-$C_4$ alkyl or hydroxyl, and $R_{15}$ is OH. In an alternative embodiment, the compound has the general structure:

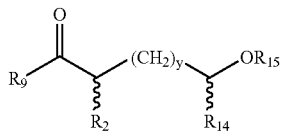

wherein $R_9$ is selected from the group consisting of $-NR_1$, and $-OR_1$;

$R_1$ is selected from the group consisting of $C_8$-$C_{22}$ alkyl, $C_8$-$C_{22}$ alkenyl, $C_8$-$C_{22}$ alkynyl and $-(CH_2)_n-Z-R_6$, wherein n is an integer ranging from 0 to 10, Z is selected from the group consisting of aryl and heteroaryl and $R_6$ is selected from the group consisting of H, $C_1$-$C_{10}$ alkyl, $C_1$-$C_{20}$ alkoxy, $C_1$-$C_{20}$ alkylthio, and $C_1$-$C_{20}$ alkylamino;

$R_2$ is $NH_2$ or OH;

y is an integer from 0-10;

$R_{15}$ is represented by the formula

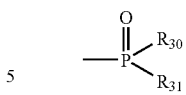

wherein $R_{30}$ and $R_{31}$ are independently selected from the group consisting of

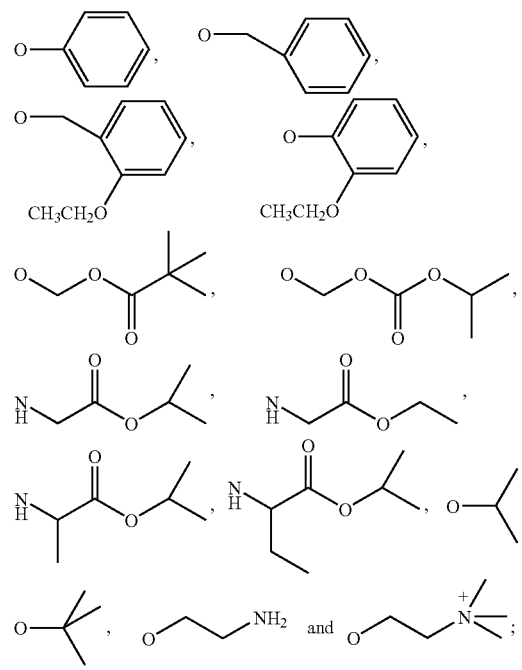

$R_{14}$ is $NH_2$ or OH; and $R_{17}$ is selected from the group consisting of O, S and NH. In one embodiment, $R_9$ is $-NR_1$, wherein $R_1$ is $C_8$-$C_{22}$ alkyl or $-(CH_2)_n-Z-R_6$, y is 0 or 1, and $R_{17}$ is O.

Lysophospholipids such as S1P and LPA, and their phosphate-containing analogs, are probably degraded by membrane bound lipid ectophosphohydrolases. This activity can be evaded by substituting phosphonate, α-substituted phosphonate, phosphothionate or other phosphate analogs as phosphate surrogates. Such compounds might also function as lipid ectophosphohydrolase inhibitors. Further, substitution of small alkyl groups (e.g. $C_1$-$C_4$ alkyl, $C_1$-$C_3$ alkylalcohol) at C-1 or C-2 might retard lipid ectophosphohydrolase cleavage by steric hindrance.

In accordance with one embodiment, an S1P receptor-modulating compound is provided wherein the compound has the general structure:

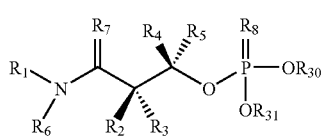

wherein $R_1$ is selected from the group consisting of alkyl, alkenyl, alkynyl, alkyl (optionally substituted aryl), alkyl (optionally substituted cycloalkyl), arylalkyl and arylalkyl (optionally substituted aryl) $R_7$ is H, O, or $R_1$ and $R_7$ taken together form an optionally substituted $C_3$-$C_6$ heteroaryl or optionally substituted $C_3$-$C_6$ heterocyclic group; $R_6$ is H, $C_1$-$C_4$ alkyl or (CH$_2$)aryl; $R_2$ and $R_3$ are independently selected from the group consisting of H, NH$_2$, OH, $C_1$-$C_6$ alkyl, —($C_1$-$C_4$ alkyl)OH, and —($C_1$-$C_4$ alkyl)NH$_2$; $R_4$ and $R_5$ are independently selected from the group consisting of H, NH$_2$, OH, $C_1$-$C_6$ alkyl, —($C_1$-$C_4$ alkyl)OH, and —($C_1$-$C_4$ alkyl)NH$_2$; $R_8$ is O, NH or S, and $R_{30}$ and $R_{31}$ are independently selected from the group consisting of

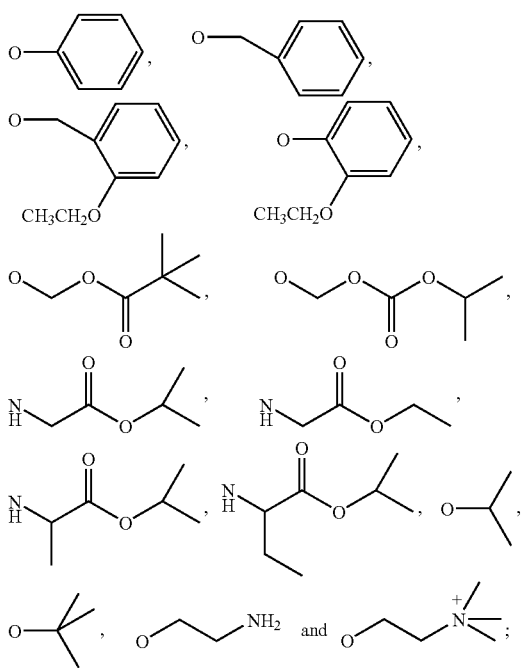

In one embodiment, one of the $R_2$ and $R_3$ substituents is NH$_2$ while the other is CH$_3$ and $R_6$ is H. In another embodiment, one of the $R_2$ and $R_3$ substituents is NH$_2$ while the other is H and one of the $R_4$ and $R_5$ substituents is CH$_3$ while the other is H, and $R_6$ is H.

In accordance with one embodiment of the invention a compound is provided that could be converted by phosphorylation to an S1P receptor-modulating compound. The compound has the general structure:

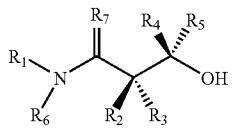

wherein $R_1$ is selected from the group consisting of alkyl, alkenyl, alkynyl, alkyl (optionally substituted aryl), alkyl (optionally substituted cycloalkyl), arylalkyl and arylalkyl (optionally substituted aryl) $R_7$ is H, O, or $R_1$ and $R_7$ taken together form an optionally substituted $C_3$-$C_6$ heteroaryl or optionally substituted $C_3$-$C_6$ heterocyclic group; $R_6$ is H, $C_1$-$C_4$ alkyl or (CH$_2$)aryl; $R_2$ and $R_3$ are independently selected from the group consisting of H, NH$_2$, OH, $C_1$-$C_6$ alkyl, —($C_1$-$C_4$ alkyl)OH, and —($C_1$-$C_4$ alkyl)NH$_2$; $R_4$ and $R_5$ are independently selected from the group consisting of H, NH$_2$, OH, $C_1$-$C_6$ alkyl, —($C_1$-$C_4$ alkyl)OH, and —($C_1$-$C_4$ alkyl)NH$_2$. In one embodiment, one of the $R_2$ and $R_3$ substituents is NH$_2$ while the other is CH$_3$ and $R_6$ is H. In another embodiment, one of the $R_2$ and $R_3$ substituents is NH$_2$ while the other is H and one of the $R_4$ and $R_5$ substituents is CH$_3$ while the other is H, and $R_6$ is H.

In accordance with one embodiment, an S1P receptor-modulating compound is provided wherein the compound has the general structure:

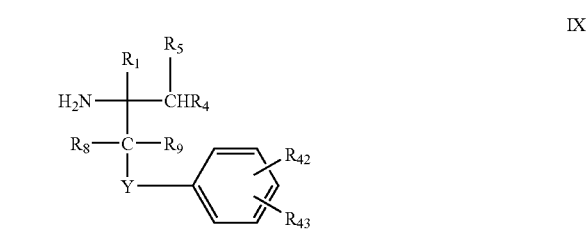

wherein $R_1$ is selected from the group consisting of $C_1$-$C_6$ alkyl, $C_1$-$C_6$ alkenyl, $C_1$-$C_6$ alkynyl, or $C_1$-$C_6$ alkyl, $C_1$-$C_6$ alkenyl, $C_1$-$C_6$ alkynyl optionally substituted with OH;

$R_{42}$ is $C_5$-$C_{10}$ alkyl, $C_5$-$C_{10}$ alkoxy, (CH$_2$)$_n$O(CH$_2$)$_m$, $C_5$-$C_{10}$ (optionally substituted aryl), $C_5$-$C_{10}$ (optionally substituted heteroaryl), $C_5$-$C_{10}$ (optionally substituted cycloalkyl), $C_5$-$C_{10}$ alkoxy (optionally substituted aryl), $C_5$-$C_{10}$ alkoxy (optionally substituted heteroaryl) and $C_5$-$C_{10}$ alkoxy (optionally substituted cycloalkyl);

$R_{43}$ is selected from the group consisting of H, halo, $C_1$-$C_6$ alkoxy, $C_1$-$C_6$ alkyl, (CH$_2$)$_y$NH$_2$, (CH$_2$)$_y$cyano and $C_1$-$C_6$ alkylthio;

$R_4$ is represented by the formula

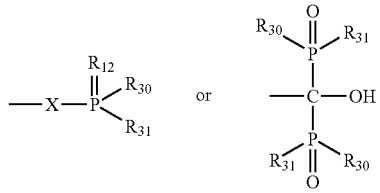

wherein $R_{12}$ is selected from the group consisting of O, NH, and S;

X is selected from the group consisting of O, NH, S, CH$_2$, CHOH, CO$_2$H, CHF, CF$_2$, and

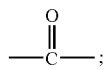

and $R_{30}$ and $R_{31}$ are independently selected from the group consisting of $C_1$-$C_2$ alkoxy,

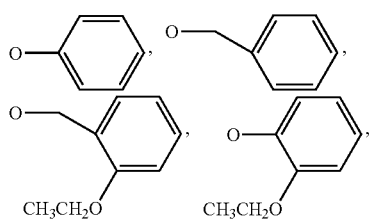

-continued

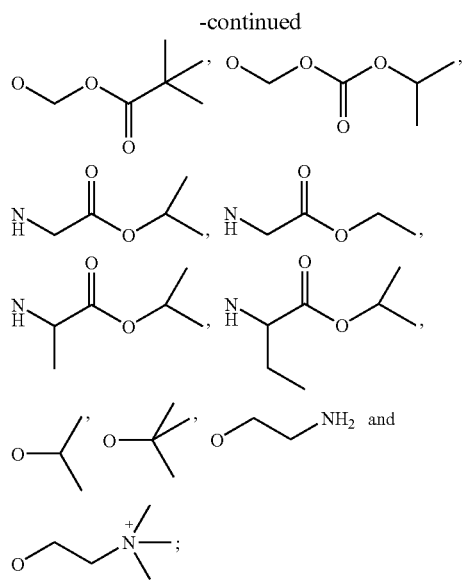

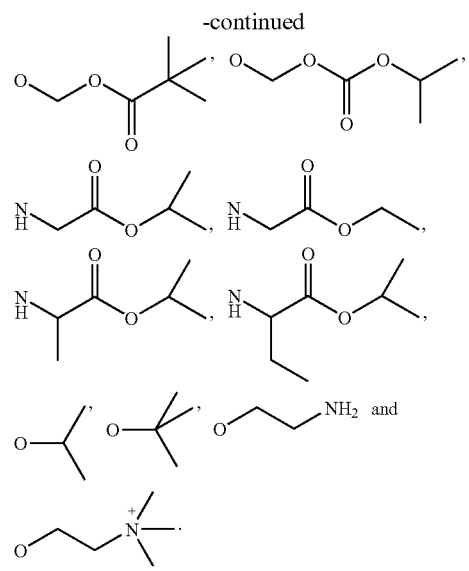

$R_5$ is selected from the group consisting of H, halo, $C_1$-$C_4$ alkyl, and haloalkyl;

Y is selected from the group consisting of $CR_8R_9$, carbonyl, NH, O or S;

$R_8$ and $R_9$ are independently selected from the group consisting of H, halo and hydroxy;

n and m are integers independently ranging from 5-10, and y is an integer ranging from 0-10. In one embodiment, a compound of Formula IX is provided with the further proviso that when $R_8$ and $R_9$ are both H, Y is not methylene. In one embodiment a compound of the Formula IX is provided wherein $R_5$ is H and $R_4$ is represented by the formula

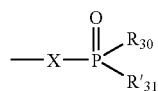

wherein X is selected from the group consisting of O, S, $CH_2$, CHOH, CHF, $CF_2$, and

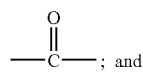

$R_{30}$ and $R_{31}$ are independently selected from the group consisting of

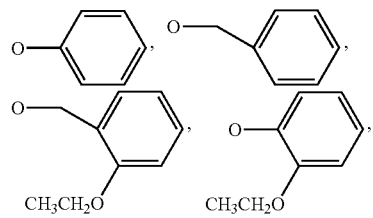

In another embodiment, a compound of the Formula IX is provided wherein X is selected from the group consisting of $CH_2$, CHF, $CF_2$, and CHOH. In a further embodiment a compound of the Formula IX is provided wherein $R_1$ is selected from the group consisting of $CH_3$, $CH_2CH_3$, $CH_2OH$, $CH_2CH_2OH$, and $CH_2CH_2CH_2OH$;

$R_{42}$ is $C_5$-$C_{10}$ alkyl, $C_5$-$C_{10}$ alkoxy, $(CH_2)_nO(CH_2)_m$, $C_5$-$C_{10}$ (optionally substituted aryl), $C_5$-$C_{10}$ (optionally substituted heteroaryl) and $C_5$-$C_{10}$ (optionally substituted cycloalkyl);

$R_{43}$ and $R_5$ are H;

$R_4$ is represented by the formula

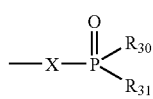

wherein X is selected from the group consisting of $CH_2$, CHOH, CHF, $CF_2$, and

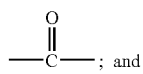

$R_{30}$ and $R_{31}$ are independently selected from the group consisting of

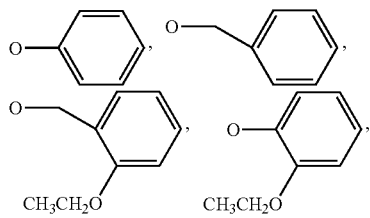

-continued

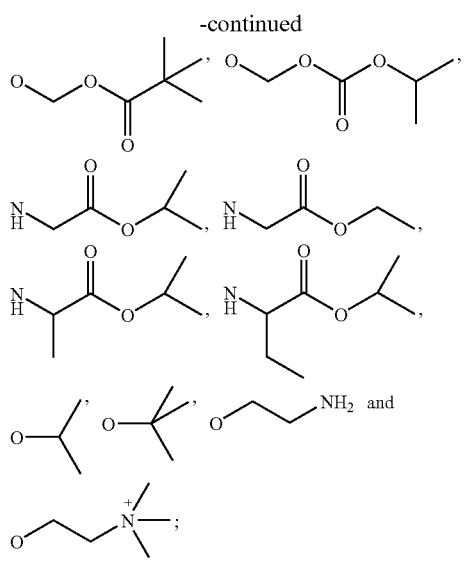

Y is selected from the group consisting of carbonyl, NH, O and S; and n and m are integers independently ranging from 5-10. In one embodiment a compound of Formula IX is provided wherein $R_1$ is —$CH_3$, or —$CH_2CH_3$; $R_{42}$ is $C_5$-$C_{10}$ alkyl; $R_{43}$, $R_5$, $R_8$, and $R_9$ are all H; $R_4$ is

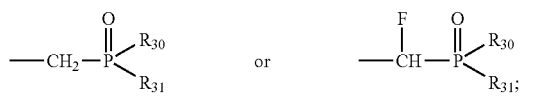

and Y is selected from the group consisting of $CR_8R_9$, carbonyl, NH and O.

The present invention also encompasses the pharmaceutically acceptable salts of the compounds of the Formula IX including salts with inorganic acids, such as hydrochloride, hydrobromide and sulfate, salts with organic acids, such as acetate, fumarate, maleate, benzoate, citrate, malate, methanesulfonate and benzenesulfonate salts, and when a carboxy group is present, salts with metals such as sodium, potassium, calcium and aluminum, salts with amines, such as triethylamine and salts with dibasic amino acids, such as lysine. The compounds and salts of the present invention encompass hydrate and solvate forms.

In one embodiment, an S1P modulating compound is provided having the general structure:

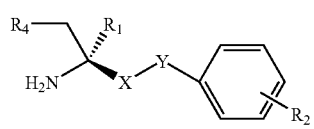

wherein $R_1$ is methyl or ethyl;

$R_2$ is selected from the group consisting of $C_5$-$C_{10}$ alkyl, $(CH_2)_nO(CH_2)_m$, $C_5$-$C_{10}$ (optionally substituted aryl), $C_5$-$C_{10}$ (optionally substituted heteroaryl), $C_5$-$C_{10}$ (optionally substituted cycloalkyl), $C_5$-$C_{10}$ alkoxy (optionally substituted aryl), $C_5$-$C_{10}$ alkoxy (optionally substituted heteroaryl) and $C_5$-$C_{10}$ alkoxy (optionally substituted cycloalkyl);

$R_4$ is

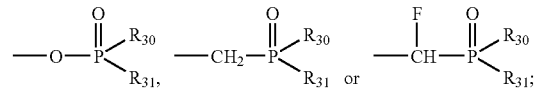

wherein $R_{30}$ and $R_{31}$ are independently selected from the group consisting of

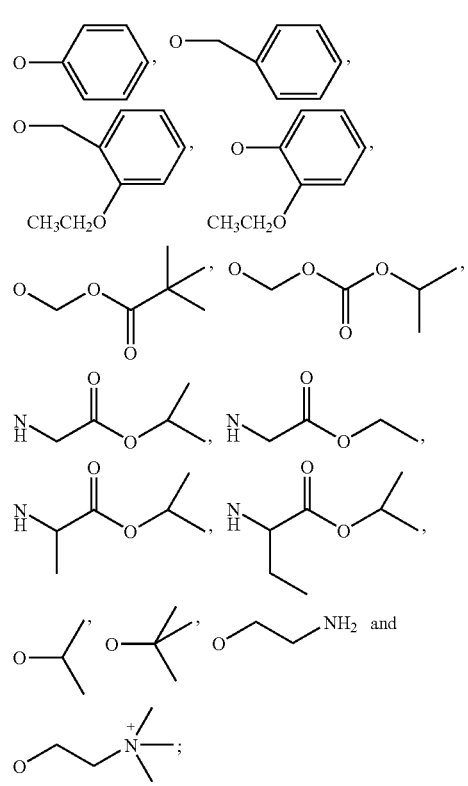

n and m are integers independently ranging from 0 to 10;

X is a methylene group optionally substituted with one or two fluorine atoms or a secondary alcohol in either stereoconfiguration;

Y is a carbonyl group, —O—, —NH— or a methylene group that is optionally substituted with one or two fluorine atoms, or a secondary alcohol in either stereoconfiguration, with the proviso that X and Y are not both methylene. In one embodiment the compound of Formula X is provided wherein $R_1$ is methyl or ethyl; $R_2$ is $C_5$-$C_{10}$ alkyl or $(CH_2)_nO(CH_2)_m$; $R_4$ is $OPO_3H_2$ or OH; X is methylene; Y is a carbonyl group, —O— or —NH—; and n and m are integers independently ranging from 0 to 10. More particularly, in one embodiment compounds of Formula X are provided wherein $R_1$ is methyl; $R_2$ is $C_5$-$C_8$ alkyl and located in the para position; $R_4$ is $OPO_3H_2$ or OH; X is methylene; and Y is a carbonyl group or —NH—.

In accordance with one embodiment, compounds suitable for use in accordance with the present invention include:

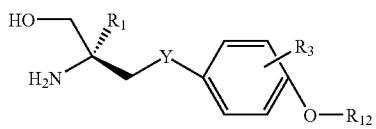

wherein $R_1$ is selected from the group consisting of —$CH_3$, —$CH_2CH_3$, $CH_2OH$, $CH_2CH_2OH$; $R_3$ is selected from the group consisting of H, $C_1$-$C_6$ alkoxy and $C_1$-$C_6$ alkyl; Y is selected from the group consisting of CHOH, $CF_2$, CFH, carbonyl, NH, O and S; and $R_{12}$ is H, $C_1$-$C_6$ alkoxy or $C_1$-$C_6$ alkyl. More particularly, suitable compounds include the following compounds:

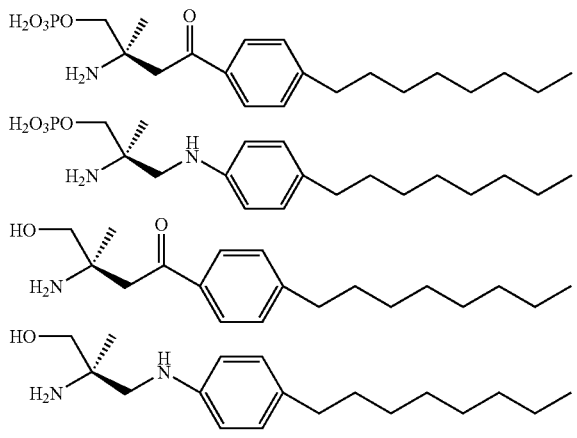

The present invention also encompasses compounds general structure:

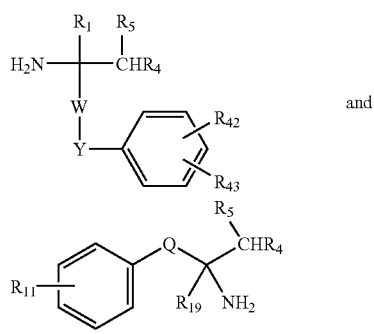

wherein $R_1$ and $R_{11}$ are independently selected from the group consisting of $C_1$-$C_{12}$ alkyl, $C_2$-$C_{12}$ alkenyl, $C_2$-$C_{12}$ alkynyl;

$R_{19}$ is selected from the group consisting of $C_1$-$C_6$ alkyl and ($C_1$-$C_6$ alkyl)OH;

Q is selected from the group consisting of

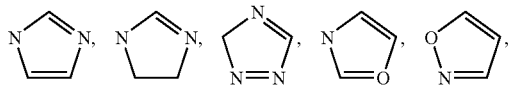

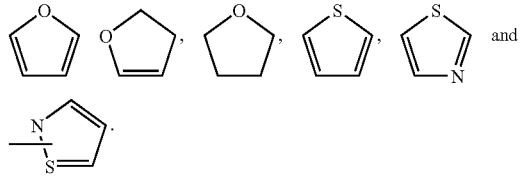

$R_{42}$ is $C_5$-$C_{12}$ alkyl, $C_2$-$C_{12}$ alkenyl$(CH_2)_nO(CH_2)_m$, $C_5$-$C_{10}$ (optionally substituted aryl), $C_5$-$C_{10}$ (optionally substituted heteroaryl) and $C_5$-$C_{10}$ (optionally substituted cycloalkyl);

$R_{43}$ is selected from the group consisting of H, halo, $C_1$-$C_6$ alkoxy, $C_1$-$C_6$ alkyl, $(CH_2)_nNH_2$, $(CH_2)_n$cyano and $C_1$-$C_6$ alkylthio;

$R_4$ is selected from the group consisting of

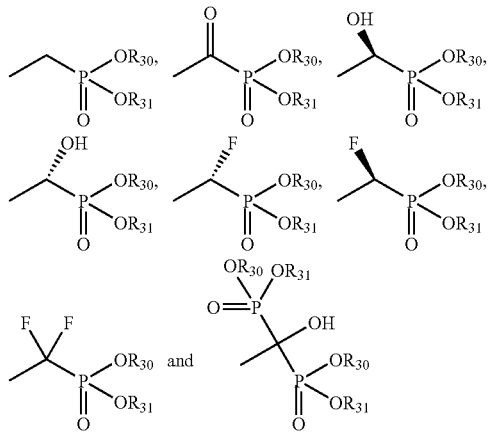

wherein $R_{30}$ and $R_{31}$ are independently selected from the group consisting of $C_1$-$C_2$ alkoxy,

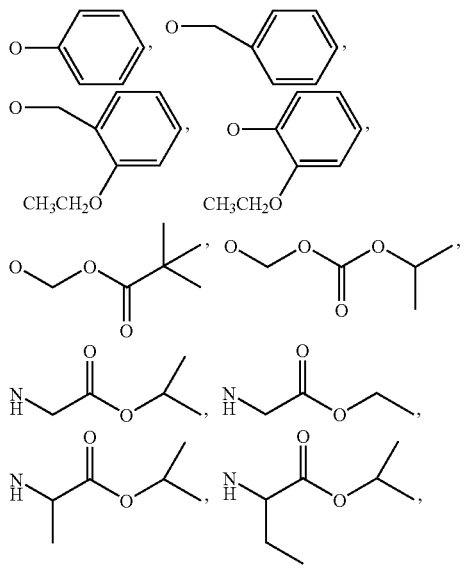

-continued

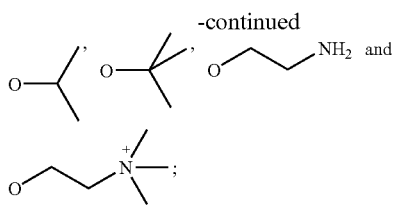

$R_5$ is selected from the group consisting of H, F, methyl or ethyl;

W is $CH_2$, CHF, $CF_2$ or CHOH;

Y is selected from the group consisting of CHF, $CF_2$, CHOH, carbonyl, NH, O or S;

n and m are integers independently ranging from 0-10. In one embodiment $R_1$ is methyl or ethyl, $R_{42}$ is $C_5$-$C_{10}$ alkyl, $C_5$-$C_{10}$ aryl or $C_5$-$C_{10}$ alkoxy, $R_{43}$ is H, $C_1$-$C_6$ alkoxy or $C_1$-$C_6$ alkyl, $R_4$ is as defined immediately above, $R_5$ is H, W is methylene and Y is a carbonyl group, methylene, —O— or —NH—; or a pharmaceutically acceptable salt or tautomer thereof. In another embodiment a compound of the general formula

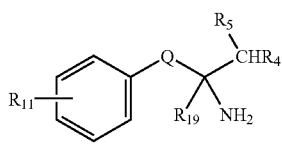

is provided wherein

Q is selected from the group consisting of

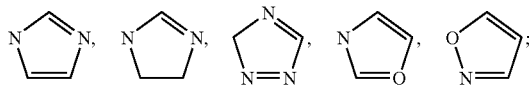

$R_{11}$ is selected from the group consisting of $C_5$-$C_{12}$ alkyl and $C_2$-$C_{12}$ alkenyl, $R_5$ is H, and $R_4$ is defined as immediately above.

The compounds of the present invention are anticipated to be high affinity agonists (or antagonists) at various sphingosine l-phosphate receptors of the 'Edg' family. The compounds of the present invention are also expected to evoke lymphopenia when introduced into rodents or humans. Thus, the compounds of the invention are immune modulators and are useful in treatment or prophylaxis of pathologies mediated by lymphocyte actions including acute or chronic rejection of tissue grafts such as organ transplants or graft vs. host disease as well as autoimmune diseases. Autoimmune diseases that could be treated with compounds of the invention include, but are not limited to, systemic lupus erythematosus, multiple sclerosis, rheumatoid arthritis, inflammatory bowel diseases including Crohn's disease and ulcerative colitis, type I diabetes, uveitis, psoriasis, and myasthenia gravis. The compounds of the invention are useful also in treating inflammatory disorders such as atopic asthma, inflammatory glomerular injury, and ischemia-reperfusion injury.

Compounds of formula XII wherein $R_{15}$ is hydroxy are primary alcohols. It is hypothesized that the hydroxy moiety of the primary alcohols is converted to phosphates in vivo. Therefore, the primary alcohol S1P analogs of the present invention are expected to serve as prodrug forms of active S1P receptor modulating compounds. Therefore, in accordance with one embodiment pharmaceutical compositions comprising the primary alcohol S1P analogs of the present invention are administered to treat patients for a variety of ailments or conditions, including the use of the compounds for immunomodulation to prevent or diminish tissue graft rejection.

S1P is metabolized by a variety of conceivable routes including phosphatases, esterases or transported into cells. The S1P signal at receptors might be prolonged if the routes of degradation could be evaded or inhibited by S1P structural analogs. The S1P analogs of the present invention can be used, in accordance with one embodiment, to inhibit or evade endogenous S1P metabolic pathways including phosphatases, esterases, transporters, and S1P acyl transferases. For example, those S1P analogs that lack an ester bond would be resistant to degradation by endogenous esterases. One embodiment of the present invention is directed to compounds that function as a S1P receptor agonists and antagonists that are resistant to hydrolysis by lipid phosphate phosphatases (LPPs) or are sub-type selective inhibitors of LPPs, and in particular are resistant to hydrolysis by sphingosine 1-phosphate phosphohydrolase. Previously described S1P mimetics contain a phosphate group, and thus are likely susceptible to hydrolysis by LPPs.

Alpha hydroxy phosphonates are well known phosphate mimetics. For example, the compounds used clinically to treat osteoporosis (pamidronate, alendronate) are alpha hydroxy bisphosphonates that are analogs of pyrophosphate. S1P analogs can be prepared wherein the phosphate moiety is replaced by an alpha hydroxy phosphonate. Accordingly, one aspect of the present invention is directed to lipid phosphate phosphatase resistant S1P analogs having the general structures of Formula IX or I wherein $R_4$ or $R_{15}$, respectively, are selected from the group consisting of

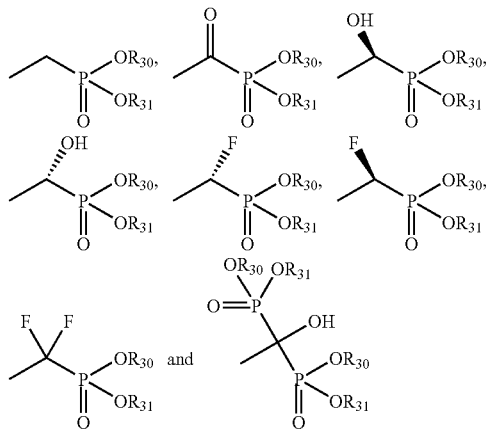

wherein $R_{30}$ and $R_{31}$ are independently selected from the group consisting of $C_1$-$C_2$ alkoxy,

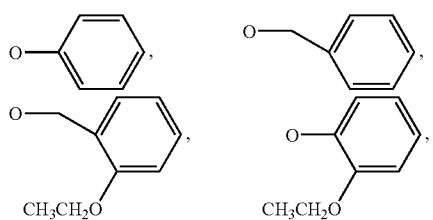

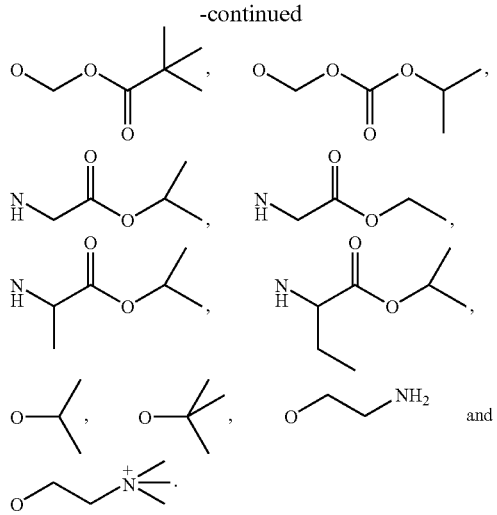

The compounds of the present invention can be used for immuno-modulation as well as in anti-angiogenesis therapy, most particularly as applied in therapy of neoplastic disease. In another embodiment, the SP1 analogs of the present invention are used in the protection of female gonads during radiation therapy such as applied to the abdomen in the course of treatment of neoplastic diseases.

Lysophospholipids, sphingosine-1-phosphate (S1P) and lysophosphatidic acid (LPA), stimulate cellular proliferation and affect numerous cellular functions by signaling through G protein-coupled endothelial differentiation gene-encoded (S1P) receptors. Accordingly, the S1P receptor agonists disclosed in the present invention are anticipated to have utility in a variety of clinical settings including but not limited to the acceleration of wound healing (including corneal wounds), the promotion of myelination (oligodendrocyte cell function) and for immuno-modulation. In particular, LPA has been reported (Balazs et al. *Am J Physiol Regul Integr Comp Physiol*, 2001 280(2):R466-472) as having activity in accelerating wound closing and increasing neoepithelial thickness.

In accordance with one embodiment of the present invention, a pharmaceutical composition comprising one or more of the S1P receptor agonists of the present invention is administered to a mammalian species (including humans) to enhance wound repair, improve neuronal function, or enhance an immune response of that species. It has also been reported that S1P inhibits fibrosis in various organs. Accordingly, the S1P receptor agonists of the present invention can be used to prevent/treat diseases associated with fibrosis of organs such as pulmonary fibrosis, interstitial pneumonia, chronic hepatitis, hepatic cirrhosis, chronic renal insufficiency, or kidney glomerular sclerosis. In one embodiment, a composition comprising an S1P receptor agonist of the present invention is used to treat wounds, including burns, cuts, lacerations, surgical incisions, bed sores, and slow-healing ulcers such as those seen in diabetics. Typically, the composition is administered locally as a topical formulation; however, other standard routes of administration are also acceptable.

In addition, it is believed that the S1P analogs of the present invention mobilize lymphocytes and increase their homing to secondary lymphoid tissues. Thus the present analogs can be used to direct lymphocytes away from transplanted organs (allografts) or healthy cells (e.g. pancreatic islets (type I diabetes), myelin sheathing (multiple sclerosis)), or other tissues that may be subjected to an undesirable immuno response and thus decrease damage to such tissues from the immune system.

In another embodiment, the S1P receptor modulating compounds of the present invention are administered to a subject to treat or prevent a disorder of abnormal cell growth and differentiation as well as inflammatory diseases. These disorders include, but are not limited to, Alzheimer's disease, aberrant corpus luteum formation, osteoarthritis, osteoporosis, anovulation, Parkinson's disease, multiple sclerosis, rheumatoid arthritis, and cancer. In accordance with one embodiment, an S1P antagonist is administered to a patient to treat a disease associated with abnormal growth. In one embodiment a composition comprising a compound of the general structure:

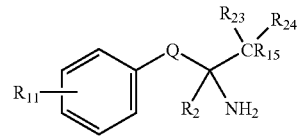

XVI wherein $R_{11}$ is $C_5$-$C_{18}$ alkyl or $C_5$-$C_{18}$ alkenyl located in the meta or para position;

Q is selected from the group consisting of $C_3$-$C_6$ optionally substituted cycloalkyl, $C_3$-$C_6$ optionally substituted heterocyclic, $C_3$-$C_6$ optionally substituted aryl $C_3$-$C_6$ optionally substituted heteroaryl, $CH_2CH_2$ and —NH(CO)—;

$R_2$ is selected from the group consisting of H, $C_1$-$C_4$ alkyl and ($C_1$-$C_4$ alkyl)OH;

$R_{23}$ is selected from the group consisting of H, F, $CO_2H$, OH, $C_1$-$C_6$ alkyl, ($C_1$-$C_4$ alkyl)OH, and ($C_1$-$C_4$ alkyl)$NH_2$;

$R_{24}$ is selected from the group consisting of H, F and $PO_3H_2$, or $R_{23}$ together with $R_{24}$ and the carbon to which they are attached form a carbonyl group; and $R_{15}$ is represented by the formula

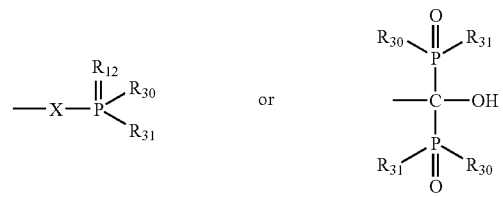

wherein $R_{12}$ is selected from the group consisting of O, NH and S;

X is selected from the group consisting of O, NH, S, $CH_2$, CHOH, $CO_2H$, CHF, $CF_2$, and

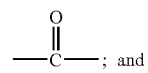; and $R_{30}$ and $R_{31}$ are independently selected from the group consisting of $C_1$-$C_2$ alkoxy,

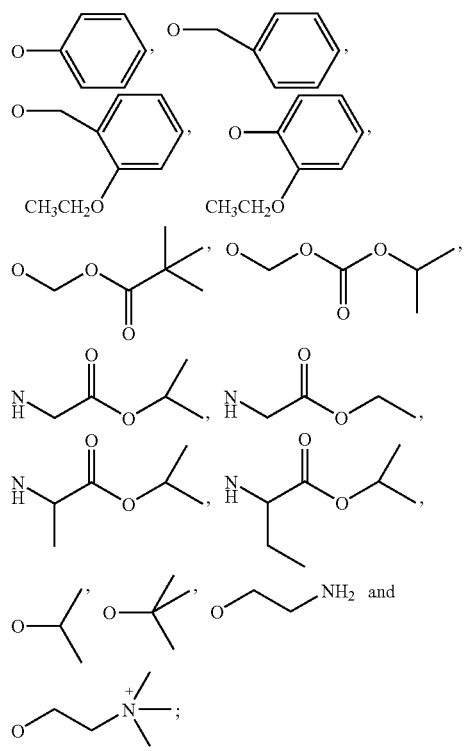

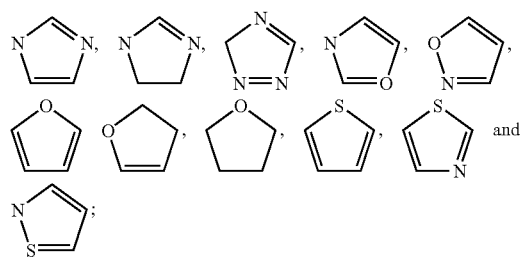

or a pharmaceutically acceptable salt or tautomer thereof is administered to treat a patient suffering from a disease associated with abnormal cell growth.

In one embodiment the compound of Formula XVI is administered to treat a patient suffering from a disease associated with abnormal cell growth wherein Q is selected from the group consisting of —NH(CO)—,

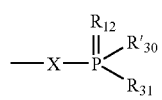

$R_{24}$ is H;
$R_{23}$ is H or $C_1$-$C_4$ alkyl;
$R_{15}$ is represented by the formula

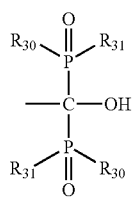

wherein $R_{12}$ is selected from the group consisting of O, NH and S;

X is selected from the group consisting of O, NH, S, $CH_2$, CHOH, $CO_2H$, CHF, $CF_2$, and

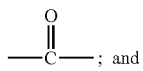

$R_{30}$ and $R_{31}$ are independently selected from the group consisting of $C_1$-$C_2$ alkoxy, hydrogen, hydroxy,

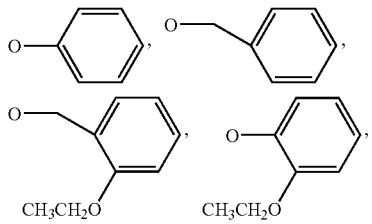

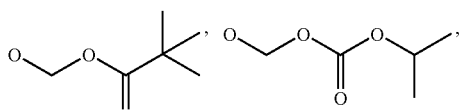

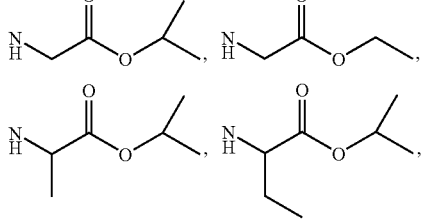

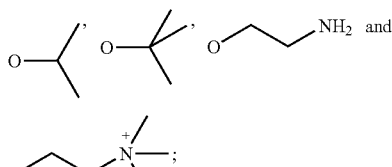

In a further embodiment Q is selected from the group consisting of

$R_{15}$ is represented by the formula

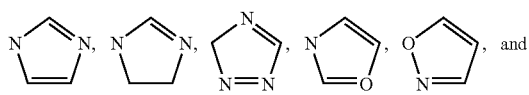

wherein X is selected from the group consisting of O, S, $CH_2$, CHOH, CHF, $CF_2$, and

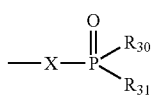

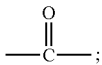

and $R_{30}$ and $R_{31}$ are independently selected from the group consisting of

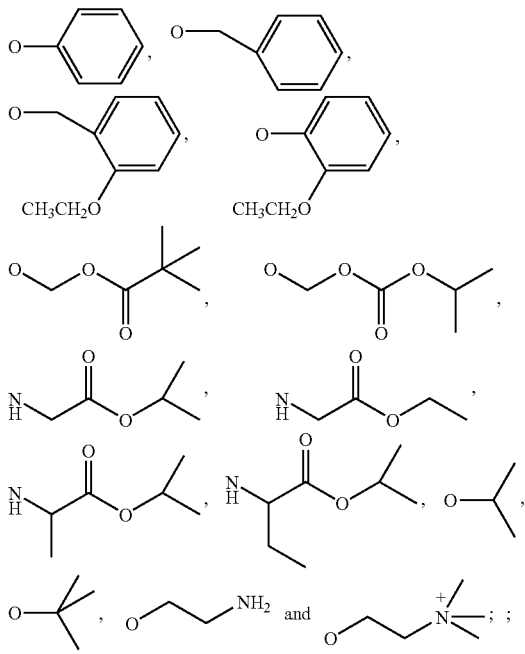

or a pharmaceutically acceptable salt or tautomer thereof.

In addition, it is believed that the S1P analogs of the present invention mobilize lymphocytes and increase their homing to secondary lymphoid tissues. Thus the present analogs can be used to direct lymphocytes away from transplanted organs (allografts) or healthy cells (e.g. pancreatic islets (type I diabetes), myelin sheathing (multiple sclerosis)), or other tissues that may be subjected to an undesirable immuno response and thus decrease damage to such tissues from the immune system.

In accordance with one embodiment the S1P analogs of the present invention are used for immuno-modulation, wherein immuno-modulation refers to an affect on the functioning of the immune system and includes lymphocyte trafficking. In accordance with one embodiment, an S1P analog of the present invention that exhibits potent agonist activity at S1P1 is administered to a warm blooded vertebrate, including a human, to induce immuno-modulation in a patient in need thereof. In one embodiment, the S1P analog is specific or has enhanced activity at the S1P1 receptor subtype relative to one or more of the other S1P receptor subtypes.

In one embodiment of the present invention, the S1P analogs of the present invention are used as immuno-modulators to alter immune system activities and prevent damage to healthy tissue that would otherwise occur in autoimmune diseases and in organ transplantation. In particular, the compounds can be administered to patients as part of the treatment associated with organ transplantation, including pancreas, pancreatic islets, kidney, heart and lung transplantations. The S1P analogs can be administered alone or in combo with known immuno-suppressants such as cyclosporine, tacrolimus, rapamycin, azathioprine, cyclophosphamide, methotrexate, and corticosteroids such as cortisol, cortisone, desoxymetasone, betametasone, desametasone, flunisolide, prednisolone, prednisone, amcinomide desonide, methylprednisolone, triamcinolone, and alclometasone.

Additionally the S1P analogs of the present invention can be administered to patients suffering from an autoimmune disease to treat that disease. Examples of diseases considered to be autoimmune in nature are: type I diabetes, systemic lupus erythematosus, multiple sclerosis, rheumatoid arthritis, inflammatory bowel disease including colitis and Crohn's disease, glomerulonephritis, uveitis, Hashimoto's thyroiditis, myasthenia gravis, autoimmune hemolytic anemia, autoimmune thrombocytopenic purpura, autoimmune hepatitis and Wegner's granuloma.

In accordance with one embodiment, an immuno-modulation therapy is provided for treating mammals, including humans, in need thereof. The method comprises the steps of administering to said mammal an effective amount of a compound represented by the formula:

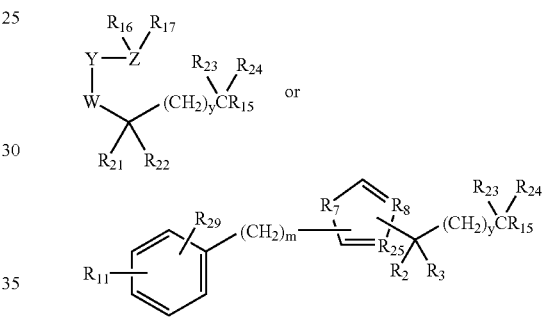

wherein

W is $CR_{27}R_{28}$ or $(CH_2)_n NH(CO)$;

wherein $R_{27}$ and $R_{28}$ are independently selected from the group consisting of H, halo and hydroxy;

Y is selected from the group consisting of a bond, $CR_9R_{10}$, carbonyl, NH, O or S;

wherein $R_9$ and $R_{10}$ are independently selected from the group consisting of H, halo, hydroxy and amino;

Z is $CH_2$, aryl, halo substituted aryl or heteroaryl;

$R_{11}$ and $R_{16}$ are independently selected from the group consisting of $C_1$-$C_{18}$ alkyl, $C_2$-$C_{18}$ alkenyl, $C_2$-$C_{18}$ alkynyl, $C_5$-$C_{18}$ alkoxy, $(CH_2)_pO(CH_2)_q$, $C_5$-$C_{10}$ (aryl)$R_{20}$, $C_5$-$C_{10}$ (heteroaryl)$R_{20}$, $C_5$-$C_{10}$ (cycloalkyl)$R_{20}$, $C_5$-$C_{10}$ alkoxy (aryl)$R_{20}$, $C_5$-$C_{10}$ alkoxy(heteroaryl)$R_{20}$ and $C_5$-$C_{10}$ alkoxy (cycloalkyl)$R_{20}$;

wherein $R_{20}$ is H or $C_1$-$C_{10}$ alkyl;

$R_{29}$ is H or halo;

$R_{17}$ is selected from the group consisting of H, halo, $NH_2$, $C_1$-$C_6$ alkyl, $C_1$-$C_6$ alkoxy, $C_1$-$C_6$ alkylamino, $C_1$-$C_6$ alkylcyano and $C_1$-$C_6$ alkylthio;

$R_2$ and $R_{21}$ are both $NH_2$;

$R_3$ is selected from the group consisting of H, $C_1$-$C_6$ alkyl, ($C_1$-$C_4$ alkyl)OH, and ($C_1$-$C_4$ alkyl)$NH_2$;

$R_{22}$ is selected from the group consisting of $C_1$-$C_6$ alkyl, ($C_1$-$C_4$ alkyl)OH and ($C_1$-$C_4$ alkyl)$NH_2$;

$R_{23}$ is selected from the group consisting of H, F, $CO_2H$, OH, $C_1$-$C_6$ alkyl, ($C_1$-$C_4$ alkyl)OH, and ($C_1$-$C_4$ alkyl)$NH_2$;

$R_{24}$ is selected from the group consisting of H, F, and $PO_3H_2$, or $R_{23}$ together with $R_{24}$ and the carbon to which they are attached form a carbonyl group;

$R_{25}$, $R_7$, and $R_8$ are each independently selected from the group consisting of O, S, $CHR_{26}$, $CHR_{26}$, $NR_{26}$, and N;

wherein $R_{26}$ is H, F, or $C_1$-$C_4$ alkyl;

$R_{15}$ is represented by the formula

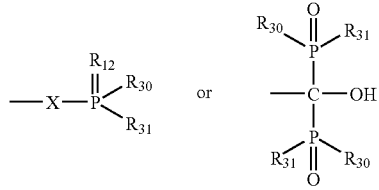

wherein $R_{12}$ is selected from the group consisting of O, NH, and S;

X is selected from the group consisting of O, NH, S, $CH_2$, CHOH, $CO_2H$, CHF, $CF_2$, and

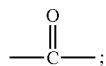

and $R_{30}$ and $R_{31}$ are independently selected from the group consisting of $C_1$-$C_2$ alkoxy, hydrogen, hydroxy,

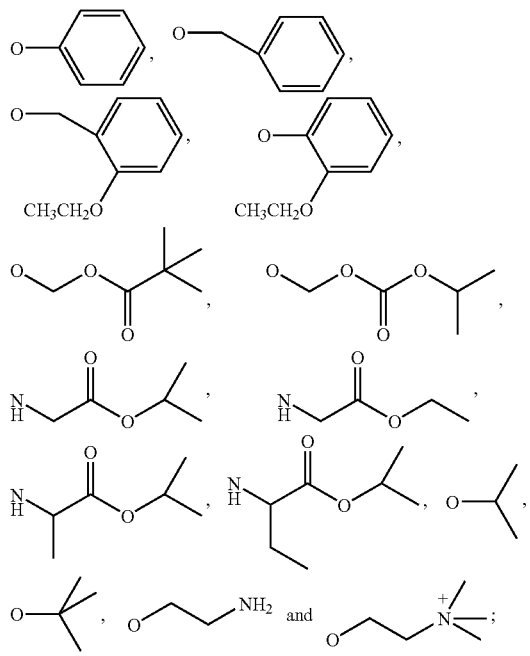

y and m are integers independently ranging from 0 to 4;
p and q are integers independently ranging from 1 to 10;
n is an integer ranging from 0 to 10;

or a pharmaceutically acceptable salt or tautomer thereof, with the proviso that W and Y are not both methylene. In one embodiment, the compound has the general structure of Formulas II-VII and XI-XIV as described herein to treat a patient by suppressing the immune system and diminishing damage to healthy tissue that would otherwise occur in autoimmune diseases and in organ transplantation.

In one embodiment, the immuno-modulating compound has the general structure:

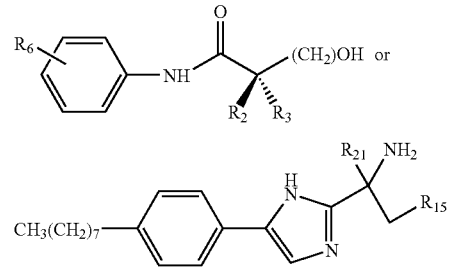

wherein $R_6$ is selected from the group consisting of $C_1$-$C_{10}$ alkyl and $R_2$ and $R_3$ are independently selected from the group consisting of H, and $NH_2$ with the proviso that $R_2$ and $R_3$ are not the same, and either $R_2$ or $R_3$ is $NH_2$; $R_{21}$ is selected from the group consisting of $C_1$-$C_6$ alkyl, ($C_1$-$C_4$ alkyl)OH and ($C_1$-$C_4$ alkyl)$NH_2$; and $R_{15}$ is represented by the formula

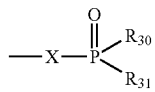

wherein X is O, $CH_2$, or CHF; $R_{30}$ and $R_{31}$ are independently selected from the group consisting of

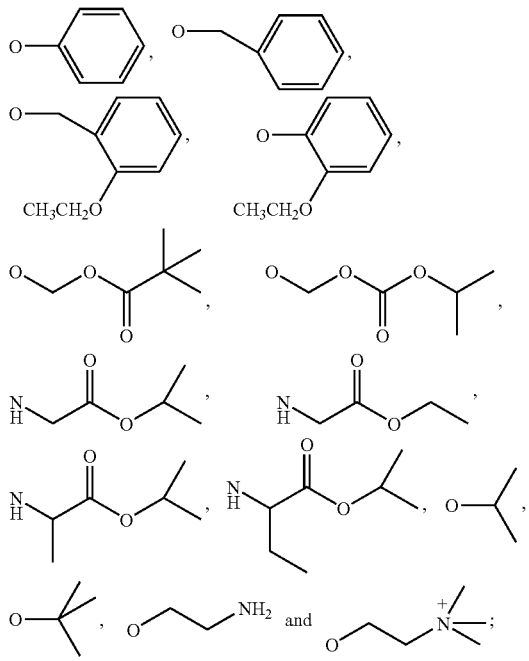

as well as pharmaceutically acceptable salts or tautomers of such compounds.

In one embodiment, a compound of the invention has the structure of structure A:

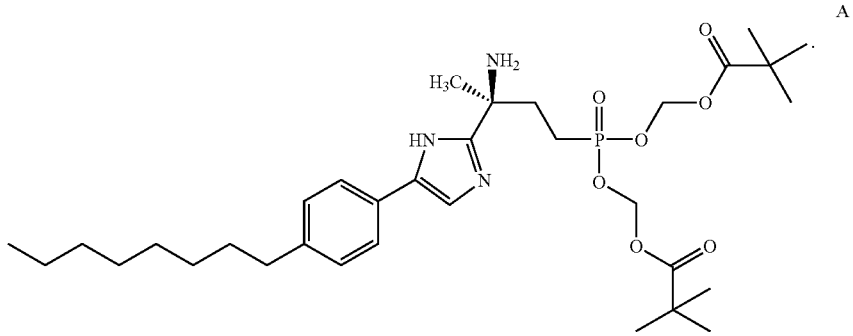

In another embodiment a compound of the invention has the general structure of structure B:

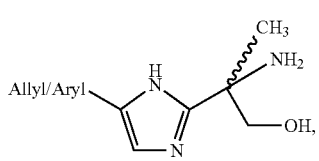

wherein said structure is modified to comprise an ester as described above and in Scheme B.

In one embodiment, a compound of the invention is an agonist of S1P receptor activity. In another embodiment, a compound of the invention is an agonist of an S1P receptor selected from the group consisting of S1P1, S1P2, S1P3, S1P4, and S1P5. In one aspect, a compound of the invention is preferentially selective for the S1P1 receptor.

In one embodiment, a compound of the invention is an antagonist of S1P receptor activity. In another embodiment, a compound of the invention is an antagonist of an S1P receptor selected from the group consisting of S1P1, S1P2, S1P3, S1P4, and S1P5. In one aspect, a compound of the invention is preferentially selective for the S1P1 receptor.

The dosage to be used is, of course, dependent on the specific disorder to be treated, as well as additional factors including the age, weight, general state of health, severity of the symptoms, frequency of the treatment and whether additional pharmaceuticals accompany the treatment. The dosages are in general administered several times per day and preferably one to three times per day. The amounts of the individual active compounds are easily determined by routine procedures known to those of ordinary skill in the art.

S1P also acts as a survival factor in many cell types. In particular, S1P receptor agonists are anticipated to have activity in protecting cells and tissues from hypoxic conditions. In accordance with one embodiment the S1P antagonists of the present invention are administered to treat cells and tissues exposed to hypoxic conditions, including injury sustained as a result of ischemia. In accordance with one embodiment, the S1P analogs exhibiting S1P receptor antagonist activity can be used to treat ischemia reperfusion type injury. Interference with the supply of oxygenated blood to tissues is defined as ischemia. The effects of ischemia are known to be progressive, such that, over time, cellular vitality continues to deteriorate and tissues become necrotic. Total persistent ischemia, with limited oxygen perfusion of tissues, results in cell death and eventually in coagulation-induced necrosis despite reperfusion with arterial blood. A substantial body of evidence indicates that a significant proportion of the injury associated with ischemia is a consequence of the events associated with reperfusion of ischemic tissues, hence the term reperfusion injury.

The present invention is also directed to methods for discovering agonists and antagonists of the interaction between S1P and the S1P receptor. Such compounds are identified by using an assay for detecting S1P receptor activity (such as the [γ-35 S]GTP binding assay) and assaying for activity in the presence of S1P and the test compound. More particularly, in the method described by Traynor and Nahorski, 1995, Mol. Pharmacol. 47: 848-854, incorporated herein by reference, G-protein coupling to membranes can be evaluated by measuring the binding of labeled GTP.

For example, samples comprising membranes isolated from cells expressing an S1P polypeptide can be incubated in a buffer promoting binding of the polypeptide to ligand (i.e. S1P), in the presence of radiolabeled GTP and unlabeled GDP (e.g., in 20 mM HEPES, pH 7.4, 100 mM NaCl, and 10 mM $MgCl_2$, 80 pM $^{35}$S-GTPγS and 3 μM GDP), with and without a candidate modulator. The assay mixture is incubated for a suitable period of time to permit binding to and activation of the receptor (e.g., 60 minutes at 30° C.), after which time unbound labeled GTP is removed (e.g., by filtration onto GF/B filters). Bound, labeled GTP can be measured by liquid scintillation counting. A decrease of 10% or more in labeled GTP binding as measured by scintillation counting in a sample containing a candidate modulator, relative to a sample without the modulator, indicates that the candidate modulator is an inhibitor of S1P receptor activity.

A similar GTP-binding assay can be performed without the presence of the ligand (i.e. S1P) to identify agents that act as agonists. In this case, ligand-stimulated GTP binding is used as a standard. An agent is considered an agonist if it induces at least 50% of the level of GTP binding induced by S1P when the agent is present at 10 μM or less, and preferably will induce a level which is the same as or higher than that induced by ligand.

GTPase activity can be measured by incubating cell membrane extracts containing an S1P receptor with $γ^{32}$P-GTP. Active GTPase will release the label as inorganic phosphate, which can be detected by separation of free inorganic phosphate in a 5% suspension of activated charcoal in 20 mM $H_3PO_4$, followed by scintillation counting. Controls would include assays using membrane extracts isolated from cells not expressing an S1P receptor (e.g., mock-transfected cells), in order to exclude possible non-specific effects of the candidate modulator. In order to assay for the effect of a candidate modulator on S1P-regulated GTPase activity, cell membrane samples can be incubated with a ligand (e.g., S1P), with, and without the modulator, and a GTPase assay can be performed as described above. A change (increase or decrease) of 10% or more in the level of GTP binding or GTPase activity relative to samples without modulator is indicative of S1P modulation by a candidate modulator.

Identified S1P receptor agonists and antagonists can be used to treat a variety of human diseases and disorders, including, but not limited to the treatment of infections such as bacterial, fungal, protozoan and viral infections, particularly infections caused by HIV-1 or HIV-2; pain; cancers; diabetes, obesity; anorexia; bulimia; asthma; Parkinson's disease; acute heart failure; hypotension; hypertension; urinary retention; osteoporosis; angina pectoris; myocardial infarction; stroke; ulcers; asthma; allergy; benign prostatic hypertrophy; migraine; vomiting; psychotic and neurological disorders, including anxiety, schizophrenia, manic depression, depression, delirium, dementia, and severe mental retardation.

The present invention is also directed to pharmaceutical compositions comprising the S1P receptor modulating compounds of the present invention. More particularly, such S1P receptor agonists and antagonists can be formulated as pharmaceutical compositions using standard pharmaceutically acceptable carriers, fillers, solubilizing agents and stabilizers known to those skilled in the art. For example, a pharmaceutical composition with which an appropriate S1P receptor agonist or antagonist, or analogs, derivatives, or modifications thereof, as described herein, is used to administer the appropriate compound to a subject.

Pharmaceutical compositions comprising the S1P receptor agonists and/or antagonists are administered to a subject in need thereof by any number of routes and means including, but not limited to, topical, oral, buccal, intravenous, intramuscular, intra-arterial, intramedullary, intrathecal, intraventricular, transdermal, subcutaneous, intraperitoneal, intranasal, enteral, topical, sublingual, vaginal, ophthalmic, pulmonary, or rectal means. The oral route is typically employed for most conditions requiring the compounds of the invention. Preference is given to intravenous injection or infusion for the acute treatments. For maintenance regimens, the oral or parenteral, e.g. intramuscular or subcutaneous, route is preferred.

In accordance with one embodiment, a composition is provided that comprises an S1P analog of the present invention and albumin, more particularly, the composition comprises an S1P analog of the present invention, a pharmaceutically acceptable carrier and 0.1-1.0% albumin. Albumin functions as a buffer and improves the solubility of the compounds. In one aspect, albumin is not added.

In one embodiment, the pharmaceutical compositions useful for practicing the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 100 g/kg/day.

Pharmaceutically acceptable carriers which are useful include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Compounds which are identified using any of the methods described herein may be formulated and administered to a subject for treatment of any of the diseases and disorders described herein. However, the use of compounds of the invention should not be construed to include only the diseases and disorder described herein. Preferably the subject is a human.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts.

Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gelcaps, and caplets, that are adapted for controlled-release are encompassed by the present invention.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water, or other physiological conditions or compounds.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

As used herein, an "oily" liquid is one which comprises a carbon-containing liquid molecule and which exhibits a less polar character than water.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, a paste, a gel, a toothpaste, a mouthwash, a coating, an oral rinse, or an emulsion. The terms oral rinse and mouthwash are used interchangeably herein.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface-active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. See Genaro, ed., 1985, Remington's Pharmaceutical Sciences, Mack Publishing Co., Easton, Pa., which is incorporated herein by reference.

The compound can be administered to a subject as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the subject etc.

The invention also provides a pharmaceutical pack or kit comprising one or more containers filled with one or more of the ingredients of the pharmaceutical compositions of the invention. In accordance with one embodiment, a kit is provided for treating a subject in need of immuno-modulation. Preferably, the subject is a human. In one embodiment, the kit comprises one or more of the S1P analogs of the present invention and may also include one or more known immunosuppressants. These pharmaceuticals can be packaged in a variety of containers, e.g., vials, tubes, microtiter well plates, bottles, and the like. Other reagents can be included in separate containers and provided with the kit; e.g., positive control samples, negative control samples, buffers, cell culture media, etc. Preferably, the kits will also include instructions for use.

Although any methods and materials similar or equivalent to those described herein can be used in the practice or testing of the present invention, the preferred methods and materials are described herein.

One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

The invention is now described with reference to the following examples. These examples are provided for the purpose of illustration only and the invention should in no way be construed as being limited to these examples but rather should be construed to encompass any and all variations which become evident as a result of the teaching provided herein.

Example 1

Chemical Syntheses of S1P Analogs

To develop good mimetics for S1P, a synthetic route was designed that had several aspects in mind (Scheme 1). First, butoxycarbonyl protected L-serine was chosen as starting material primarily because it retrosynthetically resembled the Linker region of S1P. In addition, the starting material is a cheap and commercially available protected amino acid. Secondly, chemodivergence was taken into consideration. Coupling of the long chain was performed late in the synthesis so that several chain lengths could be prepared from a common intermediate. Another important issue to address was the overwhelming insolubility of the final compounds. Due to this insolubility, the target molecules could not be purified by chromatography or crystallization methods, nor could they tolerate a simple workup. It was therefore necessary to design a final step that quantitatively generated only the target product, and allowed for removal of excess reagents under vacuum. This was accomplished by employing trifluoroacetic acid deprotection at the end of the route.

The syntheses of the S1P analogs described in the synthetic schemes of Example 1 were accomplished using solvents purified by filtration through alumina (activity I) and unless otherwise indicated all reactions were conducted at room temperature. All reactions were performed under an inert atmosphere and all products were purified using 230-400 mesh silica gel. Each product was analyzed by thin layer chromatography (single spot) and spectroscopic methods including $^1$H NMR, $^{13}$C NMR, and mass spectrometry. The assigned structures of the S1P analogs were consistent with all spectral data obtained. All final products were obtained as the TFA salts.

Scheme 1
Synthesis of (2S) S1P Analogs VPC22041, 51, 53, and 63

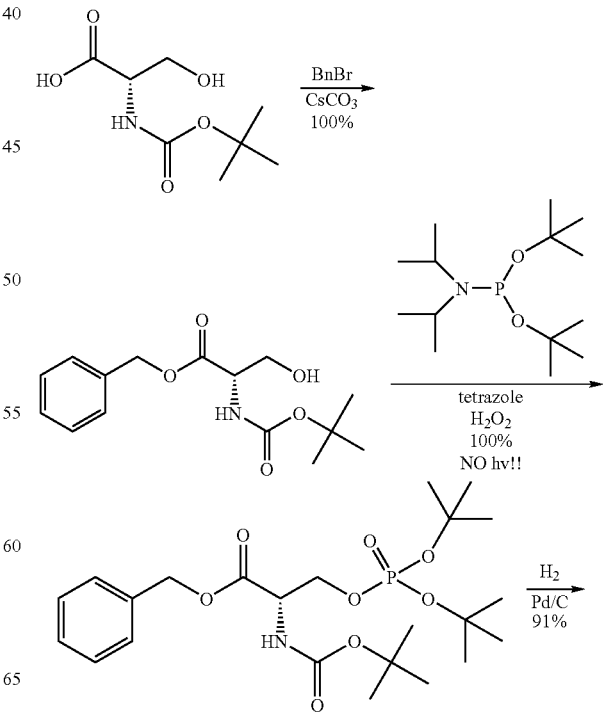

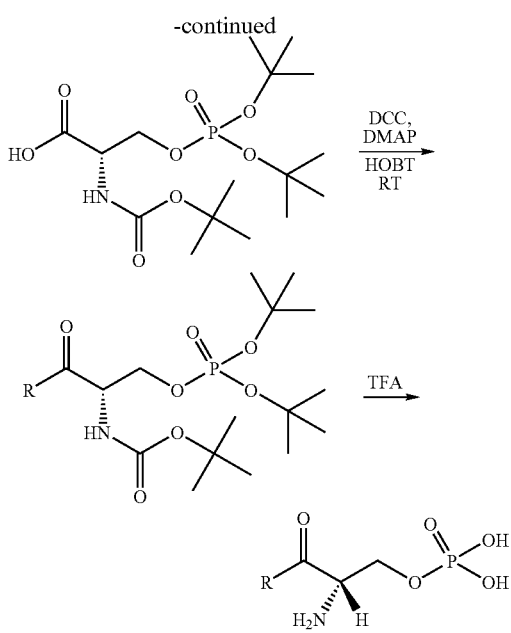

VPC22041: R = NH(CH$_2$)$_{11}$CH$_3$
VPC22053: R = O(CH$_2$)$_{13}$CH$_3$
VPC22051: R = NH(CH$_2$)$_{13}$CH$_3$
VPC22063: R = NH(CH$_2$)$_{15}$CH$_3$

| Compound | R | % Yields | | | | |
|---|---|---|---|---|---|---|
| | | A | B | C | D | E |
| VPC22041 | n-C$_{12}$H$_{25}$NH | 100 | 100 | 91 | 33 | 100 |
| VPC22051 | n-C$_{14}$H$_{29}$NH | 100 | 100 | 91 | 41 | 96 |
| VPC22053 | n-C$_{14}$H$_{29}$O | 100 | 100 | 91 | 15 | 100 |
| VPC22063 | n-C$_{16}$H$_{33}$NH | 100 | 100 | 91 | 26 | 100 |

Benzyl protection of N-Boc serine. To a stirring solution of N-Boc-(L)-Serine (4.87 mmol) in DMF (100 mL) was added cesium carbonate (5.11 mmol) and stirring was continued 30 minutes. Benzyl bromide (5.84 mmol) was then added and the resulting solution was stirred 12 hours. The reaction mixture was then diluted with ethyl acetate (25 mL), washed with lithium bromide (3×15 mL), sodium bicarbonate (2×15 mL), and brine (2×15 mL). The organic layer was dried over sodium sulfate. The solvent was then removed under reduced pressure and the resulting tan oil was purified by flash chromatography, using 1:1 petroleum ether/diethyl ether, to afford the product (100%) as a white solid. R$_f$=0.26 (1:1 petroleum ether/diethyl ether).

Phosphorylation of resulting alcohol. For phosphorylation, reaction is performed in the absence of light, work up and columns are completed with as little light as possible. To a solution of the benzyl protected serine (1.98 mmol) in 1:1 CH$_2$Cl$_2$/THF (50 mL) was added tetrazole (3.96 mmol) and the resulting mixture was stirred 30 minutes. Di-tert-butyl-di-isopropylphosphoramidite (3.96 mmol) was then added and the resulting reaction mixture was stirred 15 hours. Hydrogen peroxide (7.92 mmol) was then added and the resulting mixture was stirred 3 hours, cooled to 0° C., and quenched by addition of aqueous Na$_2$S$_2$O$_5$. The resulting solution was diluted with ethyl acetate (100 mL) and extracted with 50% aqueous Na$_2$S$_2$O$_5$ (2×20 mL). The organic layer was dried over sodium sulfate and the solvent was removed under reduced pressure to afford a tan oil. Flash chromatography, using 90:10 CHCl$_3$/acetone, provided the product (97%) as a clear oil. R$_f$=0.67 (90:10 CHCl$_3$/acetone).

Debenzylation of phosphorylated serine. To a solution of the phosphorylated serine (1.55 mmol) in 200 proof ethanol (25 mL) was added a catalytic amount of palladium on activated carbon. To the resulting solution was applied a positive pressure of hydrogen gas and the reaction mixture was stirred 12 h. The reaction mixture was then filtered through a plug of celite eluting with methanol and the solvent was removed under reduced pressure to yield the product (91%) as a slightly yellow oil. R$_f$=0 (90:10 CHCl$_3$/methanol).

Coupling of long chain amine with phosphorylated acid. A solution of the acid (0.252 mmol), a catalytic amount of 4-dimethylaminopyridine, 1-hydroxybenzotriazole hydrate (0.277 mmol), the long chain amine or alcohol (0.252 mmol), and 15 mL of CH$_2$Cl$_2$ was cooled to 0° C. with stirring. To the resulting solution at 0° C. was added dicyclohexylcarbodiimide (0.277 mmol) and the mixture was allowed to return to rt. with stirring continuing for 12 hours. The reaction mixture was then recooled to 0° C. and filtered. The filtrate was washed with sodium bicarbonate (3×10 mL), ammonium chloride (3×10 mL), and the organic layers were dried over sodium sulfate. The solvent was then removed under reduced pressure and the resulting yellow oil was purified by flash chromatography to afford the product.

VPC22041: 33%, white solid, R$_f$=0.78 (90:10 CHCl$_3$/methanol).

VPC22051: 41%, white solid, R$_f$=0.80 (90:10 CHCl$_3$/methanol).

VPC22053: 15%, white solid, R$_f$=0.20 (95:5 CHCl$_3$/acetone).

VPC22063: 26%, white solid, R$_f$=0.79 (90:10 CHCl$_3$/methanol).

Deprotection of N-Boc and phosphate groups. To a stirred solution of the protected final product (0.072 mmol) in CH$_2$Cl$_2$ (1 mL) was added trifluoroacetic acid (12.98 mmol) and stirring was continued 4 hours. Under reduced pressure, solvent and excess trifluoroacetic acid were removed affording a brown oil. The oil was rinsed with ether and the solvent was removed under vacuum 5 times to afford the product.

VPC22041: 100%, white solid, R$_f$=0 (90:10 CHCl$_3$/methanol).

VPC22051: 96%, white solid, R$_f$=0 (90:10 CHCl$_3$/methanol).

VPC22053: 100%, white solid, R$_f$=0 (90:10 CHCl$_3$/methanol).

VPC22063: 100%, white solid, R$_f$=0 (90:10 CHCl$_3$/methanol).

For S1P analog VPC22051, the PyBOP coupling procedure (as used in VPC22135) was used in place of DCC coupling. The product was obtained in 15% yield as a clear oil.

Scheme 2
Synthesis of (2R) S1P Analog VPC22135

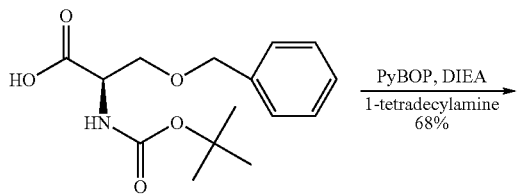

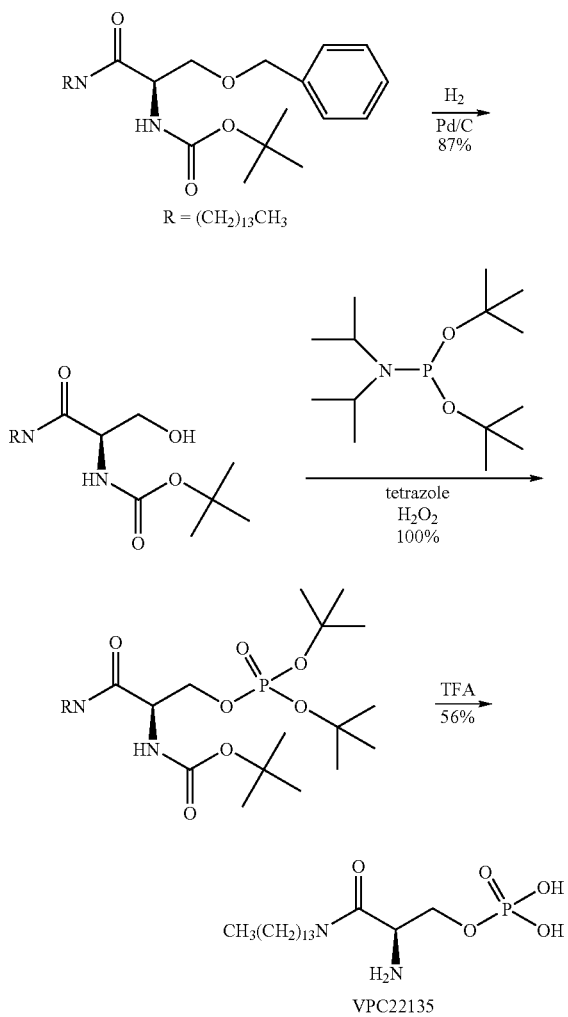

ring was continued for 1 hours after which time more 1-tetradecylamine was added (0.254 mmol). Stirring was continued for another 3 hours and then the reaction mixture was diluted with ethyl acetate (20 mL) and washed with sodium bicarbonate (3×15 mL), ammonium chloride (2×15 mL), and the organic layer was dried over sodium sulfate. Solvents were removed under reduced pressure to afford a clear gelatinous solid, which was purified by flash chromatography, using 95:5 $CHCl_3$/methanol, to afford the product (68%) as a white solid. $R_f$=0.78 (95:5 $CHCl_3$/methanol).

Benzyl deprotection of coupled product. To a solution of the coupled product (0.579 mmol) in 200 proof ethanol (15 mL) was added a catalytic amount of palladium on activated carbon. To the resulting solution was applied a positive pressure of hydrogen gas and the reaction mixture was stirred 12 hours. The reaction mixture was then filtered through a plug of celite eluting with methanol and then the solvent was removed under reduced pressure to yield the product (87%) as a clear oil. $R_f$=0.5 (95:5 $CHCl_3$/methanol).

Phosphorylation of resulting alcohol. For phosphorylation, reaction is performed in the absence of light, work up and columns are completed with as little light as possible. To a solution of the alcohol (0.474 mmol) in 1:1 $CH_2Cl_2$/THF (20 mL) was added tetrazole (0.948 mmol) and the resulting mixture was stirred 30 min. Di-tert-butyl-di-isopropylphosphoramidite (0.948 mmol) was then added and the resulting reaction mixture was stirred 15 hours. Hydrogen peroxide (1.896 mmol) was then added and the resulting mixture was then stirred 24 hours, cooled to 0° C., and quenched by addition of aqueous $Na_2S_2O_5$. The resulting solution was diluted with ethyl acetate (50 mL) and washed with sodium bicarbonate (2×15 mL), water (1×15 mL), and finally brine (1×15 mL). The organic layer was dried over sodium sulfate and the solvent was removed under reduced pressure to afford a clear oil. Flash chromatography, using 90:10 $CHCl_3$/acetone, provided the product (100%) as a clear oil. $R_f$=0.23 (90:10 $CHCl_3$/acetone).

Deprotection of N-Boc and phosphate groups. To a stirred solution of the protected product (0.071 mmol) in $CH_2Cl_2$ (1 mL) was added trifluoroacetic acid (12.98 mmol) and stirring was continued 4 hours. Under reduced pressure, solvent and excess trifluoroacetic acid were removed affording a brown oil. Rinsed oil with ether and removed under vacuum 5 times to afford the product (56%) as a white solid. $R_f$=0 (90:10 $CHCl_3$/methanol).

Coupling of long chain amine with protected serine. To a stirring solution of N-Boc-(D)-Serine-OBn (0.847 mmol) in $CH_2Cl_2$ (20 mL) was added PyBOP (0.847 mmol) followed by diisopropylethylamine (0.847 mmol). After 5 minutes of stirring, 1-tetradecylamine (0.847 mmol) was added and stir- Scheme 3
Synthesis of (2R) S1P Analog VPC22157, 173, 199, and 211

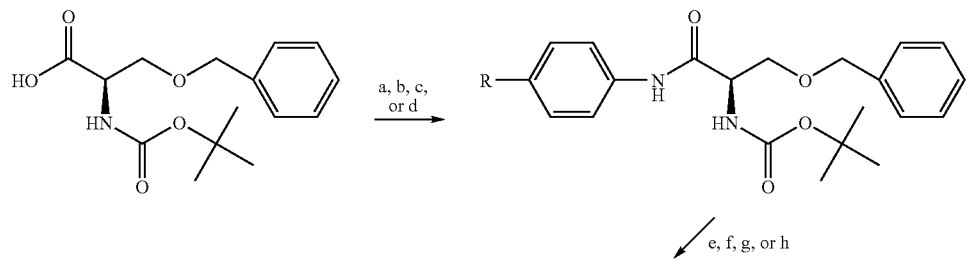

-continued

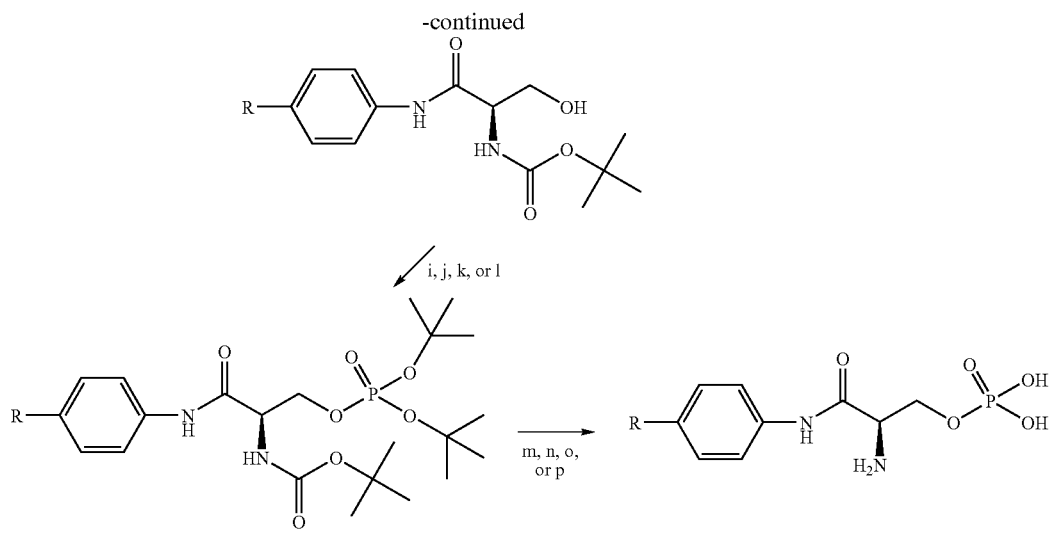

a) PyBOP, DIEA, 4-hexylaniline, 77%
b) PyBOP, DIEA, 4-octylaniline, 73%
c) PyBOP, DIEA, 4-decylaniline, 65%
d) PyBOP, DIEA, 4-dodecylaniline, 71%
e) Di$^t$Bu-di$^i$Pr-phosphoramidite, tetrazole, $H_2O_2$, 85%
f) Di$^t$Bu-di$^i$Pr-phosphoramidite, tetrazole, $H_2O_2$, 60%
g) Di$^t$Bu-di$^i$Pr-phosphoramidite, tetrazole, $H_2O_2$, 70%
h) Di$^t$Bu-di$^i$Pr-phosphoramidite, tetrazole, $H_2O_2$, 9%
i) $H_2$, Pd/C, 84%
j) $H_2$, Pd/C, 96%
k) $H_2$, Pd/C, 87%
l) $H_2$, Pd/C, 90%
m) TFA, 100%
n) TFA, 58%
o) TFA, 75%
p) TFA, 100%
VPC22157: R = $(CH_2)_5CH_3$ (a, e, i, m)
VPC22173: R = $(CH_2)_7CH_3$ (b, f, j, n)
VPC22199: R = $(CH_2)_9CH_3$ (c, g, k, o)
VPC22211: R = $(CH_2)_{11}CH_3$ (d, h, l, p)

Coupling of long chain aniline with protected serine. To a stirring solution of N-Boc-(D)-Serine-OBn (0.339 mmol) in $CH_2Cl_2$ (10 mL) was added PyBOP (0.339 mmol) followed by diisopropylethylamine (0.339 mmol). After minutes of stirring, the aniline (0.339 mmol) was added and stirring was continued for 4 hours. The reaction mixture was then diluted with ethyl acetate (10 mL) and washed with sodium bicarbonate (3×10 mL), ammonium chloride (2×10 mL), and the organic layer was dried over sodium sulfate. Solvents were removed under reduced pressure to afford a clear gelatinous solid, which was purified by flash chromatography to afford the product.

VPC22157: 77%, white solid, $R_f$=0.80 (90:10 $CHCl_3$/acetone).

VPC22173: 73%, white solid, $R_f$=0.78 (90:10 $CHCl_3$/acetone).

VPC22199: 65%, white solid, $R_f$=0.79 (90:10 $CHCl_3$/acetone).

VPC22211: 71%, white solid, $R_f$=0.80 (90:10 $CHCl_3$/acetone).

Benzyl deprotection of coupled product. To a solution of the coupled product (0.260 mmol) in 200 proof ethanol (10 mL) was added a catalytic amount of palladium on activated carbon. To the resulting solution was applied a positive pressure of hydrogen gas and the reaction mixture was stirred 12 hours. The reaction mixture was then filtered through a plug of celite eluting with methanol and then the solvent was removed under reduced pressure to yield the product.

VPC22157: 85%, clear oil, $R_f$=0.50 (95:5 $CHCl_3$/methanol).

VPC22173: 60%, clear oil, $R_f$=0.55 (95:5 $CHCl_3$/methanol).

VPC22199: 70%, clear oil, $R_f$=0.48 (95:5 $CHCl_3$/methanol).

VPC22211: 9%, clear oil, $R_f$=0.53 (95:5 $CHCl_3$/methanol).

Phosphorylation of resulting alcohol. For phosphorylation, reaction is performed in the absence of light, work up and columns are completed with as little light as possible. To a solution of the alcohol (0.220 mmol) in 1:1 $CH_2Cl_2$/THF (10 mL) was added tetrazole (0.400 mmol) and the resulting mixture was stirred 30 min. Di-tert-butyl-di-isopropylphosphoramidite (0.400 mmol) was then added and the resulting reaction mixture was stirred 15 hours. Hydrogen peroxide (0.800 mmol) was then added and the resulting mixture was then stirred 24 hours, cooled to 0° C., and quenched by addition of aqueous $Na_2S_2O_5$. The resulting solution was diluted with ethyl acetate (25 mL) and washed with sodium bicarbonate (2×10 mL), water (1×10 mL), and finally brine (1×10 mL). The organic layer was dried over sodium sulfate and the solvent was removed under reduced pressure to afford a clear oil. Flash chromatography provided the product as a clear oil.

VPC22157: 84%, clear oil, $R_f$=0.23 (90:10 $CHCl_3$/acetone).

VPC22173: 96%, clear oil, $R_f$=0.30 (90:10 $CHCl_3$/acetone).

VPC22199: 87%, clear oil, $R_f$=0.72 (80:20 CHCl$_3$/acetone).

VPC22211: 90%, clear oil, $R_f$=0.58 (80:20 CHCl$_3$/acetone).

Deprotection of N-Boc and phosphate groups. To a stirred solution of the protected product (0.162 mmol) in CH$_2$Cl$_2$ (2 mL) was added trifluoroacetic acid (25.96 mmol) and stirring was continued 4 hours. Under reduced pressure, solvent and excess trifluoroacetic acid were removed affording a brown oil. Rinsed oil with ether and removed under vacuum 5 times to afford the product.

VPC22157: 100%, white solid, $R_f$=0 (90:10 CHCl$_3$/methanol).

VPC22173: 58%, white solid, $R_f$=0 (90:10 CHCl$_3$/methanol).

VPC22199: 75%, white solid, $R_f$=0 (90:10 CHCl$_3$/methanol).

VPC22211: 100%, white solid, $R_f$=0 (90:10 CHCl$_3$/methanol).

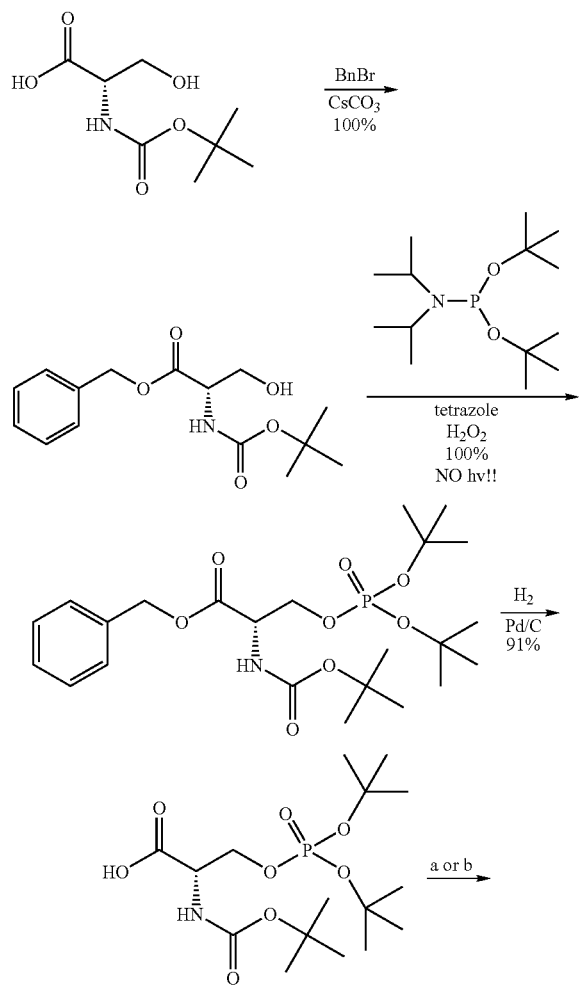

Scheme 4
Synthesis of (2S) S1P Analogs VPC22179 and 181

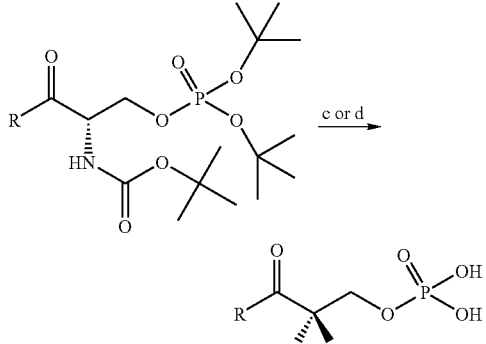

a) PyBOP, DIEA, 4-hexylaniline, 43%
b) PyBOP, DIEA, 4-octylaniline, 60%
c) TFA, 100%
d) TFA, 100%

VPC22179: R = NHPh(CH$_2$)$_5$CH$_3$ (a, c)
VPC22181: R = NHPh(CH$_2$)$_7$CH$_3$ (b, d,)

Benzyl protection of N-Boc serene. To a stirring solution of N-Boc-(L)-Serine (2.44 mmol) in DMF (50 mL) was added cesium carbonate (2.56 mmol) and stirring was continued 30 minutes. Benzyl bromide (2.92 mmol) was then added and the resulting solution was stirred 12 hours. The reaction mixture was then diluted with ethyl acetate (15 ml), washed with lithium bromide (3×10 mL), sodium bicarbonate (2×10 mL), and brine (2×10 mL). The organic layer was dried over sodium sulfate. The solvent was then removed under reduced pressure and the resulting tan oil was purified by flash chromatography, using 1:1 petroleum ether/diethyl ether, to afford the product (100%) as a white solid. $R_f$=0.26 (1:1 petroleum ether/diethyl ether).

Phosphorylation of resulting alcohol. For phosphorylation, reaction is performed in the absence of light, work up and columns are completed with as little light as possible. To a solution of the benzyl protected serine (2.22 mmol) in 1:1 CH$_2$Cl$_2$/THF (100 mL) was added tetrazole (4.43 mmol) and the resulting mixture was stirred 30, min. Di-tert-butyl-di-isopropylphosphoramidite (4.43 mmol) was then added and the resulting reaction mixture was stirred 15 hours. Hydrogen peroxide (8.86 mmol) was then added and the resulting mixture was stirred 3 hours, cooled to 0° C., and quenched by addition of aqueous Na$_2$S$_2$O$_5$. The resulting solution was diluted with ethyl acetate (100 mL) and extracted with 50% aqueous Na$_2$S$_2$O$_5$ (2×20 mL). The organic layer was dried over sodium sulfate and the solvent was removed under reduced pressure to afford a tan oil. Flash chromatography, using 90:10 CHCl$_3$/acetone, provided the product (97%) as a clear oil. $R_f$=0.67 (90:10 CHCl$_3$/acetone).

Debenzylation of phosphorylated serine. To a solution of the phosphorylated serine (1.55 mmol) in 200 proof ethanol (25 mL) was added a catalytic amount of palladium on activated carbon. To the resulting solution was applied a positive pressure of hydrogen gas and the reaction mixture was stirred 12 hours. The reaction mixture was then filtered through a plug of celite eluting with methanol and the solvent was removed under reduced pressure to yield the product (91%) as a slightly yellow oil. $R_f$=0 (90:10 CHCl$_3$/methanol).

Coupling of long chain aniline with phosphorylated acid. To a stirring solution of the phosphorylated acid (0.252 mmol) in CH$_2$Cl$_2$ (10 mL) was added PyBOP (0.252 mmol) followed by diisopropylethylamine (0.252 mmol). After minutes of stirring, the aniline (0.252 mmol) was added and stirring was continued for 4 hours. The reaction mixture was then diluted with ethyl acetate (10 mL) and washed with sodium bicarbonate (3×10 mL), ammonium chloride (2×10 mL), and the organic layer was dried over sodium sulfate. Solvents were removed under reduced pressure to afford the product.

VPC22179: 43%, white solid, $R_f$=0.40 (90:10 CHCl$_3$/acetone).

VPC22181: 60%, white solid, $R_f$=0.35 (90:10 CHCl$_3$/acetone).

Deprotection of N-Boc and phosphate groups. To a stirred solution of the protected final product (0.117 mmol) in CH$_2$Cl$_2$ (1.5 mL) was added trifluoroacetic acid (19.48 mmol) and stirring was continued 4 hours. Under reduced pressure, solvent and excess trifluoroacetic acid were removed affording a brown oil. The oil was rinsed with ether and the solvent was removed under vacuum 5 times to afford the product VPC22179: 100%, white solid, $R_f$=0 (90:10 CHCl$_3$/methanol).

VPC22181: 100%, white solid, $R_f$=0 (90:10 CHCl$_3$/methanol).

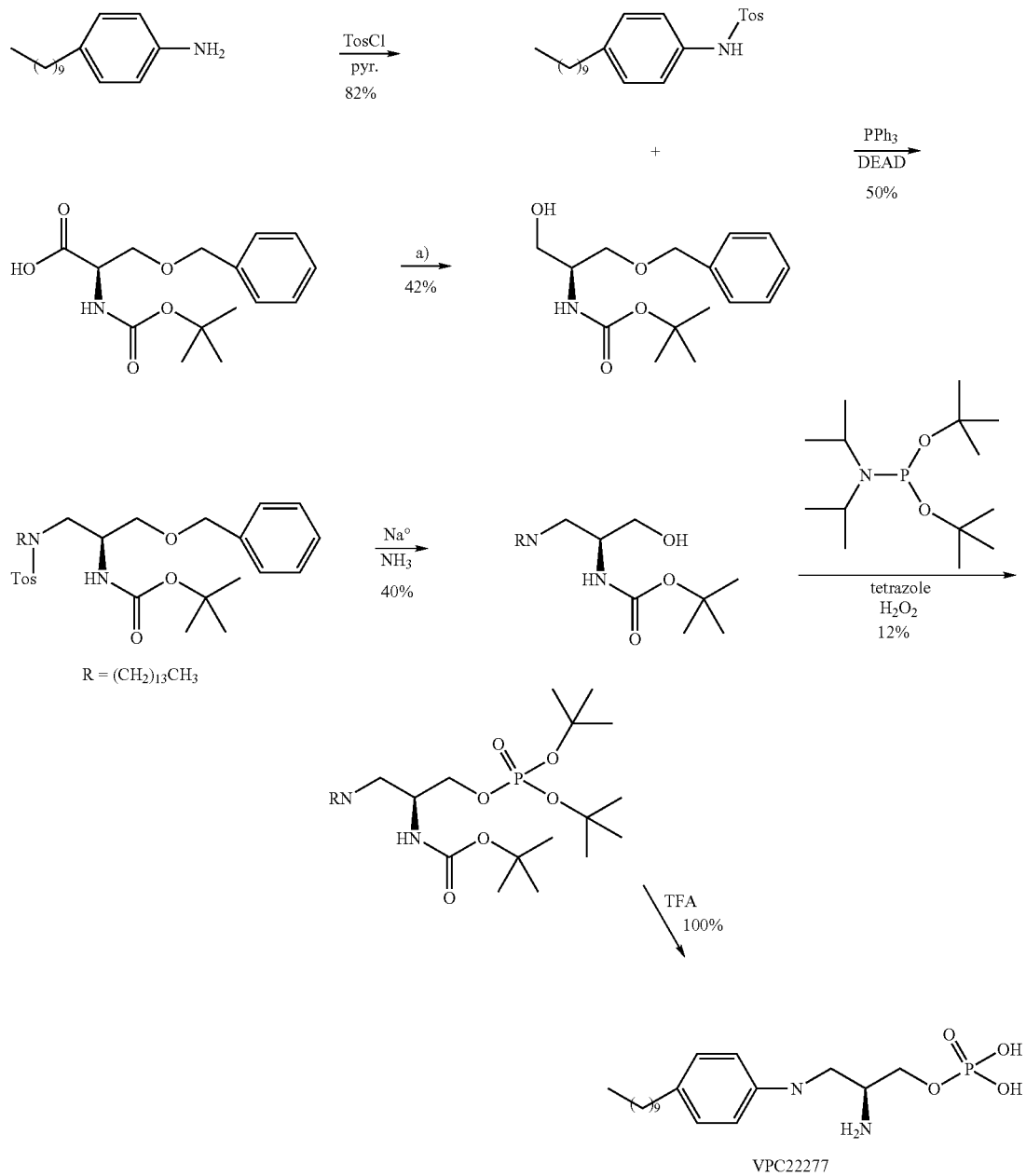

Tosyl protection of the long chain aniline. To a stirring solution of the 4-decylaniline (0.428 mmol) in pyridine (3 mL) under inert atmosphere at 0° C. was added tosyl chloride (0.428 mmol). The reaction mixture was warmed to room temperature. After 20 min., the reaction mixture was diluted with water (10 mL) and ethyl acetate (10 mL). The aqueous layer was discarded and the organic layer was washed with 1N HCl (3×10 mL), saturated sodium bicarbonate (3×10 mL) and brine (2×10 mL). The organic layer was dried over sodium sulfate and the solvent was removed under reduced pressure to yield the product (81%) as pink crystals, which needed no further purification. $R_f$=0.82 (90:10 $CHCl_3$/acetone).

Reduction of protected amino acid. At –10° C., under inert atmosphere, N-Boc-(D)-Ser-OBz (0.678 mol) and diisopropylethylamine (0.678 mmol) were added to stirring THF (3 mL). Isobutylchloroformate (0.745 mmol) was then slowly added. The reaction mixture was allowed to stir for 1 hour until a precipitate was observed. The reaction mixture was then filtered and the filtrate was re-cooled to –10° C. Meanwhile, sodium borohydride (1.36 mmol) was dissolved in stirring water (0.5 mL) under inert atmosphere and this mixture was cooled to –10° C. The original reaction mixture was then cannulated into the sodium borohydride mixture slowly and the newly formed reaction mixture was brought to room temperature and stirred 1 hour. The reaction mixture was then quenched by addition of saturated ammonium chloride (5 mL), diluted with ethyl acetate (15 mL) and the aqueous layer was discarded. The organic layer was then washed with saturated ammonium chloride (3×10 mL), saturated sodium bicarbonate (3×10 mL) and finally brine (1×10 mL). The organic layer was dried over sodium sulfate and the solvent was removed under reduced pressure to yield the crude product as a white solid. The crude product was purified by flash chromatography, using 80:20 $CHCl_3$/acetone, to afford the product (42%) as a white solid. $R_f$=0.48 (80:20 $CHCl_3$/acetone).

Coupling of aniline with alcohol. To a sting solution of the aniline (0.209 mmol) in THF (3 mL) under an inert atmosphere was added triphenylphosphine (0.254 mmol), the alcohol (0.105 mmol), and finally DEAD (0.209 mmol). The reaction mixture was stirred 12 hours and then concentrated to a clear oil. Petroleum ether was added to the clear oil and solid triphenylphosphine oxide was allowed to settle on the bottom of the flask. The clear petroleum ether layer was then pipetted off and concentrated to a clear oil. The crude product was then subjected to flash chromatography, using 1:1 petroleum ether/ether, to afford the final product (50%) as a white solid. $R_f$=0.83 (1:1 petroleum ether/ether).

Tosyl deprotection of the coupled product. Ammonia (20 mL) was condensed in a 2-neck round bottom flask equipped with a stirbar and cold finger that was cooled to –70° C. under an inert atmosphere. Sodium metal (4.27 mmol) was then added to the reaction mixture followed by the tosyl protected amine (0.427 mmol) in THF (8 mL). The dark blue reaction mixture was stirred for 1 hour at –70° C. and was then quenched with ethanol until the solution was clear/white and the reaction mixture was then stirred at room temperature overnight. The reaction mixture was then diluted with ethyl acetate (20 mL) and washed with saturated ammonium chloride (3×20 mL), saturated sodium bicarbonate (3×20 mL), and finally brine (1×20 mL). The organic layer was dried over sodium sulfate and the solvent was removed under reduced pressure to yield the crude product as a clear oil. The crude product was purified by flash chromatography, using 1:1 ethyl acetate/hexanes, to afford the product (40%) as a white solid. $R_f$=0.42 (1:1 ethyl acetate/hexanes).

Phosphorylation of resulting alcohol. For phosphorylation, reaction is performed in the absence of light, work up and columns are completed with as little light as possible. To a solution of the alcohol (0.130 mmol) in 1:1 $CH_2Cl_2$/THF (5 mL) was added tetrazole (0.130 mmol) and the resulting mixture was stirred 30 minutes. Di-tert-butyl-di-isopropylphosphoramidite (0.130 mmol) was then added and the resulting reaction mixture was stirred 15 hours. Hydrogen peroxide (30%, 0.044 mL) was then added and the resulting mixture was then stirred 24 hours, cooled to 0° C., and quenched by addition of aqueous $Na_2S_2O_5$. The resulting solution was diluted with ethyl acetate (10 mL) and washed with sodium bicarbonate (2×10 mL), water (1×10 mL), and finally brine (1×10 mL). The organic layer was dried over sodium sulfate and the solvent was removed under reduced pressure to afford a clear oil. Flash chromatography, using 1:1 ethyl acetate/hexanes, provided the product (12%) as a clear oil. $R_f$=0.41 (1:1 ethyl acetate/hexanes).

Deprotection of N-Boc and phosphate groups. To a stirred solution of the protected final product (0.016 mmol) in $CH_2Cl_2$ (0.5 mL) was added trifluoroacetic acid (6.49 mmol) and stirring was continued 4 hours. Under reduced pressure, solvent and excess trifluoroacetic acid were removed affording a brown oil. The oil was rinsed with ether and the solvent was removed under vacuum 5 times to afford the product (100%) as a white solid. $R_f$=0 (90:10 $CHCl_3$/methanol).

Scheme 6
Synthesis of (2R) S1P Analog
VPC23031, 19, 65, 69, 75 and 79

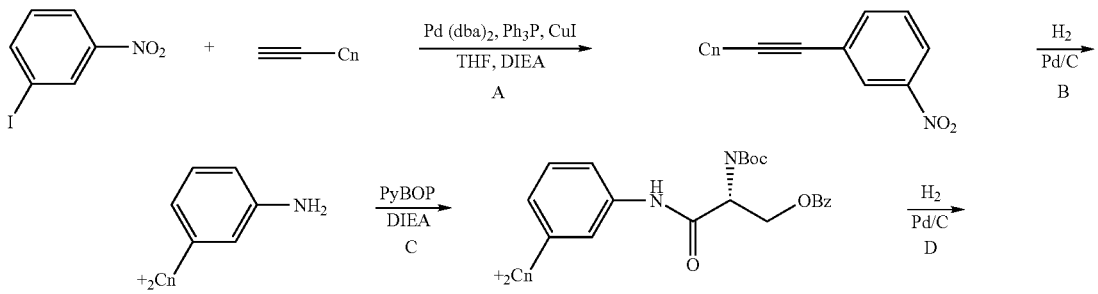

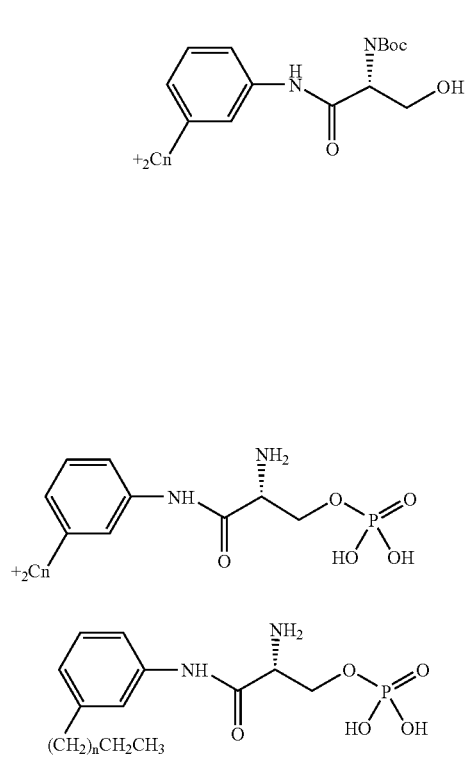

| | | % Yields | | | | | | |
|---|---|---|---|---|---|---|---|---|
| Compound(s) | n | A | B | C | D | E | F | G |
| VPC23031 | 4 | 24 | 66 | 52 | 100 | X | 90 | 100 |
| VPC23019 | 6 | 100 | 85 | 90 | 95 | X | 56 | 92 |
| VPC23065,69 | 8 | 34 | 84 | 84 | 89 | 100 | 89 | 86 |
| VPC23075,79 | 7 | 66 | 100 | 100 | 27 | 93 | 77 | 100 |

Coupling of aryl halide with terminal alkyne. All starting materials were thoroughly flushed with nitrogen before the reaction. To a stifling solution of the aryl halide (2.01 mmol), bis(dibenzylideneacetone) palladium (0.04 mmol), triphenylphosphine (0.10 mmol), and copper iodide (0.04 mmol) in THF (10 mL) under inert atmosphere was added the terminal alkyne (2.21 mmol) followed by diisopropylethylamine (8.04 mmol). The reaction mixture was then stirred at room temperature for 12 hours. The reaction mixture was then diluted with ethyl acetate (15 mL) and washed with sodium bicarbonate (3×15 mL), ammonium chloride (3×15 mL) and finally brine (1×15 mL). The organic layer was then dried over sodium sulfate. Solvents were removed under reduced pressure to afford a tan oil. Flash chromatography provided the final product.

VPC23031: 24%, yellow oil, $R_f$=0.61 (90:10 hexanes/ether).

VPC23019: 100%, yellow oil, $R_f$=0.55 (90:10 hexanes/ether).

VPC23065, 69: 66%, yellow oil, $R_f$=0.75 (90:10 hexanes/ether).

VPC23075, 79: 34%, yellow oil, $R_f$=0.75 (90:10 hexanes/ether).

Reduction of the coupled product. To a solution of the coupled product (1.68 mmol) in 200 proof ethanol (10 mL) was added a catalytic amount of palladium on activated carbon. To the resulting solution was applied a positive pressure of hydrogen gas and the reaction mixture was stirred 12 hours. The reaction mixture was then filtered through a plug of celite eluting with methanol and then the solvent was removed under reduced pressure to yield the crude product VPC23031: 66%, yellow solid, $R_f$=0.53 (95:5 $CHCl_3$/acetone).

VPC23019: 85%, yellow solid, $R_f$=0.55 (95:5 $CHCl_3$/acetone).

VPC23065, 69: 84%, yellow solid, $R_f$=0.79 (95:5 $CHCl_3$/acetone).

VPC23075, 79: 100%, yellow solid, $R_f$=0.80 (95:5 $CHCl_3$/acetone).

Coupling of long chain aniline with protected serine. To a stirring solution of N-Boc-(D)-Serine-OBn (0.740 mmol) in $CH_2Cl_2$ (20 mL) was added PyBOP (0.740 mmol) followed by diisopropylethylamine (0.740 mmol). After 5 minutes of stirring, the aniline (0.740 mmol) was added and stirring was continued for 4 hours. The reaction mixture was then diluted with ethyl acetate (20 mL) and washed with 1 N HCl (3×20 mL), sodium bicarbonate (3×20 mL), and finally brine (1×20 mL), and the organic layer was dried over sodium sulfate.

Solvents were removed under reduced pressure to afford a clear oil, which was purified by flash chromatography to afford the product.

VPC23031: 52%, clear oil, $R_f$=0.35 (dichloromethane).

VPC23019: 90%, clear oil, $R_f$=0.61 (70:30 hexanes/ethyl acetate).

VPC23065, 69: 84%, clear oil, $R_f$=0.82 (90:10 CHCl$_3$/acetone).

VPC23075, 79: 100%, clear oil, $R_f$=0.92 (90:10 CHCl$_3$/acetone).

Benzyl deprotection of coupled product. To a solution of the coupled product (0.667 mmol) in 200 proof ethanol (15 mL) was added a catalytic amount of palladium on activated carbon. To the resulting solution was applied a positive pressure of hydrogen gas and the reaction mixture was stirred 12 hours. The reaction mixture was then filtered through a plug of celite eluting with methanol and then the solvent was removed under reduced pressure to yield the product.

VPC23031: 100%, clear oil, $R_f$=0.27 (70:30 hexanes/ethyl acetate).

VPC23019: 95%, clear oil, $R_f$=0.28 (70:30 hexanes/ethyl acetate).

VPC23065, 69: 89%, clear oil, $R_f$=0.62 (1:1 hexanes/ethyl acetate).

VPC23075, 79: 27%, clear oil, $R_f$=0.43 (1:1 hexanes/ethyl acetate).

Deprotection to afford free alcohol. To a stirred solution of the N-Boc protected alcohol (0.143 mmol) in CH$_2$Cl$_2$ (2 mL) was added trifluoroacetic acid (25.96 mmol) and stirring was continued 4 hours. Under reduced pressure, solvent and excess trifluoroacetic acid were removed affording a brown oil. The oil was rinsed with ether and the solvent was removed under vacuum 5 times to afford the product.

VPC23065: 100%, white solid, $R_f$=0.2 (90:10 CHCl$_3$/methanol).

VPC23075: 93%, white solid, $R_f$=0.2 (90:10 CHCl$_3$/methanol).

Phosphorylation of N-Boc protected alcohol. For phosphorylation, the reaction is performed in the absence of light, work up and columns are completed with as little light as possible. To a solution of the alcohol (0.247 mmol) in 1:1 CH$_2$Cl$_2$/THF (15 in mL) was added tetrazole (0.495 mmol) and the resulting mixture was stirred 30 minutes. Di-tert-butyl-di-isopropylphosphoramidite (0.495 mmol) was then added and the resulting reaction mixture was stirred 15 hours. Hydrogen peroxide (0.989 mmol) was then added and the resulting mixture was then stirred 24 hours, cooled to 0° C., and quenched by addition of aqueous Na$_2$S$_2$O$_5$. The resulting solution was diluted with ethyl acetate (25 mL) and washed with sodium bicarbonate (3×15 mL), ammonium chloride (3×15 mL), and finally brine (1×15 mL). The organic layer was dried over sodium sulfate and the solvent was removed under reduced pressure to afford a clear oil. Flash chromatography provided the product.

VPC23031: 90%, clear oil, $R_f$=0.80 (80:20 ether/ethyl acetate).

VPC23019: 56%, clear oil, $R_f$=0.82 (80:20 ether/ethyl acetate).

VPC23069: 89%, clear oil, $R_f$=0.85 (90:10 ether/ethyl acetate).

VPC23079: 77%, clear oil, $R_f$=0.85 (90:10 ether/ethyl acetate).

Deprotection of N-boc and phosphate groups. To a stirred solution of the protected product (0.162 mmol) in CH$_2$Cl$_2$ (2 mL) was added trifluoroacetic acid (25.96 mmol) and stirring was continued 4 h. Under reduced pressure, solvent and excess trifluoroacetic acid were removed affording a brown oil. Rinsed oil with ether and removed under vacuum 5 times to afford the product.

VPC23031: 100%, clear oil, $R_f$=0 (90:10 CHCl$_3$/methanol).

VPC23019: 92%, clear oil, $R_f$=0 (90:10 CHCl$_3$/methanol).

VPC23069: 86%, clear oil, $R_f$=0 (90:10 CHCl$_3$/methanol).

VPC23079: 100%, clear oil, $R_f$=0 (90:10 CHCl$_3$/methanol).

Scheme 7 Synthesis of (2R) S1P AnalogVPC23087 and 89:

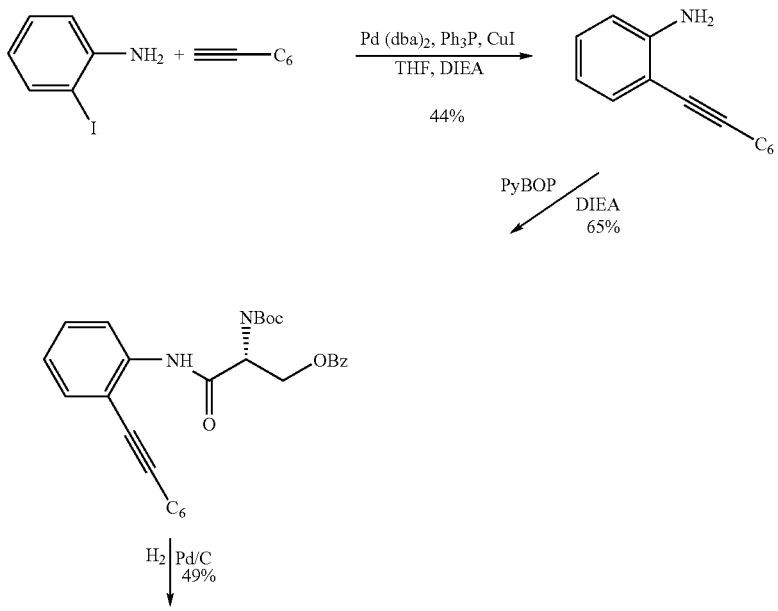

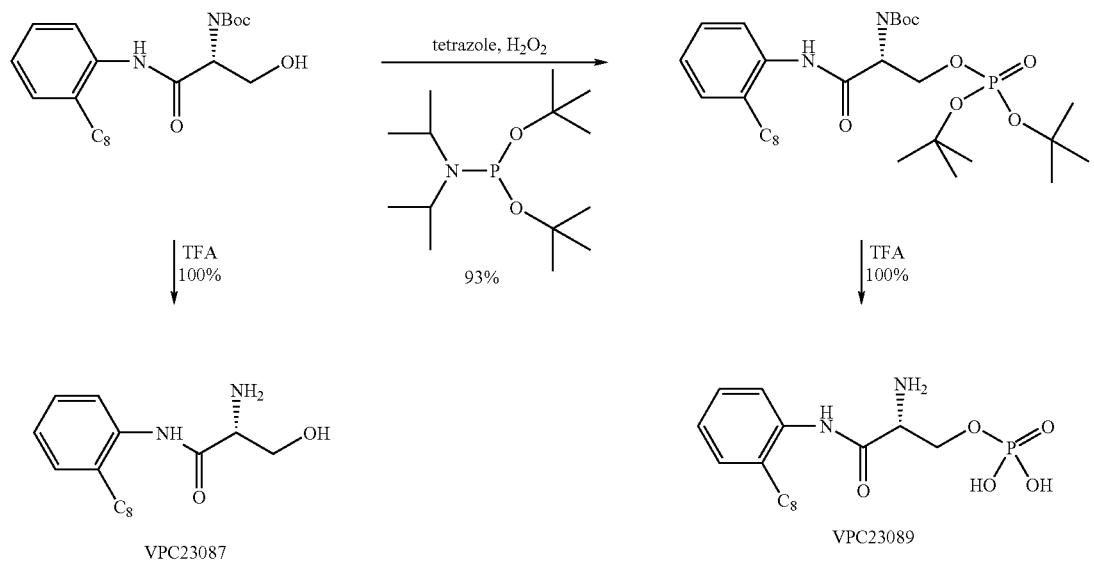

Coupling of aryl halide with terminal alkyne. All starting materials were thoroughly flushed with nitrogen before the reaction. To a stirring solution of the aryl halide (2.01 mmol), bis(dibenzylideneacetone) palladium (0.04 mmol), triphenylphosphine (0.10 mmol), and copper iodide (0.04 mmol) in THF (10 mL) under inert atmosphere was added the terminal alkyne (2.21 mmol) followed by diisopropylethylamine (8.04 mmol). The reaction mixture was then stirred at room temperature for 12 hours. The reaction mixture was then diluted with ethyl acetate (15 mL) and washed with sodium bicarbonate (3×15 mL), ammonium chloride (3×15 mL) and finally brine (1×15 mL). The organic layer was then dried over sodium sulfate. Solvents were removed under reduced pressure to afford a tan oil. Flash chromatography, using 70:30 hexanes/ethyl acetate provided the final product (44%) as a yellow solid. $R_f$=0.79 (70:30 hexanes/ethyl acetate).

Coupling of long chain aniline with protected serine. To a stirring solution of N-boc-(D)-Serine-OBn (0.288 mmol) in CH$_2$Cl$_2$ (10 mL) was added PyBOP (0.288 mmol) followed by diisopropylethylamine (0.288 mmol). After 5 minutes of stirring, the aniline (0.288 mmol) was added and stirring was continued for 4 hours. The reaction mixture was then diluted with ethyl acetate (10 mL) and washed with 1 N HCl (3×10 mL), sodium bicarbonate (3×10 mL), and finally brine (1×10 mL), and the organic layer was dried over sodium sulfate. Solvents were removed under reduced pressure to afford a clear oil. Flash chromatography, using 70:30 hexanes/ethyl acetate provided the final product (65%) as a clear oil. $R_f$=0.64 (70:30 hexanes/ethyl acetate).

Benzyl deprotection and reduction of coupled product. To a solution of the coupled product (0.188 mmol) in 200 proof ethanol (10 mL) was added a catalytic amount of palladium on activated carbon. To the resulting solution was applied a positive pressure of hydrogen gas and the reaction mixture was stirred 12 hours. The reaction mixture was then filtered through a plug of celite eluting with methanol and then the solvent was removed under reduced pressure to yield the crude product as a clear oil. Flash chromatography, using 1:1 hexanes/ethyl acetate provided the final product (49%) as a clear oil. $R_f$=0.51 (1:1 hexanes/ethyl acetate).

Deprotection to afford free alcohol. To a stirred solution of the N-Boc protected alcohol (0.025 mmol) in CH$_2$Cl$_2$ (1 mL) was added trifluoroacetic acid (12.98 mmol) and stirring was continued 4 hours. Under reduced pressure, solvent and excess trifluoroacetic acid were removed affording a brown oil. The oil was rinsed with ether and the solvent was removed under vacuum 5 times to afford the product (100%) as a white solid. $R_f$=0.2 (90:10 CHCl$_3$/methanol).

Phosphorylation of N-Boc protected alcohol. For phosphorylation, reaction is performed in the absence of light, work up and columns are completed with as little light as possible. To a solution of the alcohol (0.092 mmol) in 1:1 CH$_2$Cl$_2$/THF (10 mL) was added tetrazole (0.183 mmol) and the resulting mixture was stirred 30 minutes. Di-tert-butyl-di-isopropylphosphoramidite (0.183 mmol) was then added and the resulting reaction mixture was stirred 15 hours. Hydrogen peroxide (0.367 mmol) was then added and the resulting mixture was then stirred 24 hours, cooled to 0° C., and quenched by addition of aqueous Na$_2$S$_2$O$_5$. The resulting solution was diluted with ethyl acetate (15 mL) and washed with sodium bicarbonate (3×15 mL), ammonium chloride (3×15 mL), and finally brine (1×15 mL). The organic layer was dried over sodium sulfate and the solvent was removed under reduced pressure to afford a clear oil. Flash chromatography, using 90:10 ethyl acetate/ether provided the final product (93%) as a clear oil. $R_f$=0.85 (90:10 ethyl acetate/ether).

Deprotection of N-Boc and phosphate groups. To a stirred solution of the protected product (0.063 mmol) in CH$_2$Cl$_2$ (2 mL) was added trifluoroacetic acid (25.96 mmol) and stirring was continued 4 hours. Under reduced pressure, solvent and excess trifluoroacetic acid were removed affording a brown oil. The oil was rinsed with ether and the solvent was removed under vacuum 5 times to afford the product (100%) as a white solid. $R_f$=0 (90:10 CHCl$_3$/methanol).

Scheme 8 Synthesis of (2R) benzimidazole compound:

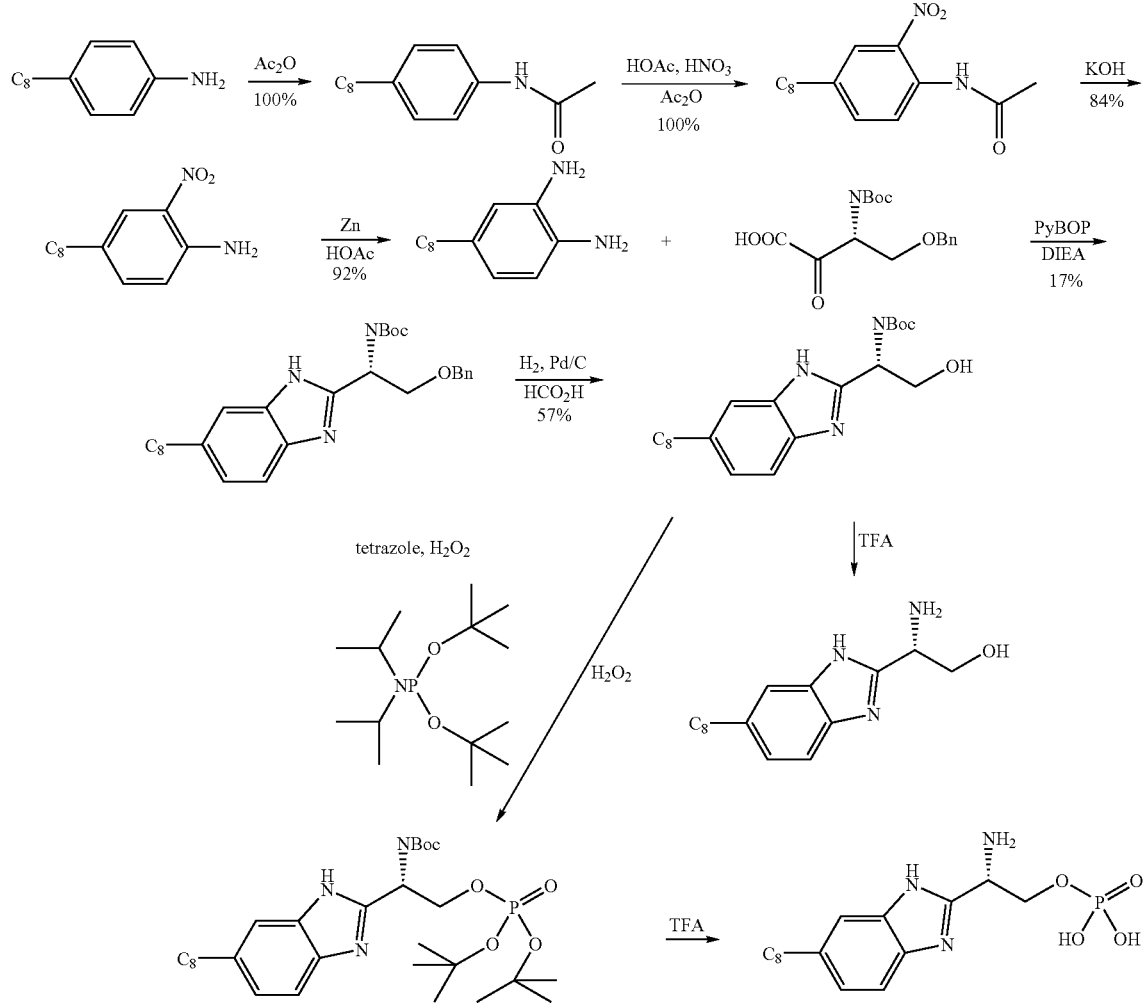

Acetylation of the aniline. To a stirring solution of acetic anhydride (10 mL) under inert atmosphere was added octyl aniline (0.738 mmol) and stirring was continued for 1 hour. Saturated aqueous sodium bicarbonate was then added to neutralize and acetic acid present. The aqueous solution was then extracted with ethyl acetate (3×15 mL) and the combined organic extracts were dried over sodium sulfate and concentrated to afford the final product (100%) as a yellow solid that was used without further purification. $R_f$=0.48 (90:10 CHCl$_3$/acetone).

Nitration of the acetylated aniline. To a stirring solution of acetic acid (1.08 mL), acetic anhydride (0.73 mL), and nitric acid (0.20 mL) at −15° C. under an inert atmosphere was added the acetylated aniline (0.91 mmol) in approx. 1 mL of acetic acid over a period of 3 hours. Reaction mixture was periodically warmed to 0° C. to avoid freezing. The reaction mixture was stirred for an additional hour, and was then diluted with ethyl acetate (10 mL) and neutralized using 1M NaOH and saturated aqueous sodium bicarbonate. The organic layer was removed and the aqueous portion was washed twice more with ethyl acetate (10 mL each). The organic layers were combined and dried over sodium sulfate and then concentrated to a yellow solid. Flash chromatography, using 95:5 CHCl$_3$/acetone provided the final product (100%) as a yellow solid. $R_f$=0.68 (95:5 CHCl$_3$/acetone).

Deacetylation of the aniline. To a stirring solution of the nitrated, acetylated aniline (0.62 mmol) in ethanol (2.5 mL) under an inert atmosphere was added 40% KOH (0.13 mL). The reaction mixture was then heated to reflux for 1 hour. The solution was then cooled in ice and brought to pH=6 using conc. HCl. This mixture was then concentrated to an orange solid and redissolved in ether (10 mL) and washed with saturated aqueous sodium bicarbonate (2×10 mL) and brine (1×10 mL). The organic layer was then dried over sodium sulfate and concentrated to afford the final product (840%) as an orange solid that was used without further purification. $R_f$=0.82 (95:5 CHCl$_3$/acetone).

Reduction of the nitro group. To a stirring solution of the nitrated aniline (0.248 mmol) in acetic acid (5 mL) was added a catalytic amount of zinc dust and stirring was continued overnight under an inert atmosphere. The reaction mixture was then diluted with ether and filtered through a plug of celite under and inert atmosphere using ether to elute. Care was taken not to expose the ether solution to air. The solution was then concentrated to afford the final product (92%) as a reddish-brown oil which was used directly in the next step without further purification. $R_f$=0.05 (95:5 $CHCl_3$/acetone).

Coupling of the diamine with protected serine. A solution of N-boc-(D)-Serine-OBn (0.999 mmol), PyBOP (0.999 mmol), diisopropylethylamine (0.999 mmol) in $CH_2Cl_2$ (25 mL) was stirred 5 min. under an inert atmosphere and then cannulated into a flask containing the diamine (0.999 mmol). This reaction mixture was then stirred 12 hours. The reaction mixture was then diluted with ethyl acetate (30 mL) and washed with saturated aqueous sodium bicarbonate (3×3 mL), ammonium chloride (3×30 mL), and finally brine (1×30 mL), and the organic layer was dried over sodium sulfate. Solvents were removed under reduced pressure to afford a brown oil. Flash chromatography, using 90:10 $CHCl_3$/acetone provided the final product (17%) as a brown oil. $R_f$=0.52 (90:10 $CHCl_3$/acetone).

Benzyl deprotection of coupled product. To a solution of the coupled product (0.167 mmol) in 200 proof ethanol (10 mL) and a catalytic amount of formic acid was added a catalytic amount of palladium on activated carbon. To the resulting solution was applied a positive pressure of hydrogen gas and the reaction mixture was stirred 12 hours. The reaction mixture was then filtered through a plug of celite eluting with methanol and then the solvent was removed under reduced pressure to yield the crude product as a tan oil. Prep. plate thin layer chromatography, using 90:10 $CHCl_3$/acetone provided the final product (57%) as a tan/white solid. $R_f$=0.08 (90:10 $CHCl_3$/acetone).

Deprotection to afford free alcohol. To a stirring solution of the N-Boc protected alcohol (0.008 mmol) in $CH_2Cl_2$ (0.5 mL) was added trifluoroacetic acid (0.5 mL) and stirring was continued 4 hours. Under reduced pressure, solvent and excess trifluoroacetic acid were removed affording a brown oil. The oil was rinsed with ether and the solvent was removed under vacuum 5 times to afford the product (100%) as a tan solid. $R_f$=0.2 (90:10 $CHCl_3$/methanol).

Phosphorylation of N-Boc protected alcohol. For phosphorylation, reaction is performed in the absence of light, work up and columns are completed with as little light as possible. To a solution of the alcohol (0.085 mmol) in 1:1 $CH_2Cl_2$/THF (5 mL) was added tetrazole (0.170 mmol), and the resulting mixture was stirred 30 minutes. Di-tert-butyl-di-isopropylphosphoramidite (0.170 mmol) was then added and the resulting reaction mixture was stirred 15 hours h. Hydrogen peroxide (0.340 mmol) was then added and the resulting mixture was then stirred 4 hours, cooled to 0° C., and quenched by addition of aqueous $Na_2S_2O_5$. The resulting solution was diluted with ethyl acetate (10 mL) and washed with sodium bicarbonate (3×10 mL), ammonium chloride (3×10 mL), and finally brine (1×10 mL). The organic layer was dried over sodium sulfate and the solvent was removed under reduced pressure to afford the product.

Deprotection of N-Boc and phosphate groups. To a stirring solution of the protected product in $CH_2Cl_2$ was added trifluoroacetic acid and stirring was continued 4 hours. Under reduced pressure, solvent and excess trifluoroacetic acid were removed affording a brown oil. The oil was rinsed with ether and the solvent was removed under vacuum 5 times to afford the product.

Example 2

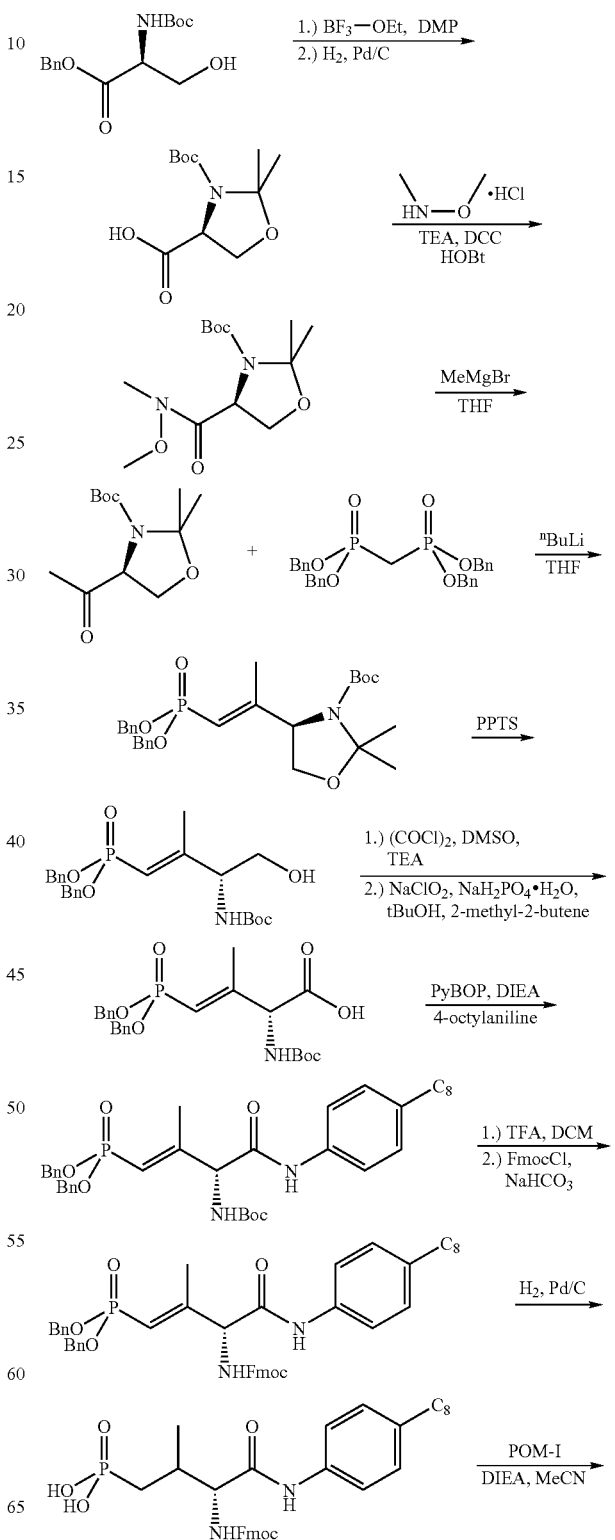

Scheme 9
Synthetic Schemes for Preparation of Phosphate Ester Derivatives

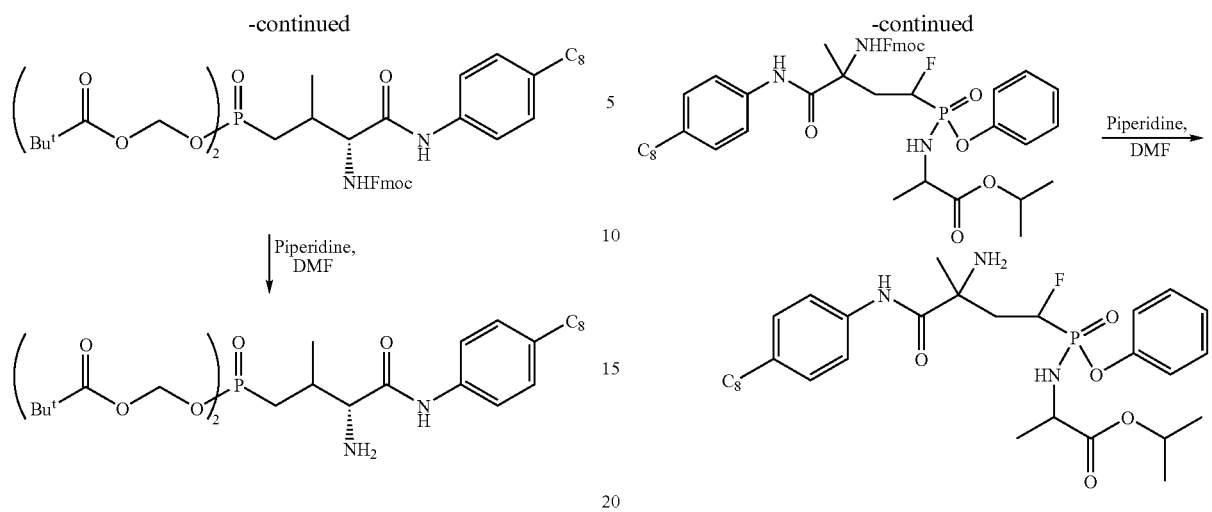
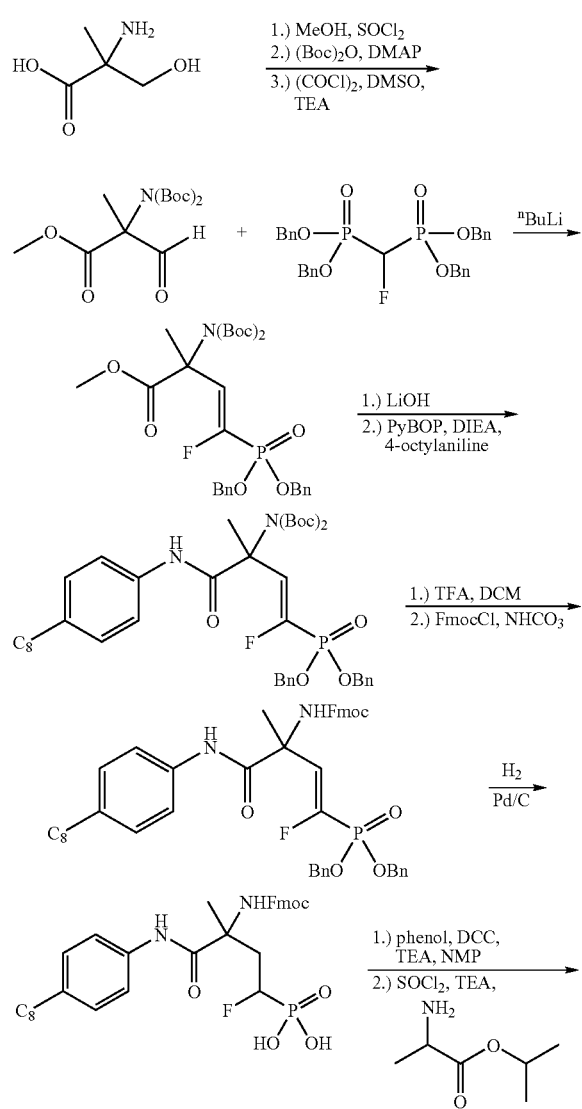
Scheme 10
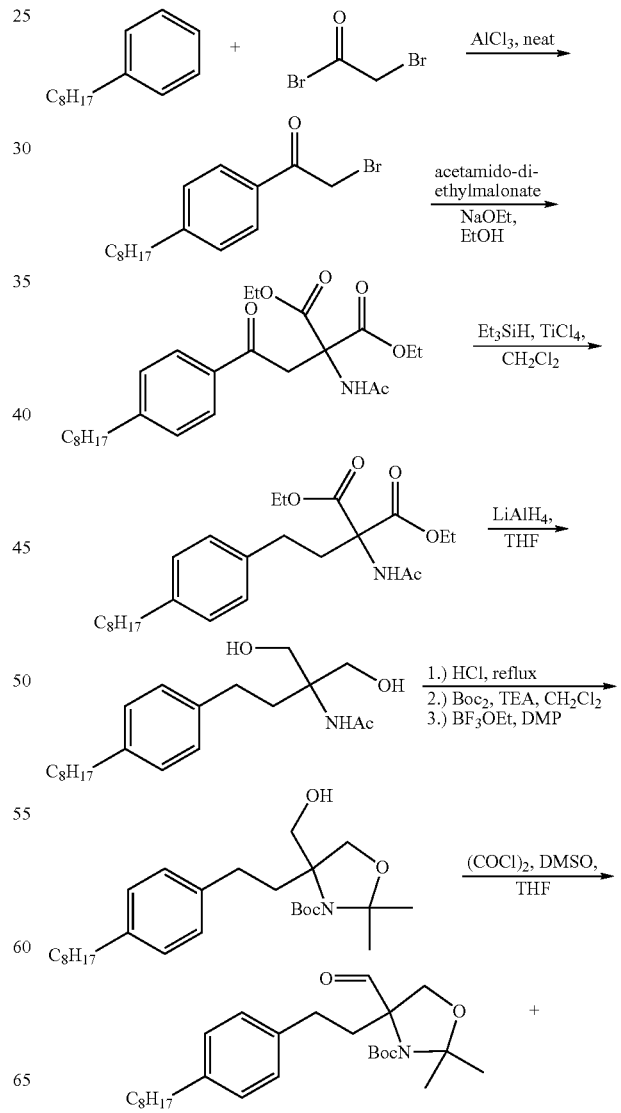
Scheme 11

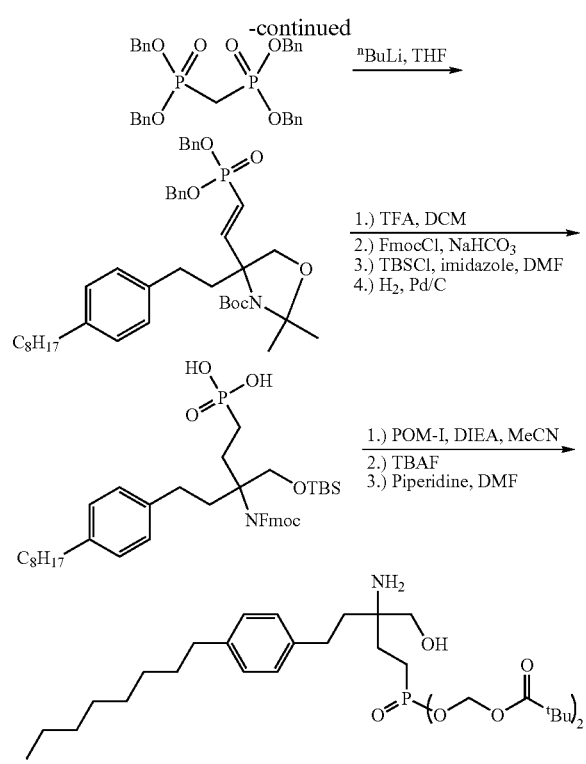

Example 3

All reactions for the synthetic schemes of Example 1 were accomplished using solvents purified by filtration through alumina (activity I) immediately prior to use. All reactions were performed under an inert atmosphere of nitrogen unless otherwise noted. All reagents were purchased from either Aldrich (Milwaukee, Wis.), Sigma (St. Louis, Mo.), Acros (Pittsburgh, Pa.), Advanced ChemTech (Louisville, Ky.), or Novabiochem (La Jolla, Calif.). Merck silica gel F-254 precoated, aluminum backed plates were used for thin layer chromatography (TLC) analysis. Analtech Silica Gel GF 500 or 1000 μM precoated, glass backed plates were used for preparative TLC. Silicycle Ultra Pure Silica Gel (230-400 mesh) or Fisher Scientific Silica Gel 60 Sorbent (230-400 mesh) was used for column chromatography. Each product was analyzed by TLC (single spot) and spectroscopic methods including $^1$H NMR, $^{13}$C NMR, and mass spectrometry. The nuclear magnetic resonance spectra were collected using a General Electric QE300 spectrometer at 300 MHz and chemical shifts are reported in ppm. The assigned structures of the S1P analogs were consistent with all spectral data obtained.

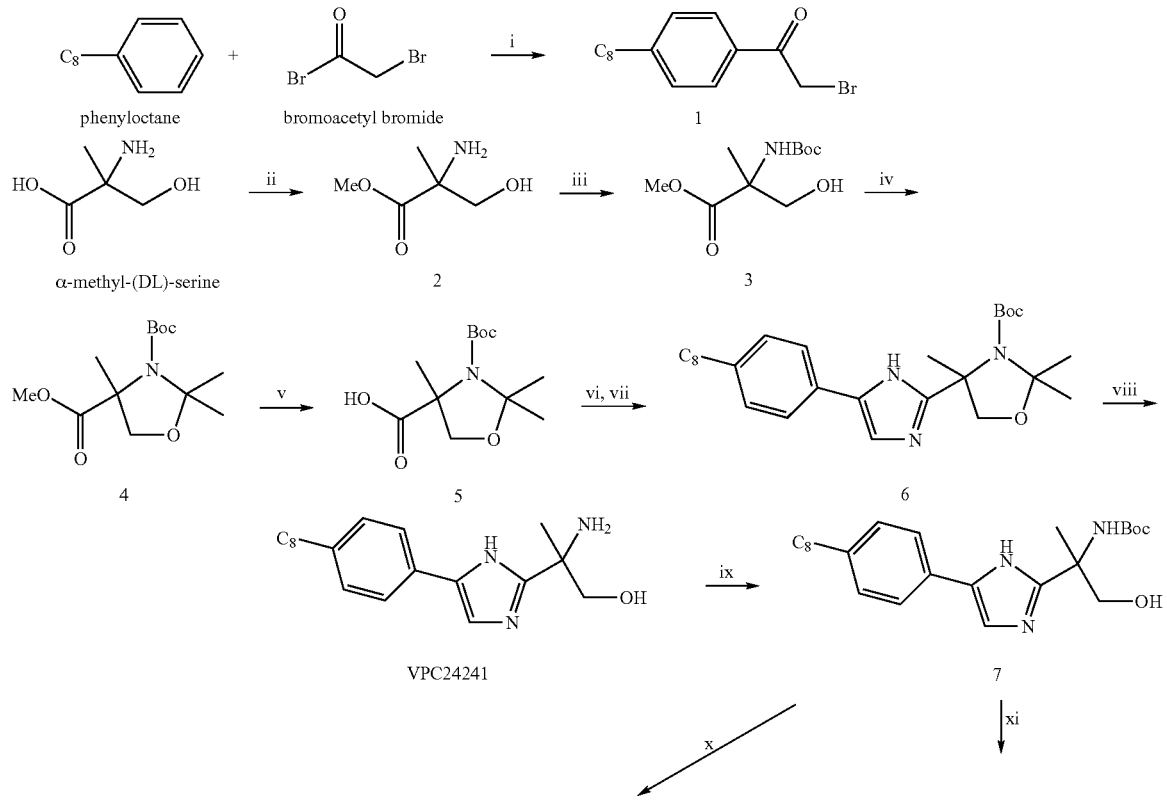

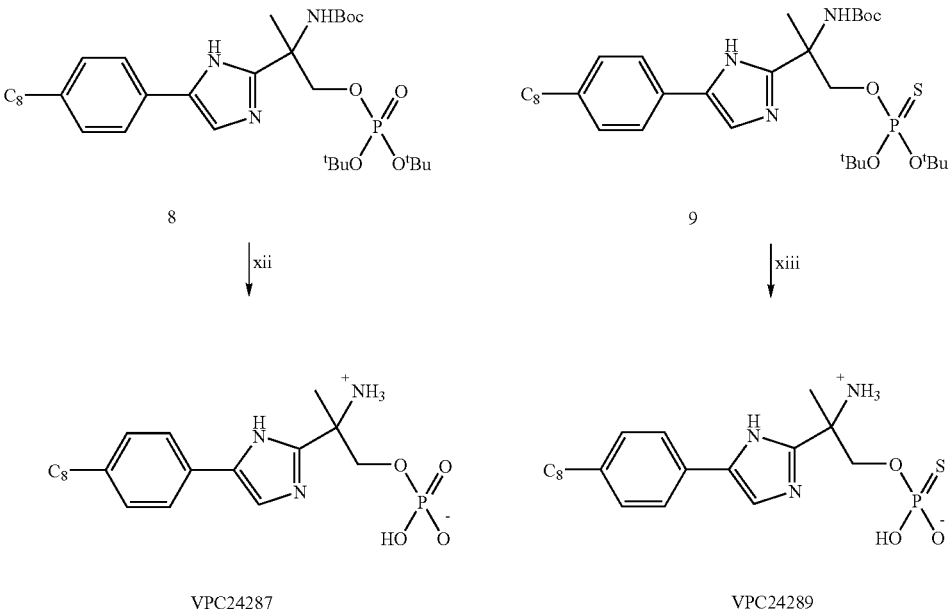

VPC24287            VPC24289

Reagents and Conditions: (i) NaH, THF 0° to room temperature 45 minutes, then Selectfluor 0° to room temperature, overnight, 53%; (ii) SOCl$_2$, MeOH, ROOM TEMPERATURE, 4-6 hours; (iii) Boc$_2$O, TEA, CH$_2$Cl$_2$, room temperature, 4 hours; (iv) 2,2-dimethoxypropane, p-toluenesulfonic acid, CH$_2$Cl$_2$, room temperature, 2 hours, 62% (3 steps) (v) LiCl, NaBH$_4$, EtOH/THF (3:2), 0° to room temperature E, 4 hours, 89%; (vi) PCC, CH$_2$Cl$_2$, room temperature, 6 hours; (vii) DBU, LiCl, CH$_3$CN, room temperature, overnight, 40% (2 steps); (viii) Dowex 50×8, EtOH, room temperature 24 hours, 80%; (ix) PCC, CH$_2$Cl$_2$, room temperature, 6 hours (x) NaClO$_2$, NaH$_2$PO$_4$.H$_2$O, t-butanol, 2-methyl-2-butene; (xi) p-octyl aniline, PyBOP, DIEA, CH$_2$Cl$_2$, room temperature, overnight, (xii) H$_2$, 10% Pd/C, EtOH, room temperature overnight; (xiii) TMSBr, CH$_2$Cl$_2$, room temperature, 4 hours, then 95% CH$_3$OH in H$_2$0, room temperature, 1 hour.

2-Bromo-1-(4-octyl-phenyl)-ethanone (1). To a flame dried round bottom flask equipped with a magnetic stirbar under an inert atmosphere was added AlCl$_3$ (5.47 g, 41 mmol) followed by 1,2-dichloroethane (22 mL). The stirring suspension was then brought to 0° C. and 1-phenyloctane (7.99 mL, 36 mmol) was added in one portion. Bromoacetyl bromide (3.75 mL, 43 mmol) was then added dropwise over a period of 10 minutes. Upon completing addition of the acid bromide, the reaction mixture was brought to room temperature and stirred for 2 hours. The reaction mixture was then quenched carefully by slow addition of H$_2$O (36 mL) without ever letting the reaction mixture exceed 45° C. producing a suspension of solid white precipitate. The aqueous layer of the quenched reaction mixture was discarded and the organic phase was washed once with 10% HCl (10 mL), washed once with H$_2$O (10 mL), and dried over magnesium sulfate. The dried organic phase was then concentrated in vacuo to a green/brown oil. Recrystallization from MeOH/H$_2$O provided the product 1 (6.36 g, 57%) as white needles in three crops. R$_f$=0.21 (1:19 EtOAc/hexanes).

2-Amino-3-hydroxy-2-methyl-propionic acid methyl ester (2). A stirring solution of α-methyl-DL-Serine (1 g, 8.39 mmol) in MeOH (40 mL) in a flame dried round bottom flask under an inert atmosphere was cooled to 0° C. and SOCl$_2$ (1.84 mL, 25.19 mmol) was slowly added. After addition of the SOCl$_2$ was complete, the reaction mixture was stirred 12 hours at room temperature and then concentrated in vacuo to a white solid that was used directly in the next reaction.

2-tert-Butoxycarbonylamino-3-hydroxy-2-methyl-propionic acid methyl ester (3). To the crude product obtained in the above reaction was slowly added sat. aq. NaHCO$_3$ (12.5 mL) followed by solid NaHCO$_3$ (500 mg) and the reaction mixture was stirred 30 minutes under an inert atmosphere. THF (12.5 mL) was then added to the reaction mixture followed by di-tert-butyl dicarbonate (1.83 g, 8.39 mmol) and stirring at room temperature was continued for 12 hours. The reaction mixture was then diluted with H$_2$O (20 mL) and extracted with EtOAc (3×20 mL). The combined EtOAc extracts were dried over sodium sulfate and concentrated in vacuo to a thick white paste. To this paste was added hexanes which produced 3 (630 mg, 32% for 2 steps) as a white precipitate which was collected by filtration. R$_f$=0.35 (1:1 EtOAc/hexanes).

2,2,4-Trimethyl-oxazolidine-3,4-dicarboxylic acid 3-tert-butyl ester 4-methyl ester (4). To a stirring solution of 3 (9.342 g, 40 mmol) in acetone (15 mL) in a flame dried round bottom flask under an inert atmosphere was added 2,2-dimethoxypropane (66 mL). To this solution was added BF$_3$.OEt$_2$ (0.30 mL, cat.) and stirring was continued at room temperature for 2 hours. The reaction mixture was then concentrated in vacuo to an orange oil which was purified by flash chromatography to provide 4 (9.392 g, 85%) as a white solid. R$_f$=0.55 (1:3 EtOAc/hexanes). Compound was observed as an uneven mixture of rotomers.

2,2,4-Trimethyl-oxazolidine-3,4-dicarboxylic acid 3-tert-butyl ester (5). To a stirring solution of 4 (9.392 g, 34 mmol) in THF (65 mL) and H$_2$O (35 mL) under an inert atmosphere was added solid LiOH.H$_2$O (1.426 g, 34 mmol) in one portion. The reaction mixture was heated to 90° C. and stirred 8 hours at which point the reaction mixture was cooled to room temperature. The crude reaction mixture was washed with Et$_2$O (3×50 mL) and the Et$_2$O extracts were discarded. The aqueous solution was then acidified with 2M KHSO$_4$ until a white precipitate began to form on addition, pH=5. The acid was added dropwise until the precipitate persisted and the aqueous solution was extracted with Et$_2$O (50 mL). After extraction, two addition drops of acid were added to the aqueous layer and it was again extracted with Et$_2$O (25 mL). The Et$_2$O extracts were combined and quickly back extracted with 1M NaOH (15 mL). The organic phase was then dried over sodium sulfate and concentrated in vacuo to give 5 (7.458 g, 85%) as a white solid which was used without further purification. Compound was observed as an uneven mixture of rotomers.

2,2,4-Trimethyl-4-[5-(4-octyl-phenyl)-1H-imidazol-2-yl]-oxazolidine-3-carboxylic acid tert-butyl ester (6). To a flame dried round bottom flask equipped with a magnetic stirbar under an inert atmosphere was added 5 (3.00 g, 11.6 mmol) followed by absolute EtOH (33 mL) and Cs$_2$CO$_3$ (1.93 g, 5.9 mmol). This mixture was then shaken 30 minutes at which time all of the suspended Cs$_2$CO$_3$ had disappeared. The reaction mixture was then concentrated in vacuo to a white solid at which time DMF (60 mL) was added. To the stirring solution was added a solution of 1 (3.60 g, 11.6 mmol) in DMF (5 mL). The resulting solution was stirred 4 hours and concentrated to a light brown solid. To the light brown solid was added EtOAc (50 mL) and the suspended CsBr was filtered off and washed with EtOAc. The filtrate was then concentrated to a light brown foam which was subsequently dissolved in xylenes (195 mL) in a round bottom flask equipped with a Dean-Stark trap (filled with xylenes) and a reflux condenser. To this solution was added NH$_4$OAc (1.74 g, 22.6 mmol) and the reaction mixture was brought to 105° C. and stirred 3 h at which time the reaction would progress no further. The crude reaction mixture was then concentrated in vacuo to a red oil. To the oil was added EtOAc (200 mL) and this solution was washed with saturated aqueous NaHCO$_3$ (3×50 mL) followed by brine solution (1×50 mL). The organic phase was then dried over sodium sulfate and concentrated to a red oil which was subjected to flash chromatography to give 6 (1.074 g, 20%) as a white solid. R$_f$=0.45 (6:4 Et$_2$O/petroleum ether).

2-Amino-2-[5-(4-octyl-phenyl)-1H-imidazol-2-yl]-propan-1-ol (VPC24241). To a flame dried round bottom flask equipped with a magnetic stirbar under an inert atmosphere was added 6 (973 mg, 2.07 mmol) followed by MeOH (20 mL) and p-TsOH.H$_2$O (1.22 g, 6.42 mmol). This mixture was then heated to reflux, stirred 3 hours, cooled to 0° C., and quenched by slow addition of saturated aqueous NaHCO$_3$ (20 mL). This solution was then diluted with EtOAc (30 mL) and the aqueous layer was discarded. The organic phase was washed with saturated aqueous NaHCO$_3$ (1×20 mL), washed with 1M NaOH (1×20 mL), dried over sodium sulfate, and concentrated to an orange oil. To this oil was added Et$_2$O which produced VPC24241 (408 mg, 60%) as a white precipitate which was collected by filtration.

{2-Hydroxy-1-methyl-1-[5-(4-octyl-phenyl)-1H-imidazol-2-yl]-ethyl}-carbamic acid tert-butyl ester (7). To a vigorously stirring solution of VPC24241 (70 mg, 0.213 mmol) in THF (4 mL) and H$_2$O (2 mL) was added Na$_2$CO$_3$ (198 mg, 1.87 mmol) followed by di-tert-butyl dicarbonate (214 mg, 0.98 mmol) and the resulting solution was stirred 12 h at room temperature. The reaction mixture was then diluted with EtOAc (20 mL) and washed with saturated aqueous NaHCO$_3$ (2×15 mL). The organic phase was dried over sodium sulfate and concentrated in vacuo to a clear oil which solidified to a white solid under vacuum. This white solid was then subjected to flash chromatography to produce 7 (52 mg, 57%) as a white solid. R$_f$=0.50 (1:1 EtOAc/hexanes).

{2-(Di-tert-butoxy-phosphoryloxy)-1-methyl-1-[5-(4-octyl-phenyl)-1H-imidazol-2-yl]-ethyl}-carbamic acid tert-butyl ester (8). To a solution of 7 (33 mg, 0.077 mmol) in 1:1 CH$_2$Cl$_2$/THF (3 mL) was added a 3% solution of tetrazole in acetonitrile (0.44 mL, 0.154 mmol) and the resulting mixture was stirred 30 minutes. Di-tert-butyl-di-isopropylphosphoramidite (0.05 mL, 0.154 mmol) was then added and the resulting reaction mixture was stirred 12 h. To this solution was added 30% hydrogen peroxide (0.04 mL, 0.308 mmol) and the resulting mixture was stirred 3 hours, cooled to 0° C., and quenched by addition of aqueous Na$_2$S$_2$O$_5$. The resulting solution was diluted with ethyl acetate (10 mL) and washed with saturated aq. NaHCO$_3$ (2×5 mL). The organic layer was dried over sodium sulfate and the solvent was removed under reduced pressure to afford a clear oil. Flash chromatography, using 1:1 EtOAc/hexanes, provided 8 (22 mg, 46%) as a clear oil. R$_f$=0.45 (1:1 EtOAc/hexanes):

{2-(Di-tert-butoxy-thiophosphoryloxy)-1-methyl-1-[5-(4-octyl-phenyl)-1H-imidazol-2-yl]-ethyl}-carbamic acid tert-butyl ester (9). To a solution of 7 (19 mg, 0.044 mmol) in 1:1 CH$_2$Cl$_2$/THF (2 mL) was added a 3% solution of tetrazole in acetonitrile (0.26 mL, 0.089 mmol) and the resulting mixture was stirred 30 min. Di-tert-butyl-di-isopropylphosphoramidite (0.03 mL, 0.089 mmol) was then added and the resulting reaction mixture was stirred 12 hours. To this solution was added elemental sulfur (excess) and the resulting mixture was stirred 12 hours. The resulting solution was diluted with ethyl acetate (7 mL) and washed with saturated aq. NaHCO$_3$ (2×3 mL). The organic layer was dried over sodium sulfate and the solvent was removed under reduced pressure to afford a clear oil with yellow tint. Flash chromatography, using 1:3 EtOAc/hexanes, provided 9 (13 mg, 46%) as a clear oil. R$_f$=0.40 (1:3 EtOAc/hexanes).

Phosphoric acid mono-{2-amino-2-[5-(4-octyl-phenyl)-1H-imidazol-2-yl]-propyl}ester (VPC24287). To a stirring solution of 8 (22 mg, 0.035 mmol) in CH$_2$Cl$_2$ (1 mL) was added trifluoroacetic acid (1 mL) and stirring was continued 4 hours. Solvent and excess trifluoroacetic acid were removed in vacuo to afford a brown oil. The oil was diluted with ether and concentrated in vacuo 5 times on a rotary evaporator to afford a white solid which was placed in a fritted funnel and washed with cold ether producing VPC24287 (13 mg, 91%) as a powdery white solid. R$_f$=0 (4:1 CHCl$_3$/methanol).

Thiophosphoric acid O-{2-amino-2-[5-(4-octyl-phenyl)-1H-imidazol-2-yl]-propyl}ester (VPC24289). To a stirring solution of 9 (13 mg, 0.020 mmol) in CH$_2$Cl$_2$ (1 mL) was added benzenethiol (0.042 mL, 0.40 mmol) followed by bromotrimethyl silane (0.05 mL, 0.40 mmol) and finally trifluoroacetic acid (1 mL) and stirring was continued 6 hours. To quench the reaction mixture, water (0.5 mL) was added and the resulting solution was stirred 30 minutes. Solvent and excess reagents were removed in vacuo to afford a brown oil. The oil was diluted with ether and concentrated in vacuo 5 times on a rotary evaporator to afford a light tan solid which was placed in a fritted funnel and washed with cold ether and a small amount of cold water producing VPC24289 (8 mg, 94%) as a powdery white solid. R$_f$=0 (4:1 CHCl$_3$/metha.

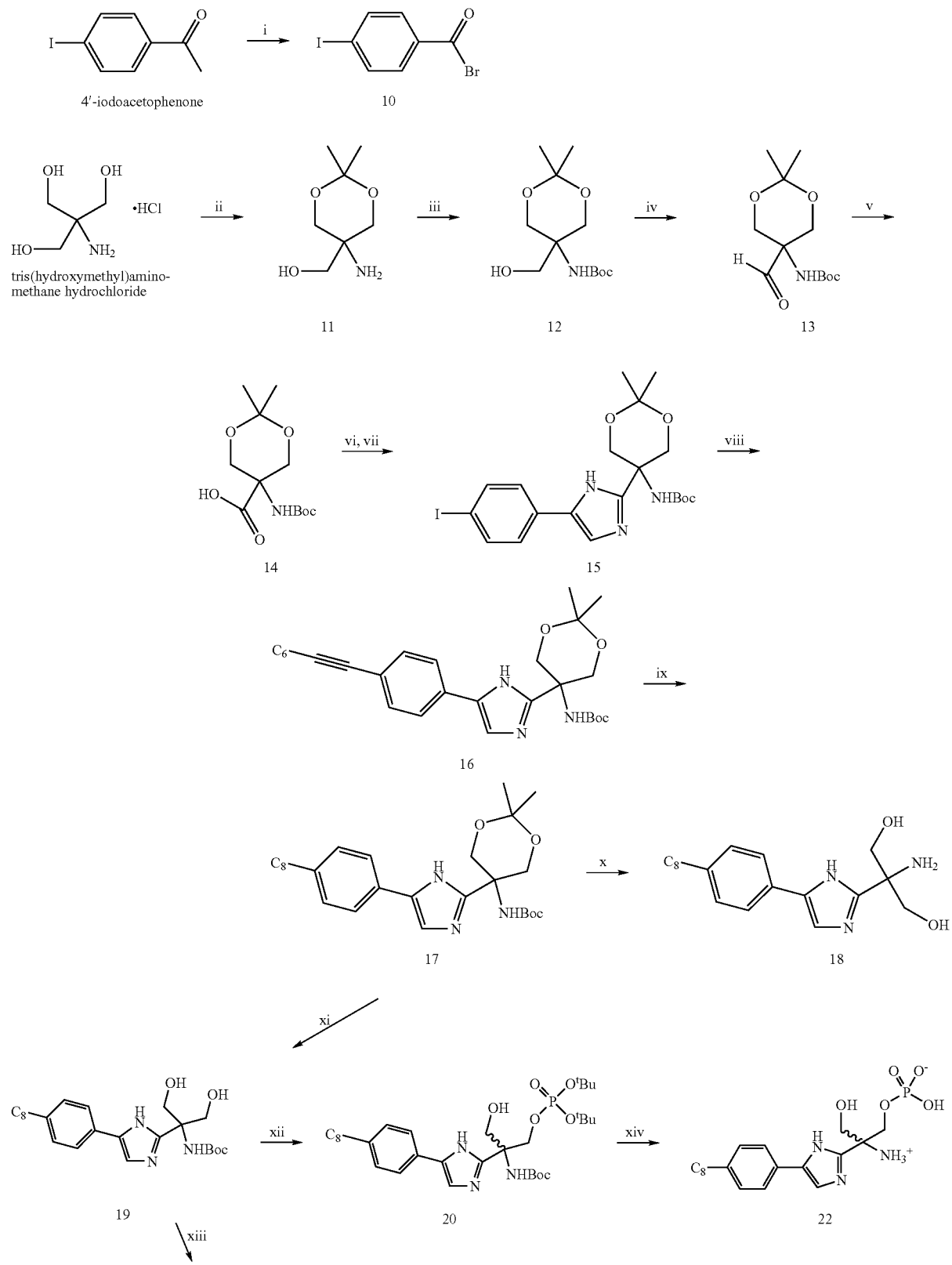

-continued

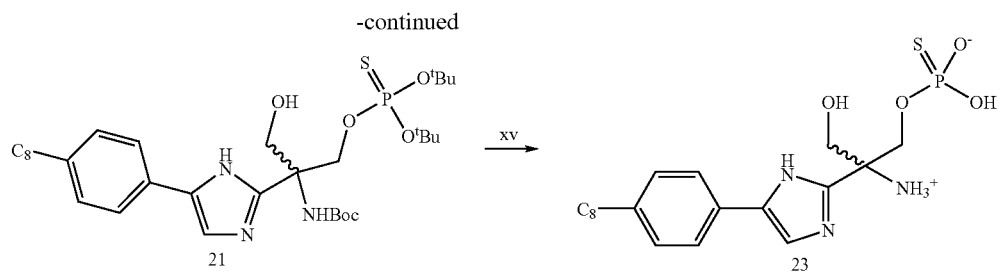

Reagents and Conditions: (i) Br₂, 1:1 dioxane/ether, CH₂Cl₂, room temperature, 1 hour, 66%; (ii) 2,2-DMP, p-TsOH, DMF, room temperature, 12 hours, TEA, room temperature, 10 minutes (iii) (Boc)₂O, NaHCO₃, THF/H₂O, room temperature, 12 hours, 69% (2 steps); (iv) (COCl)₂, DMSO, TEA, CH₂Cl₂, −78° C. to room temperature, 4 hours, 74%; (v) NaClO₂, NaH₂PO₄·H₂O, 2-methyl-2-butene, ᵗBuOH/H₂O, room temperature, 1 hours, 95%; (vi) Cs₂CO₃, EtOH, room temperature, 1 hour; 1, DMF, room temperature, 12 hours; (vii) NH₄OAc, xylenes, 110° C., 12 hours, 36% (2 steps); (viii) Pd(dba)₂, Ph₃P, CuI, DIEA, THF, room temperature, 12 hours, 68%; (ix) H₂, 10% Pd/C, EtOH, room temperature, 12 hours; (x) 1:1 TFA/CH₂Cl₂, room temperature, 6 hours; (xi) DOWEX 50×8, EtOH, room temperature, 12 hours; (xii) tetrazole, di-tert-butyl diisopropylphosphoramidite, CH₂Cl₂/THF, room temperature, 12 hours; H₂O₂, room temperature, 3 hours; (xiii) tetrazole, di-tert-butyl diisopropylphosphoramidite, CH₂Cl₂/THF, room temperature, 12 hours; S₈, room temperature, 3 hours (xiv) 1:1 TFA/CH₂Cl₂, room temperature, 4 hours; (xv) benzenethiol, TMSBr, 1:1 TFA/CH₂Cl₂, room temperature, 4 hours.

Scheme 14
Synthetic Scheme for Synthesis of Alpha Substituted Phosphonate Compounds

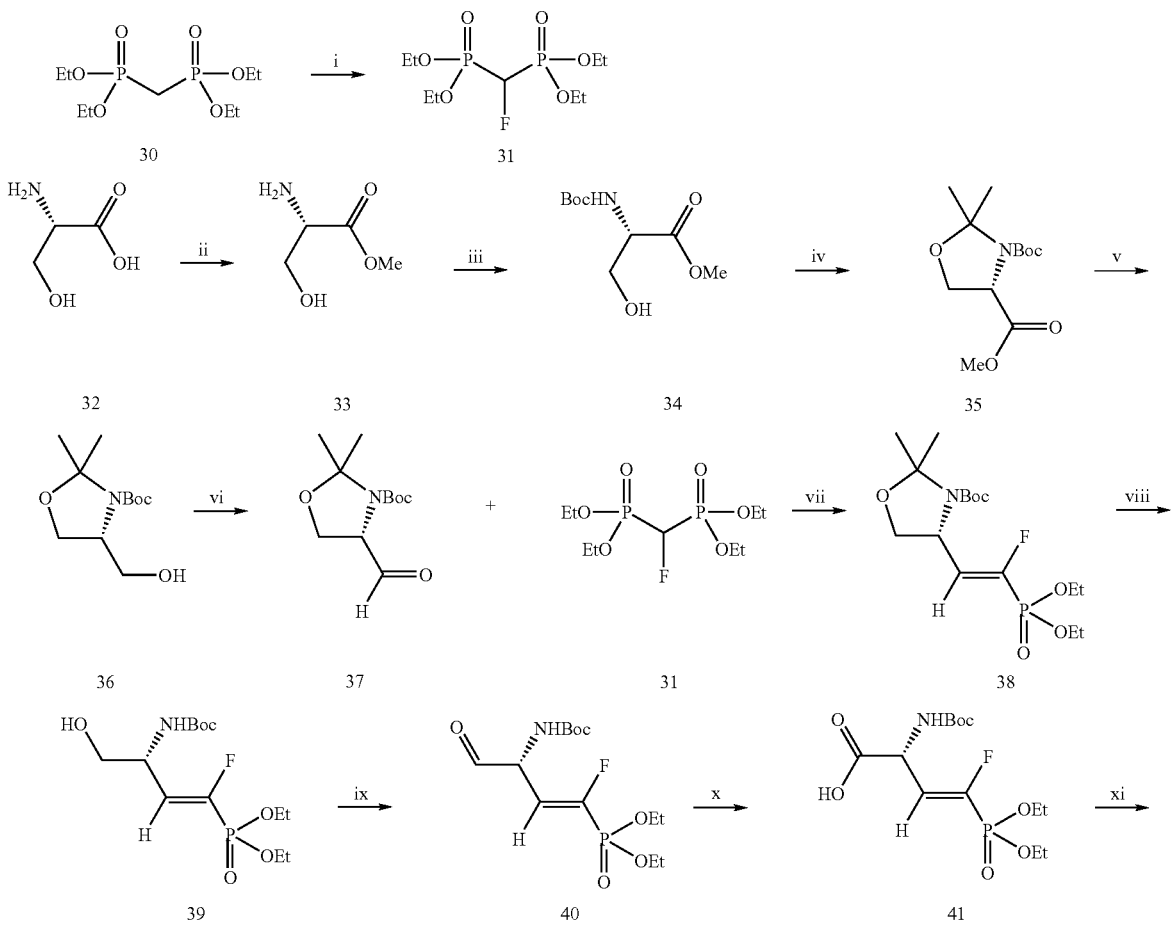

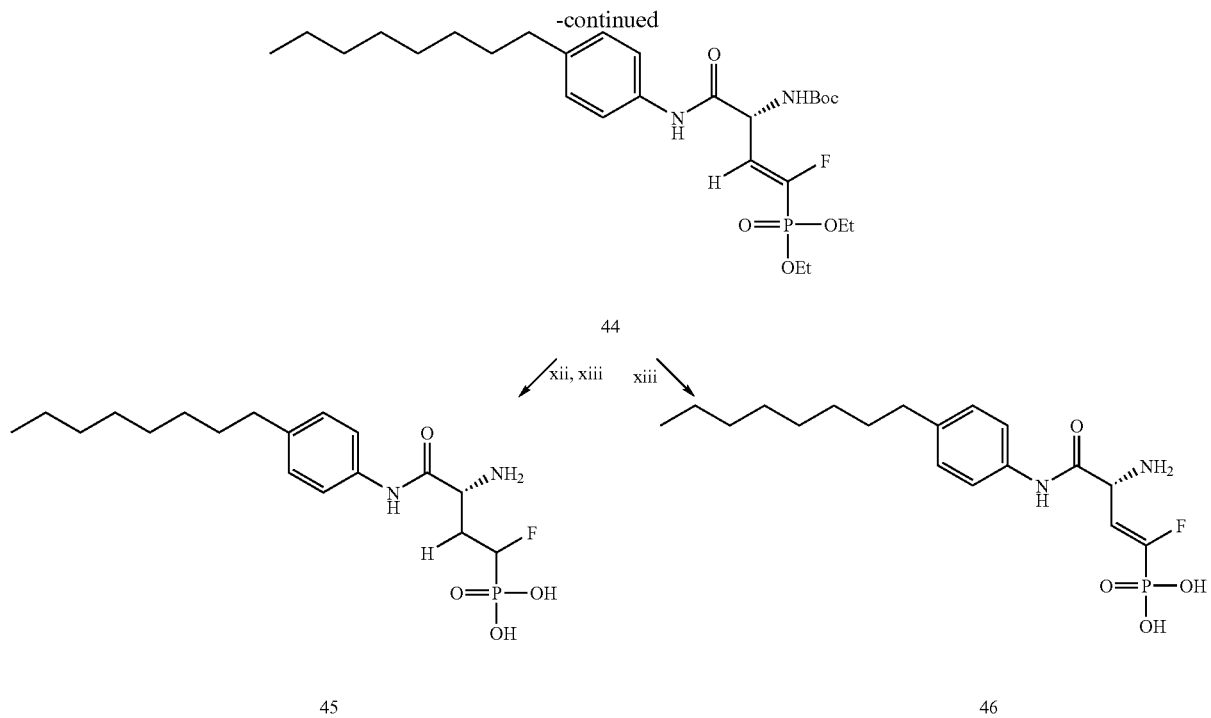

44

45

46

Reagents and Conditions: (i) NaH, THF 0° to room temperature 45 minutes, then Selectfluor 0° to room temperature, overnight, 53%; (ii) SOCl$_2$, MeOH, room temperature, 4-6 hours; (iii) Boc$_2$O, TEA, CH$_2$Cl$_2$, room temperature, 4 hours; (iv) 2,2-dimethoxypropane, p-toluenesulfonic acid, CH$_2$Cl$_2$, room temperature, 2 hours, 62% (3 steps) (v) LiCl, NaBH$_4$, EtOH/THF (3:2), 0° to room temperature, 4 hours, 89%; (vi) PCC, CH$_2$Cl$_2$, room temperature, 6 hours; (vii) DBU, LiCl, CH$_3$CN, room temperature, overnight, 40% (2 steps); (viii) Dowex 50×8, EtOH, room temperature 24 hours, 80%; (ix) PCC, CH$_2$Cl$_2$, room temperature, 6 hours; (x) NaClO$_2$, NaH$_2$PO$_4$.H$_2$O, t-butanol, 2-methyl-2-butene; (xi) p-octyl aniline, PyBOP, DIEA, CH$_2$Cl$_2$, room temperature, overnight; (xii) H$_2$, 10% Pd/C, EtOH, room temperature overnight; (xiii) TMSBr, CH$_2$Cl$_2$, room temperature, 4 hours, then 95% CH$_3$OH in H$_2$0, room temperature, 1 hour.

[(Diethoxy-phosphoryl)-fluoro-methyl]-phosphonic acid diethyl ester (31). To a slurry of 95% NaH (9 mg, 0.375 mmol) in THF (1.5 mL) was added tetraethyl methylene diphosphonate, (30) (100 mg, 0.347 mmol) at 0° C. The mixture was allowed to warm to room temperature and stirred for 45 minutes. The mixture was subsequently cooled to 0° C. and Selectfluor (153 mg, 0.432 mmol) was added in one portion. The mixture was allowed to warm to room temperature and stirred for 1 hour. The reaction mixture was concentrated in vacuo and purified by column chromatography on SiO$_2$ (3% MeOH in EtOAc) to yield 56 mg (53%) of a clear liquid.

2-Amino-3-hydroxy-propionic acid methyl ester (33). To a solution of D-serine (5 g, 47.58 mmol) in methanol (100 mL), stirring under N$_2$ $_{(g)}$ at 0° C., was added thionyl chloride (20.8 mL, 285.5 mmol) dropwise. The reaction mixture was allowed to warm to room temperature, stirred for 4-6 hours, and then concentrated under reduced pressure. The crude material was reconstituted in Et$_2$O and concentrated, in the same manner. This was repeated numerous times until SOCl$_2$ could not be detected. The crude material was confirmed by NMR experiments and carried on to the following step.

2-tert-Butoxycarbonylamino-3-hydroxy-propionic acid methyl ester (34). To a solution of the crude methyl ester serine (33) in CH$_2$Cl$_2$ (100 mL), stirring under N$_2$ $_{(g)}$, was added di-tert-butyl pyrocarbonate (11.420 g, 52.34 mmol) and triethyl amine (16.6 mL, 118.95 mmol). The reaction mixture was allowed to stir at room temperature for 4 hours, and then poured over NH$_4$Cl at 0° C. The organic layer was extracted with 10% HCl (2×), then NaHCO$_3$ and brine. The organic layer was then dried over anhydrous Na$_2$SO$_4$, filtered and concentrated under reduced pressure. The crude material was again carried on to the following step.

2,2-Dimethyl-oxazolidine-3,4-dicarboxylic acid 3-tert-butyl ester 4-methyl ester (35). To a solution of (34) in CH$_2$Cl$_2$, stirring under nitrogen at 0° C., was added 2,2-dimethoxypropane (29.5 mL, 237.9 mmol) and p-toluene sulfonic acid monohydrate (9.050 g, 47.58 mmol). The mixture was removed from the ice bath after 15 minutes and stirred at room temperature for 1.5 hours. The reaction mixture was poured into 50 mL of saturated NaHCO$_3$ (aq) and extracted with diethyl ether (3×50). The organic layer was extracted with NaHCO$_3$ and brine, then dried over anhydrous MgSO$_4$, filtered and concentrated under reduced pressure. The crude material was purified by flash chromatography on SiO$_2$ (1:1 EtOAc/Hexanes) to yield 7.659 g (62%, 3 steps) of a clear liquid.

4-Hydroxymethyl-2,2-dimethyl-oxazolidine-3-carboxylic acid tert-butyl ester (36). To a mixture of NaBH$_4$ (2.247 g, 59.08 mmol) and LiCl (2.505 g, 59.08 mmol) in EtOH (42 mL), stirring under nitrogen at 0° C., was added (35) (7.659 g, 29.54 mmol) in THF (30 mL) dropwise. This mixture was allowed to warm to room temperature and continued stirring for 48 hours. The precipitate was filtered and washed with ethanol. The washings were concentrated and extracted with EtOAc. The organic layer was then washed with brine and dried over anhydrous $Na_2SO_4$. Column chromatography on $SiO_2$ (1:1 EtOAc/Hexanes) was utilized to purify 6.101 g (89%) of the title compound as a white solid.

4-Formyl-2,2-dimethyl-oxazolidine-3-carboxylic acid tert-butyl ester (37). To a solution of (36) (80 mg, 0.346 mmol) stirring in $CH_2Cl_2$ (2 mL), under a nitrogen atmosphere, was added pyridinium chlorochromate (150 mg, 0.694 mmol). The reaction mixture was allowed to stir overnight then filtered through a plug of silica gel. The crude aldehyde was carried on to the following step.

4-[2-(Diethoxy-phosphoryl)-2-fluoro-vinyl]-2,2-dimethyl-oxazolidine-3-carboxylic acid tert-butyl ester (38). To a stirred suspension of LiCl (18 mg, 0.416 mmol) in dry acetonitrile (3.5 mL), under nitrogen at room temperature, were added diphosphonate (31) (127 mg, 0.416 mmol), DBU (0.05 mL, 0.347 mmol) and garner's aldehyde (37) (80 mg, 0.347 mmol). The reaction mixture was allowed to stir overnight then concentrated in vacuo. The crude material was isolated by column chromatography on $SiO_2$, (1:1 EtOAc/Hexanes) to yield 47 mg (40%, two steps) of a clear liquid.

(3-tert-Butoxycarbonylamino-1-fluoro-4-hydroxy-but-1-enyl)-phosphonic acid diethyl ester (39). To compound (38) (47 mg, 0.123 mmol) stirring in EtOH (1 mL) was added Dowex 50×8 (150 mg), which was washed with EtOH and dried. The reaction was allowed to stir under nitrogen and at room temperature for 24 hours. The reaction mixture was filtered and the precipitate washed with excess EtOH, then concentrated in vacuo. The crude material was purified by column chromatography on $SiO_2$ (1:1 EtOAc/Hexanes) to yield 34 mg of the expected product.

Example 4

[γ-$^{35}$S]GTP Binding Assay for Measuring S1P Activity

Transient Expression in HEK293T Cells.

Human or mouse S1P5 DNA was mixed with an equal amount of DNA encoding a rat Gi2R protein as well as DNAs encoding cow β1 and γ2 proteins and used to transfect monolayers of HEK293T cells using the calcium phosphate precipitate method. After 60 hours, cells were harvested, and microsomes were prepared, aliquoted, and stored at −70° C. until use.

[γ-$^{35}$S]GTP Binding.

Briefly, 5 μg of membranes from S1P expressing HEK293T cells was incubated in 0.1 mL of binding buffer (in mM: HEPES 50, NaCl 100, $MgCl_2$ 5), pH 7.5, containing 5 μg of saponin, 10 μM GDP, 0.1 nM [γ-$^{35}$S]GTP (1200 Ci/mmol), and test lipid. After incubating for 30 minutes at 30° C., bound radionuclide was separated from free by filtration through Whatman GF/C paper using a Brandel Cell Harvester (Gaithersburg, Md.).

Stable Expression in RH7777 Cells.

Rat hepatoma RH7777 cell monolayers were transfected with human or mouse S1P5/pCR3.1 DNA using the calcium phosphate precipitate method, and clonal populations expressing the neomycin phosphotransferase gene were selected by addition of geneticin (G418) to the culture medium. The RH7777 cells were grown in monolayers at 37° C. in a 5% $CO_2$/95% air atmosphere in growth medium consisting of 90% MEM, 100% fetal bovine serum, 2 mM glutamine, and 1 mM sodium pyruvate.

Measurement of cAMP Accumulation.

Assay of cAMP accumulation was performed as described previously (See Im et al., J. Biol. Chem. 275, 14281-14286 (2000), the disclosure of which is incorporated herein). Assays were conducted on populations of $5 \times 10^5$ cells stimulated with 1 μM forskolin in the presence of the phosphodiesterase inhibitor isomethylbutylxanthine (IBMX, 1 mM) for 15 minutes. cAMP was measured by automated radioimmunoassay. The GTPγS studies were performed using zebrafish S1P1 overexpressed rat RH-7777 and human hS1P1, hS1P2, hS1P3 and hS1P5 overexpressed human HEK293 cells. Table 1 shows the $EC_{50}$ values for each of the S1P analogs at S1P receptors: S1P1, S1P2, S1P3 and S1P5. In addition to testing the human S1P receptors (hS1P1, hS1P2, hS1P3 and hS1P5), a zebrafish S1P receptor (zS1P1) and mouse S1P (mS1P5) were also tested.

TABLE 1

$EC_{50}$ Values (nM) for S1P Analogues at Recombinant S1P Receptors

| | $zS1P_1$ | $hS1P_1$ | $hS1P_3$ | $hS1P_2$ | $hS1P_5$ | $mS1P_5$ |
|---|---|---|---|---|---|---|
| S1P | 54.6 | 0.9 | 1.1 | 2.9 | 43.9 | 12.7 |
| VPC22041 | 2053.0 | 598.4 | 845.4 | 973.2 | 645.5 | >5000 |
| VPC22051 | >5000 | 322.1 | 601.9 | 2760.0 | >5000 | >5000 |
| VPC22053 | >5000 | 397.0 | 862.4 | 2685.0 | 1606.0 | 2006.0 |
| VPC22063 | >5000 | 1805.0 | 878.6 | >5000 | 1220.0 | 1326.0 |
| VPC22135 | 1625.0 | 12.7 | 50.8 | 2107.0 | >5000 | 1821.0 |

S1P increases GTPγS binding significantly (2-5-fold) at each receptor with $EC_{50}$ values from 1 to 55 nM. The synthetic series consisted of five dihydro S1P of the general formula:

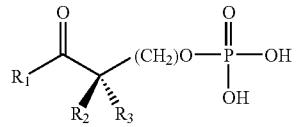

wherein

VPC22041 (2S): $R_1$ is $NH(CH_2)_{11}CH_3$, $R_2$ is $NH_2$ and $R_3$ is H;

VPC22053 (2S): $R_1$ is $O(CH_2)_{13}CH_3$, $R_2$ is $NH_2$ and $R_3$ is H;

VPC22051 (2S): $R_1$ is $NH(CH_2)_{13}CH_3$, $R_2$ is $NH_2$ and $R_3$ is H;

VPC22063 (2S): $R_1$ is $NH(CH_2)_{15}CH_3$, $R_2$ is $NH_2$ and $R_3$ is H; and VPC22135 (2R): $R_1$ is $NH(CH_2)_{13}CH_3$, $R_2$ is H and $R_3$ is $NH_2$.

The amide-containing compounds contained alkyl chains of 12 (VPC22041), 14 (VPC22053), or 16 (VPC22063) carbons, and the 2'-amino group was in the natural configuration (S), except for VPC22135, wherein the 2'-amino was in the (R) configuration. VPC22053 and VPC22135 are an enantiomeric pair, while VPC22051 is the ester-containing equivalent of VPC22053 (see Scheme 4). All of these compounds had significant agonist activity at each of the S1P receptors, although none were as potent as S1P itself (see Table 1). In particular, on the S1P5 transfected HEK293 cells, the five mimetics showed $EC_{50}$'s of approximately 1 □M, where as the $EC_{50}$ of S1P itself on the same cells is closer to 10 nM. However, one compound, VPC22135, approached the potency of S1P at both the human S1P1 and human S1P3 receptors. Curiously, this compound has the amino group in the unnatural (R) configuration. Its enantiomer, VPC22053, was more than 1 log order less potent at both the S1P1 and S1P3 receptors. The results obtained for the S1P1 transfected RH-7777 cells showed a preference for binding with the 18 carbon backbone mimetic compounds (identical to S1P) over the 16 and 20 carbon backbone mimetic compounds.

Assay of phenyl imidazole compounds vpc24287 (phosphate) and vpc24289 phosphothionate) at individual human sphingosine 1-phosphate (S1P) receptors was also conducted.

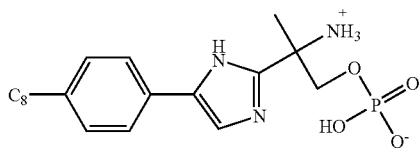

VPC24287

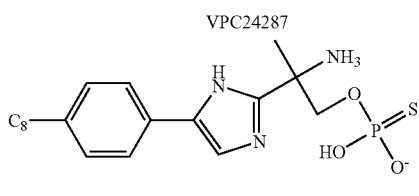

VPC24289

Methods:

Human recombinant S1P receptor type DNAs were mixed with DNAs encoding human Gαi2, cow β1 and cow γ2 proteins and introduced into cultured HEK293T cells by transfection. After about 48 hours, cells were harvested and crude membranes prepared. Ligand driven binding of a non-hydrolyzable GTP analog, GTP[γ-$^{35}$S], was measured in a rapid filtration assay. Details of the assay are found in: Brinkmann, V., Davis, M. D., Heise, C. E., Albert, R., Cottens, W., Hof, R., Bruns, C., Prieschl, E., Baumruker, T., Hiestand, P., Foster, C. and Lynch, K. R. The immune modulator, FTY720, targets sphingosine 1-phosphate receptors (J. Biol. Chem. 277: 21453-21457, 2002). Total counts per minute were determined for S1P, vpc24287 and vpc24289 activation of the S1P receptor subtypes with the maximal counts received by S1P designated as 100% activation of the S1P receptor. The results are provided in FIG. 6A-6D demonstrating vpc24287 and vpc24289 activation of the S1P receptor subtypes relative to S1P.

Example 5

Biological Assay of the Synthesized Mimetics

An additional series of compounds was tested using the GTP$_\gamma$S binding assay described in Example 2 and in Im et al., J. Biol. Chem. 275, 14281-14286 (2000), the disclosure of which is incorporated herein). The compounds tested for binding at human S1P receptors (hS1P1, hS1P2, hS1P3, hS1P4 and hS1P5) have the general structure:

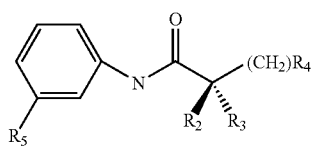

wherein for

VPC23019: $R_5$ is $(CH_2)_7CH_3$, $R_2$ is H, $R_3$ is $NH_2$ and $R_4$ is phosphate;

VPC23031: $R_5$ is $(CH_2)_7CH_3$, $R_2$ is H, $R_3$ is $NH_2$ and $R_4$ is phosphate;

VPC23065: $R_5$ is $(CH_2)_9CH_3$, $R_2$ is H, $R_3$ is $NH_2$ and $R_4$ is hydroxy;

VPC23069: $R_5$ is $(CH_2)_9CH_3$, $R_2$ is H, $R_3$ is $NH_2$ and $R_4$ is phosphate;

VPC23075: $R_5$ is $(CH_2)_8CH_3$, $R_2$ is H, $R_3$ is $NH_2$ and $R_4$ is hydroxy;

VPC23079: $R_5$ is $(CH_2)_8CH_3$, $R_2$ is H, $R_3$ is $NH_2$ and $R_4$ is phosphate;

or have the general structure:

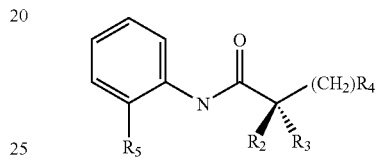

wherein for

VPC23087: $R_5$ is $(CH_2)_7CH_3$, $R_2$ is H, $R_3$ is $NH_2$, and $R_4$ is hydroxy;

VPC23089: $R_5$ is $(CH_2)_7CH_3$, $R_2$ is H, $R_3$ is $NH_2$ and $R_4$ is phosphate;

Each of the compounds tested (VPC 23019, 23031, 23065, 23069, 23087, 23089, 23075, 23079) failed to show significant activity at the S1P2 receptor. Compounds VPC23065, VPC23087 and VPC23075 are primary alcohols and thus lack the phosphate headgroup. Yet several of these compounds exhibit activity at S1P receptors (See FIGS. 2A, 2B, 2C, 3A, 3B, 3C, and 4C) and each of these compounds shows good agonist activity at the S1P4 receptor.

Figure 2A:
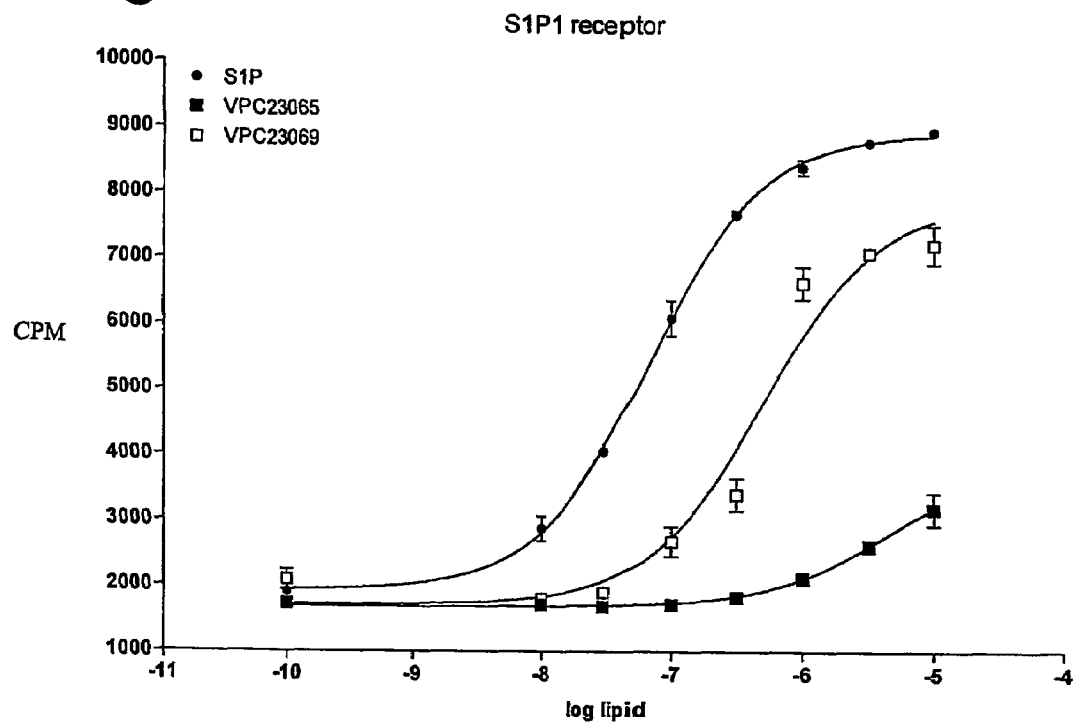
FIG. 2A-2E are graphic representations of [γ-$^{35}$S]GTP binding to HEK293T cell membranes (containing different S1P receptors) in response to S1P, VPC23065 and VPC23069.
Figure 2B:
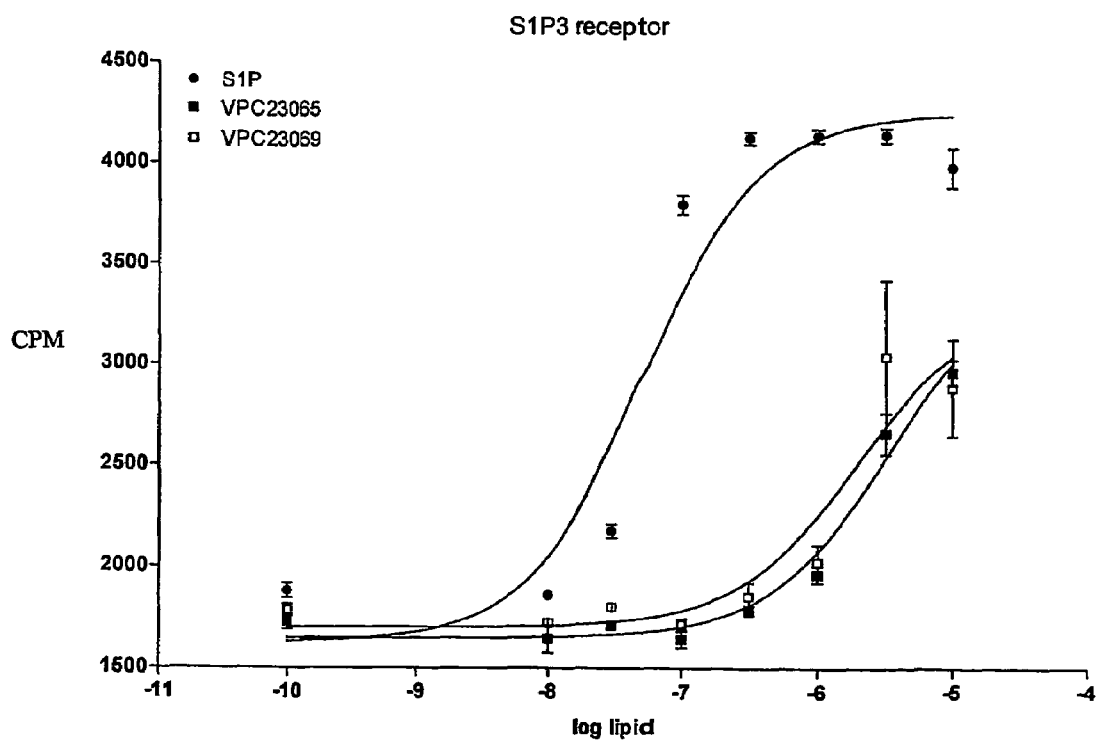
Figure 2C:
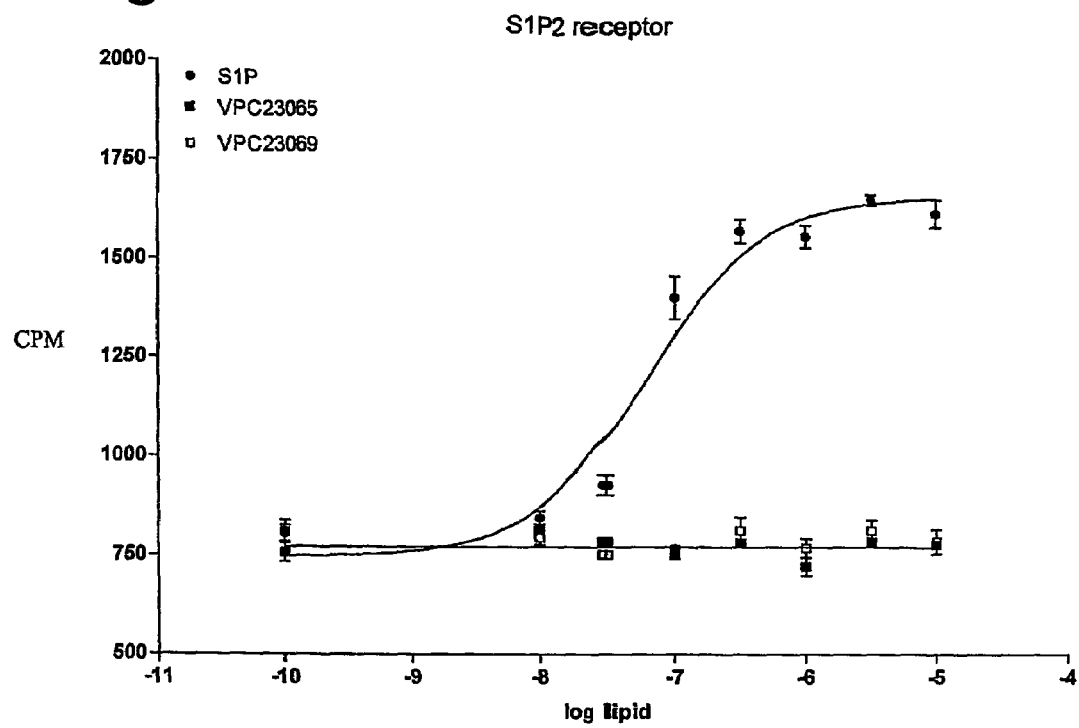
Figure 2D:
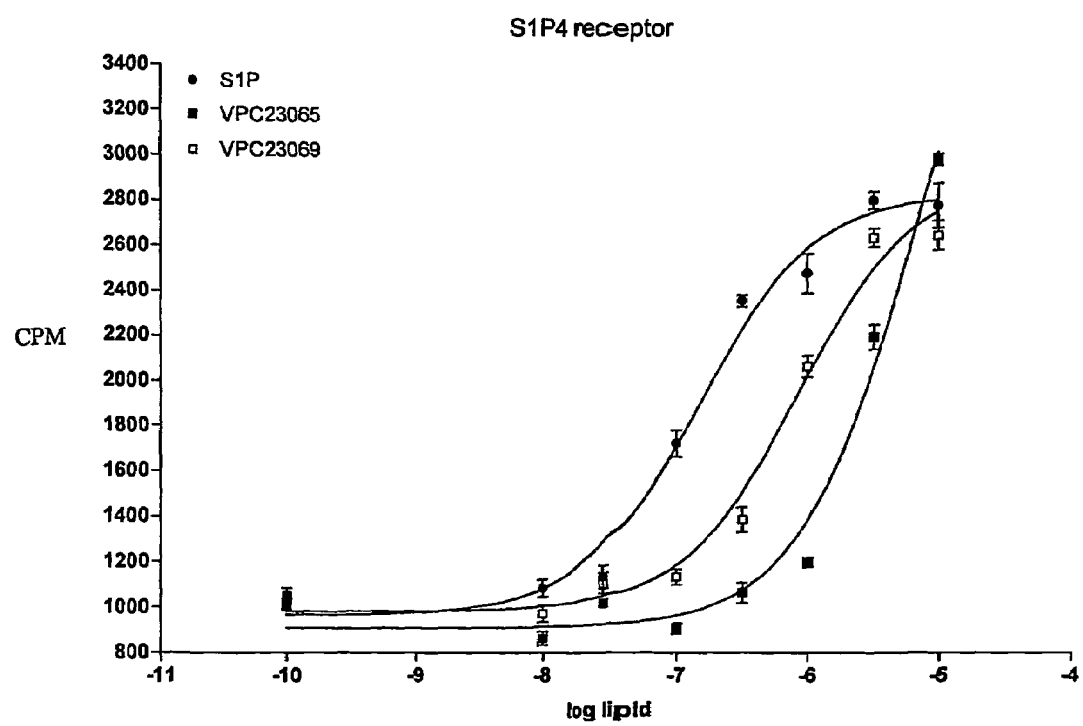
Figure 2E:
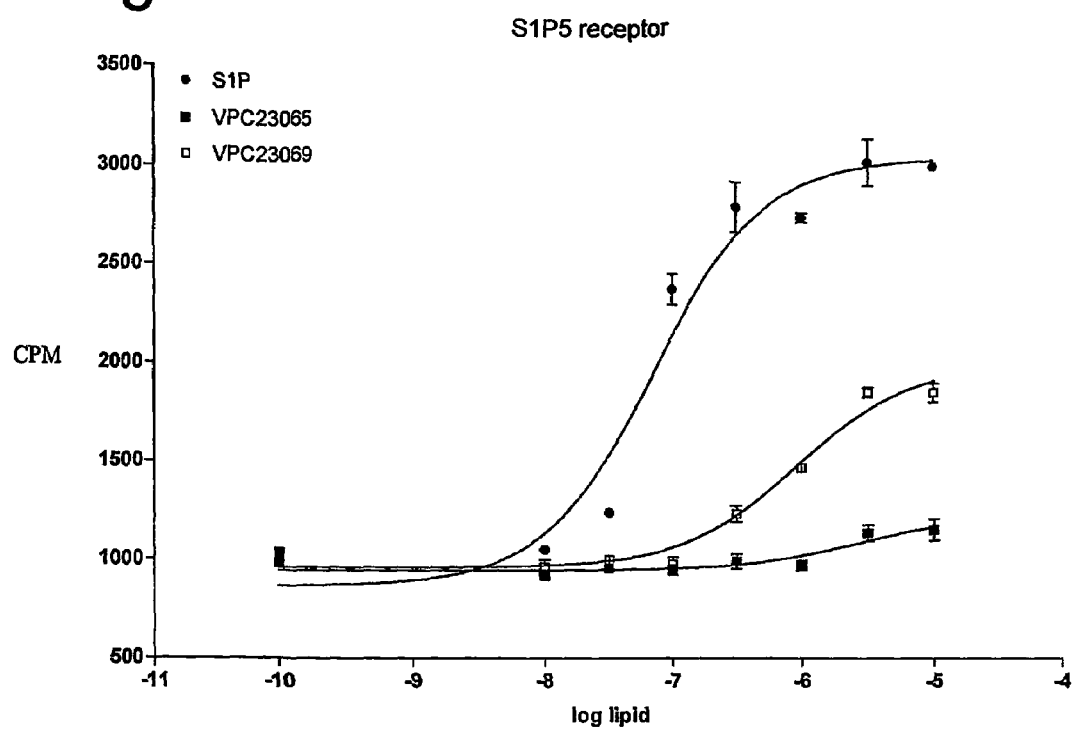
Figure 3A:
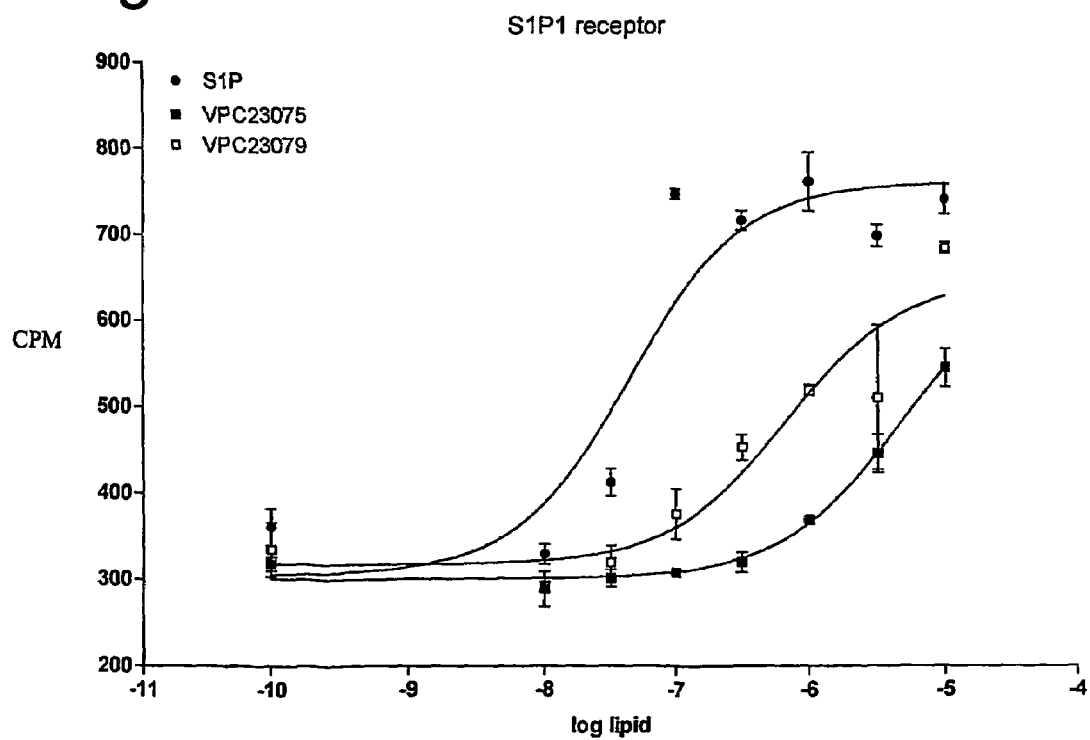
FIG. 3A-3E are graphic representations of [γ-$^{35}$S]GTP binding to HEK293T cell membranes (containing different S1P receptors) in response to S1P, VPC23075 and VPC23079.
Figure 3B:
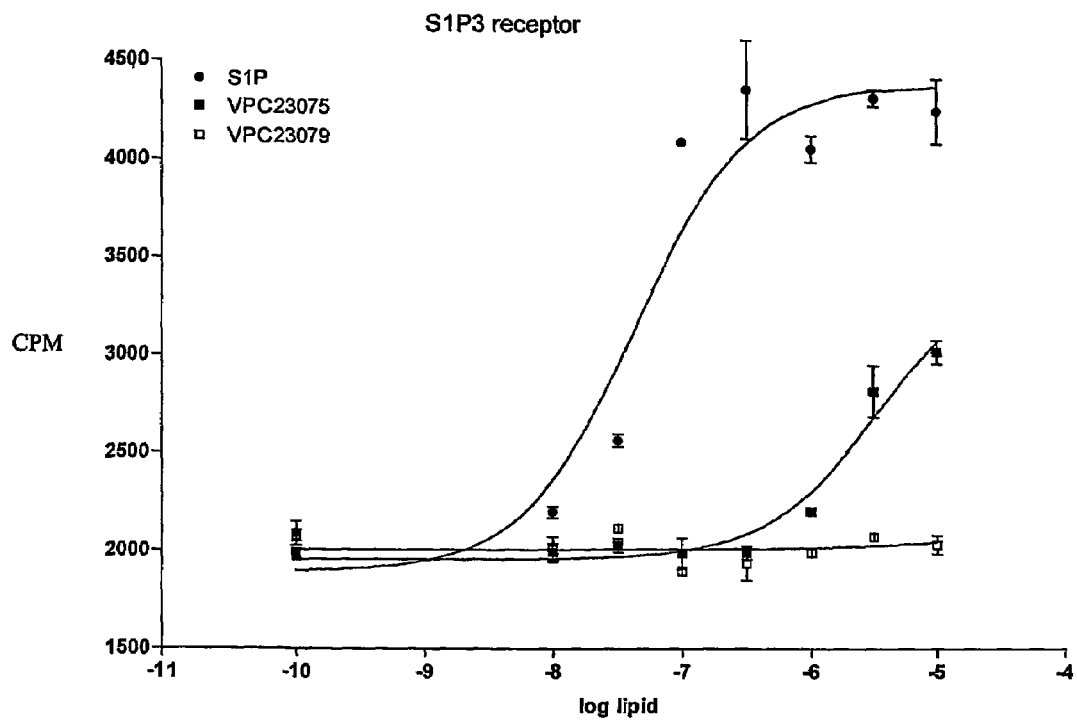
Figure 3C:
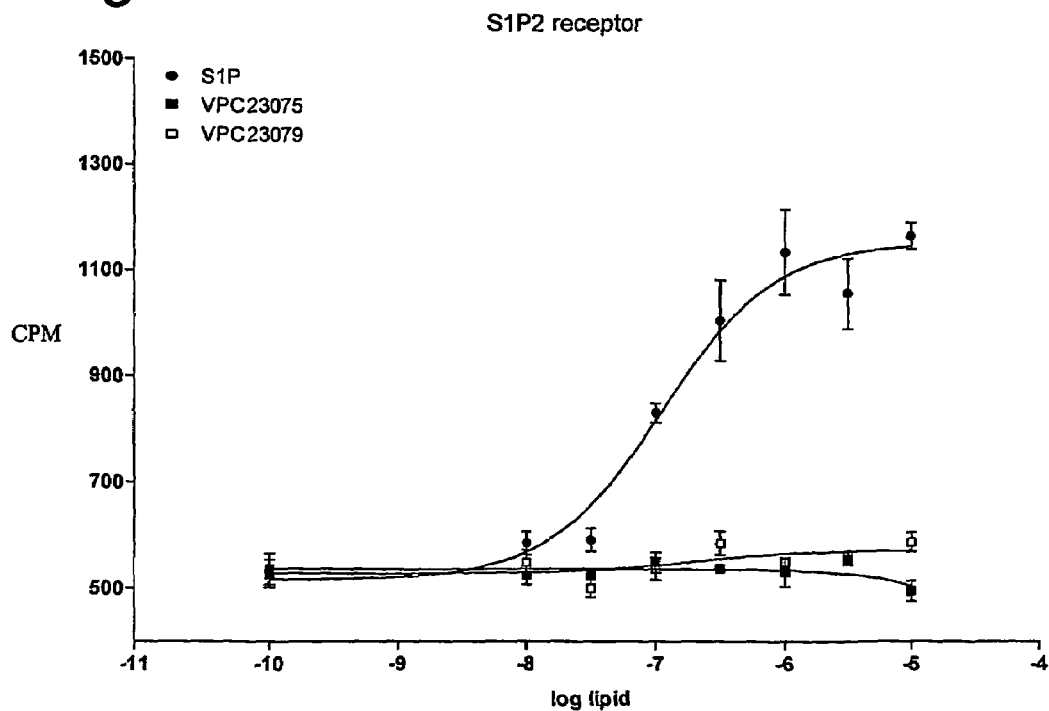
Figure 3D:
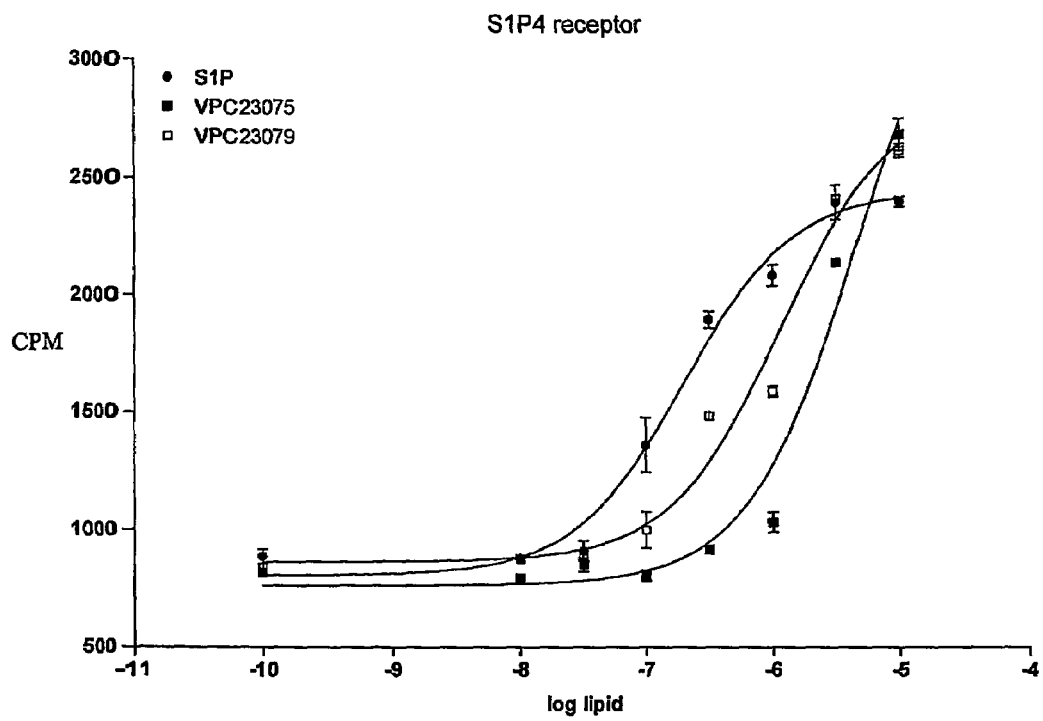
Figure 3E:
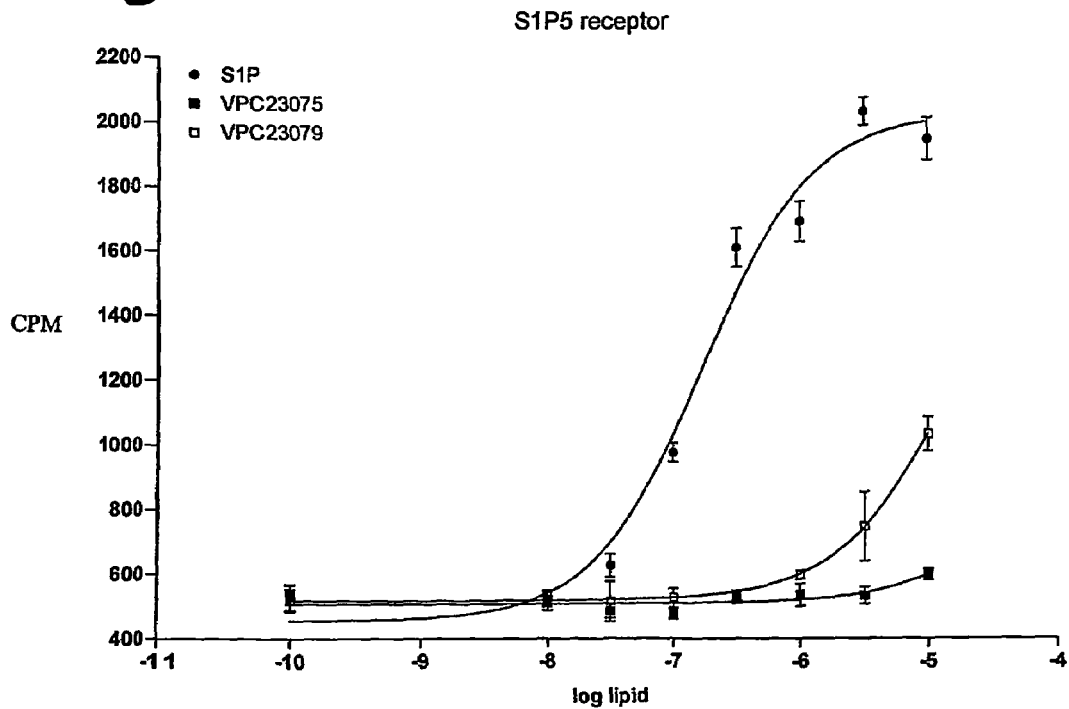
Figure 4A:
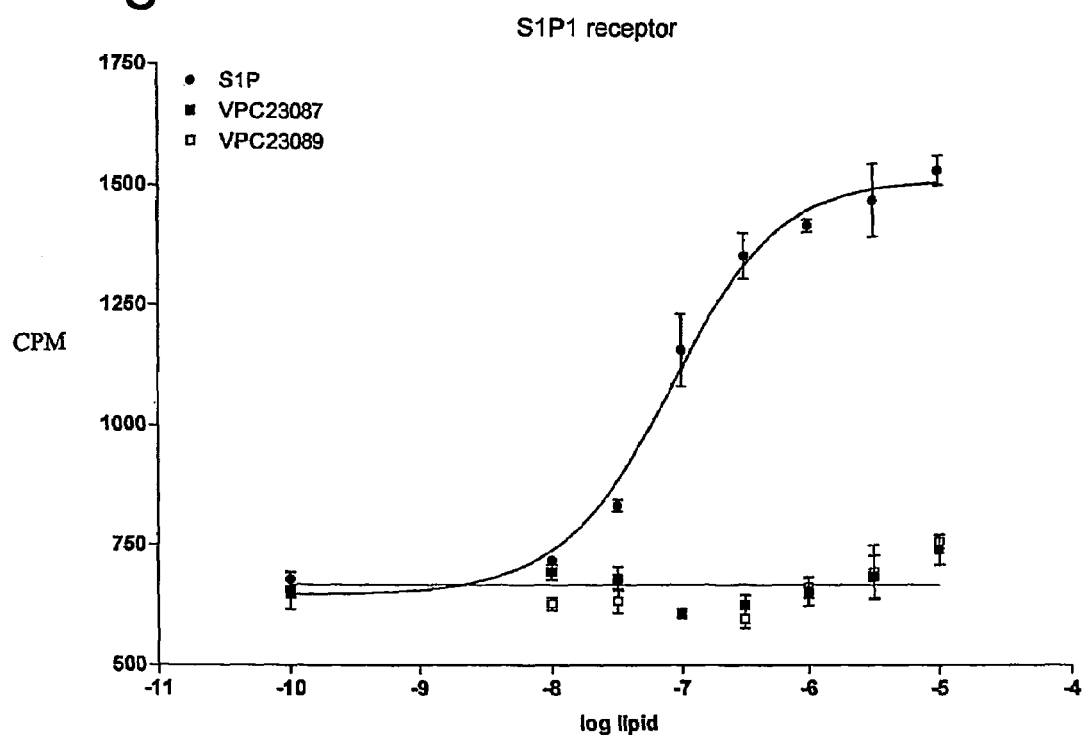
FIG. 4A-4E are graphic representations of [γ-$^{35}$S]GTP binding to HEK293T cell membranes (containing different S1P receptors) in response to S1P, VPC23087 and VPC23089.
Figure 4B:
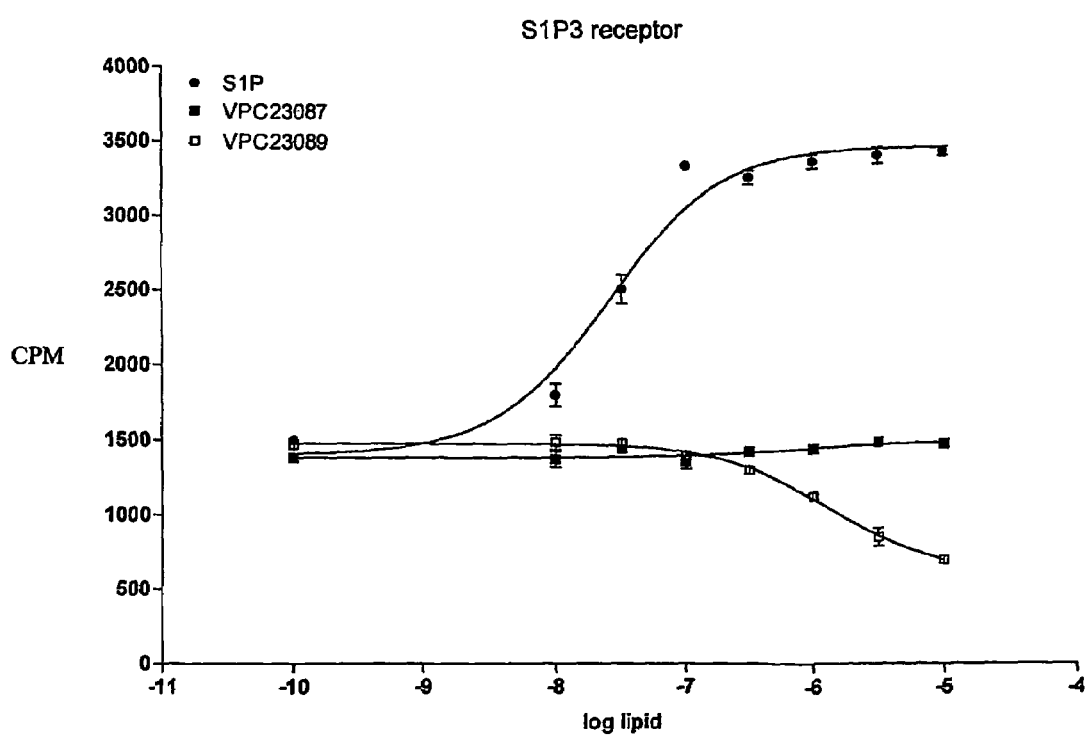
Figure 4C:
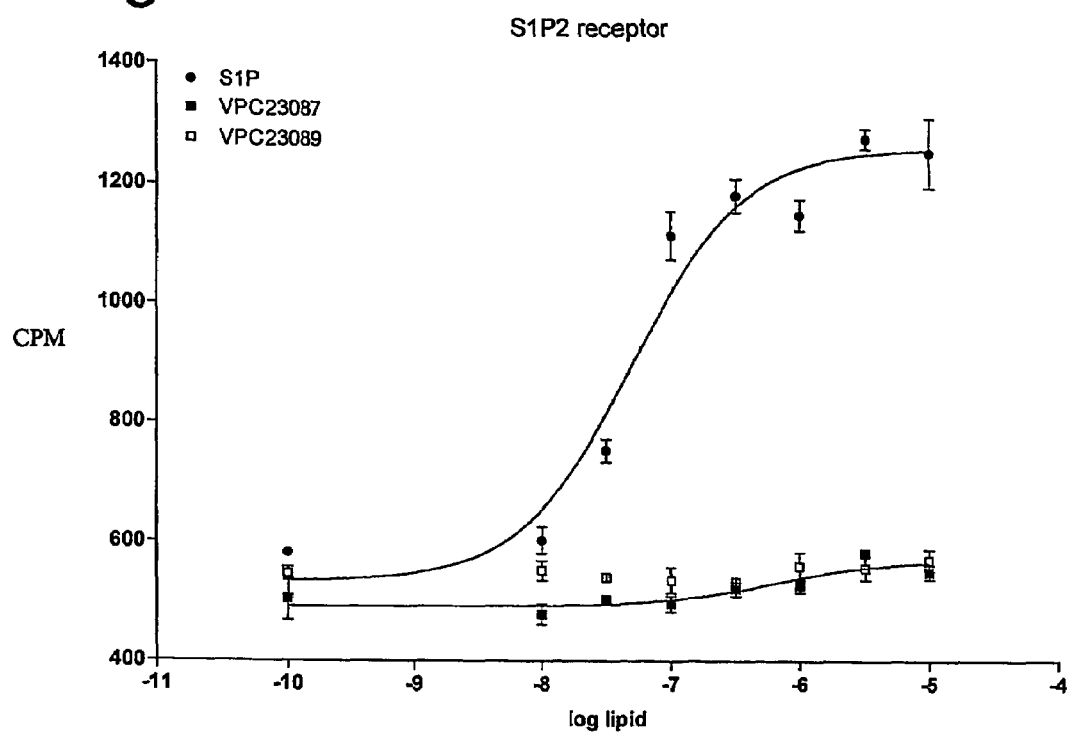
Figure 4D:
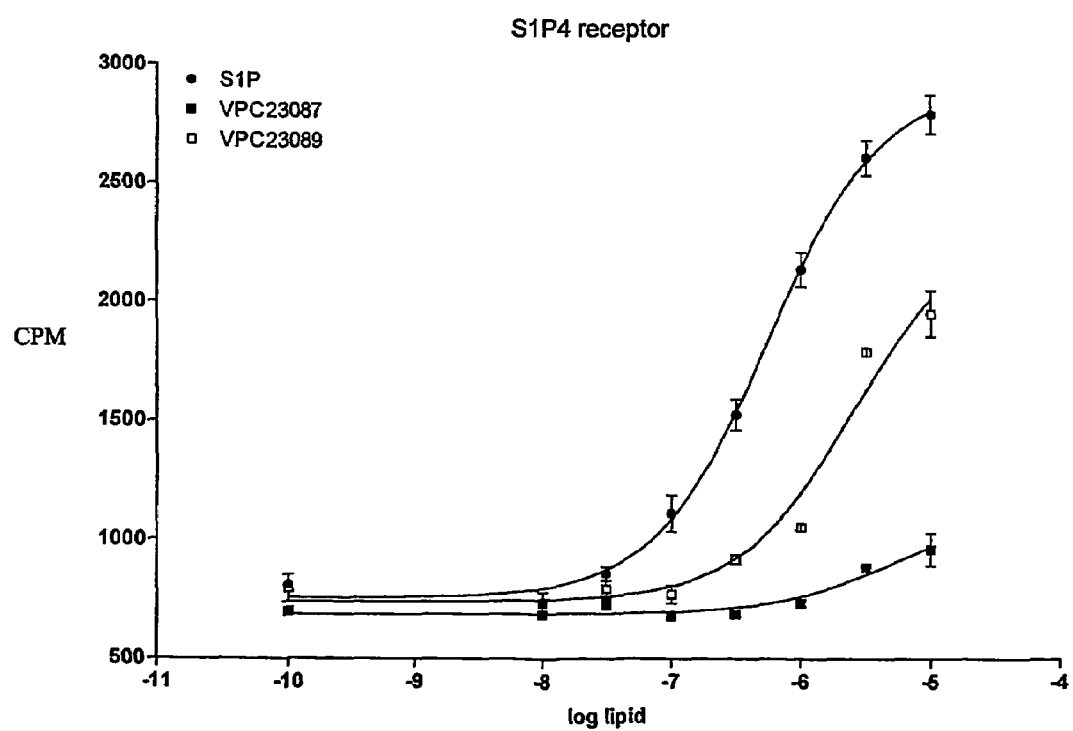
Figure 4E:
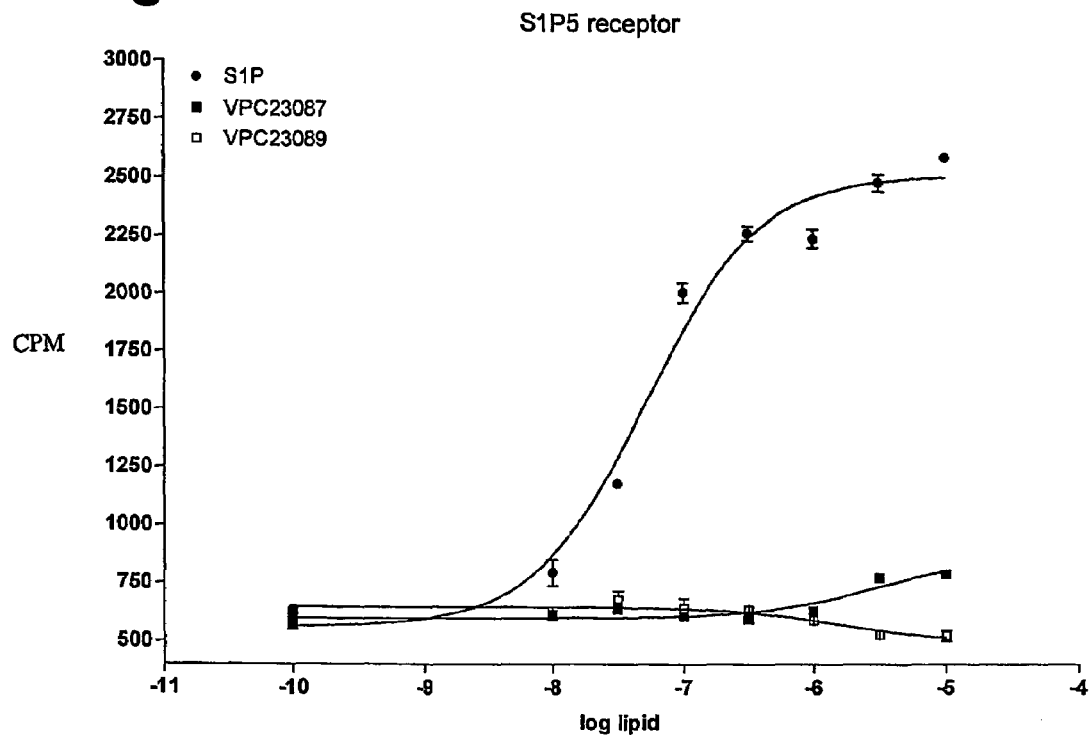

The GTP$_\gamma$S binding assay revealed that VPC23031, VPC23019, VPC23089 are inverse agonists (antagonists) of the S1P3 receptor (See FIGS. 1A and 4A), but this inverse agonism becomes agonism when the alkyl chain length is 9 carbons (VPC23079) or 10 (VPC23069), see FIGS. 2A and 3A.

Figure 5A:
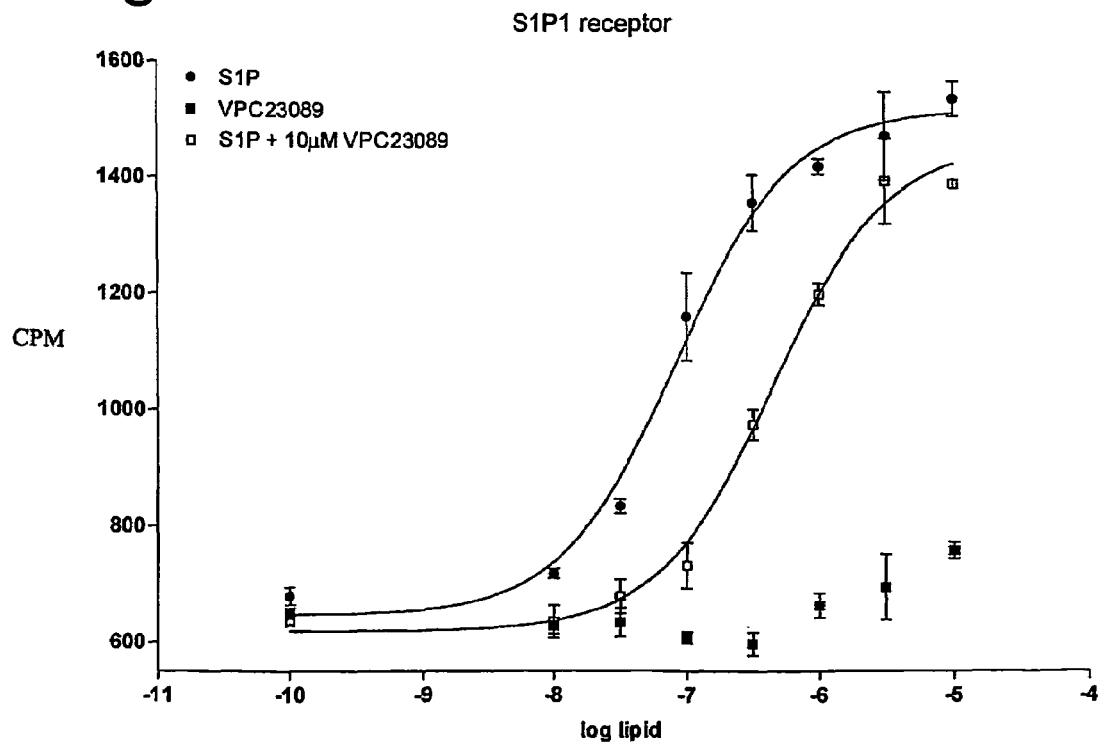
FIGS. 5A and 5B.
Figure 5B:
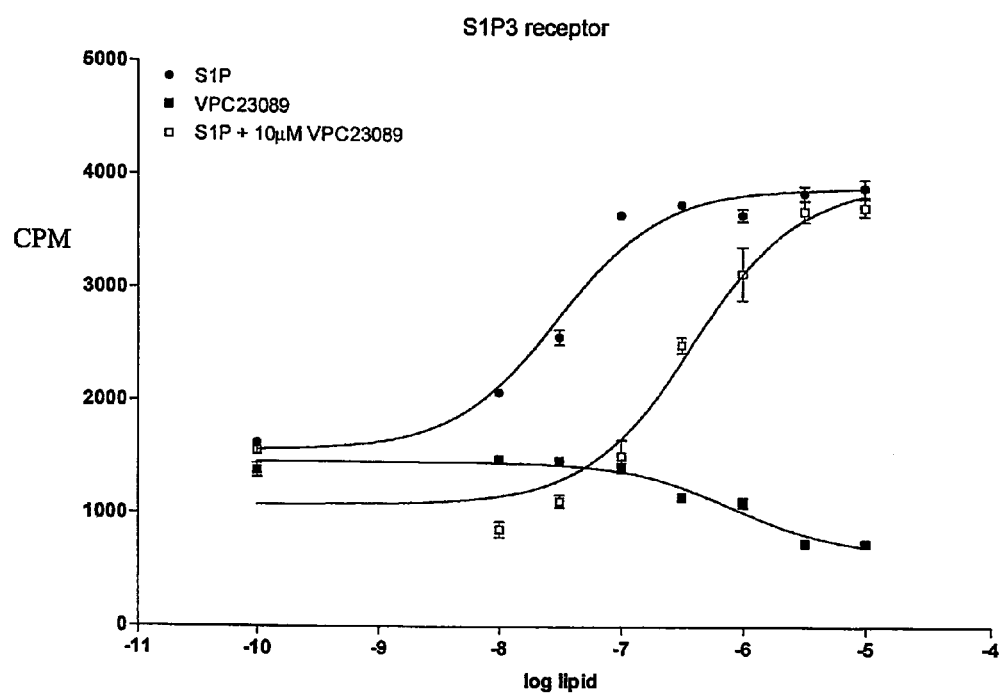
Figure 6A:
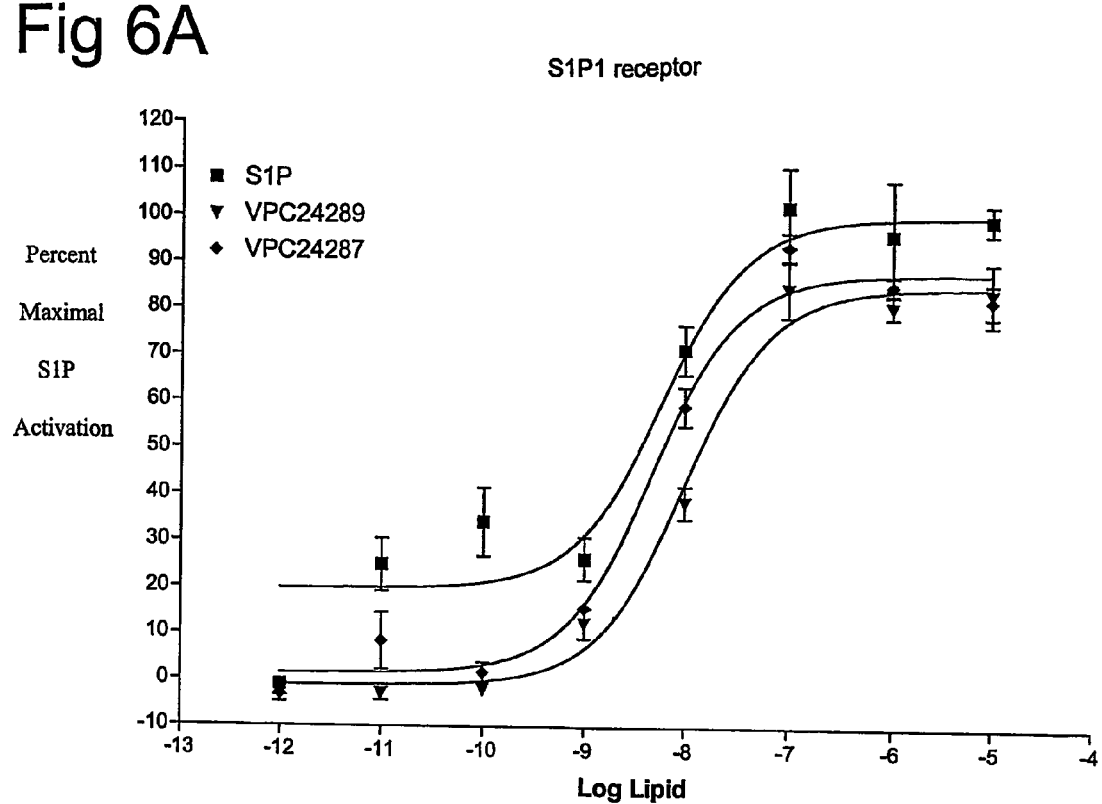
FIGS. 6A-6D are graphic representations of [γ-$^{35}$S]GTP binding to HEK293T cell membranes (containing different S1P receptors) in response to S1P, VPC24289 and VPC24287.
Figure 6B:
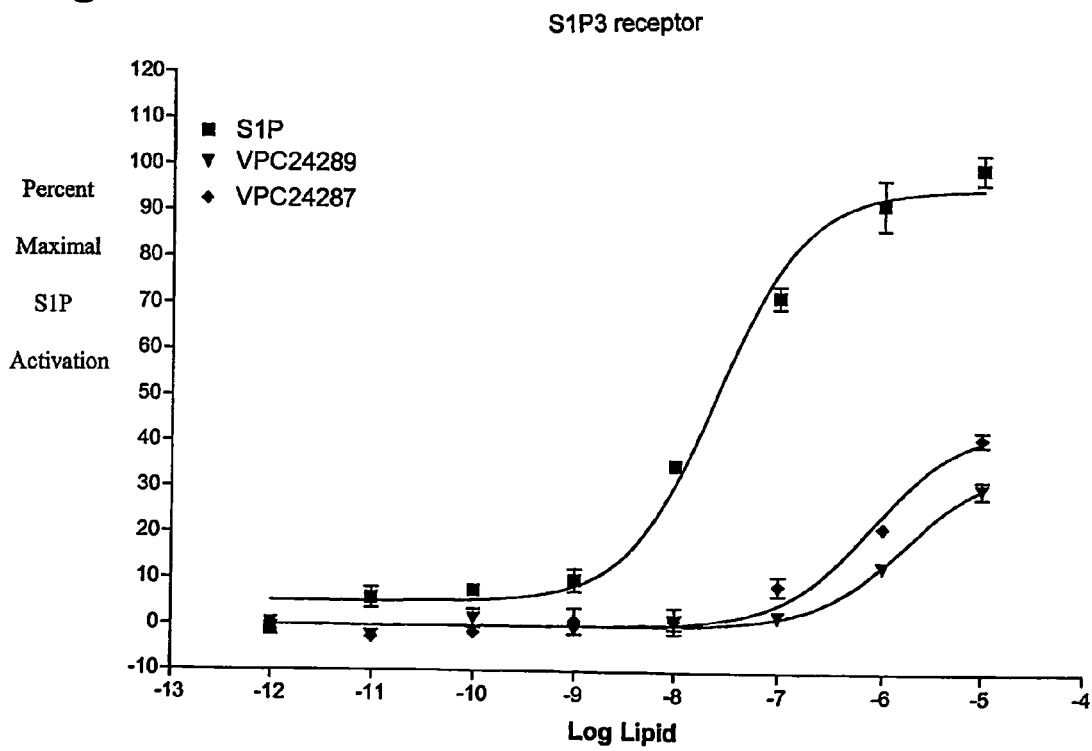
Figure 6C:
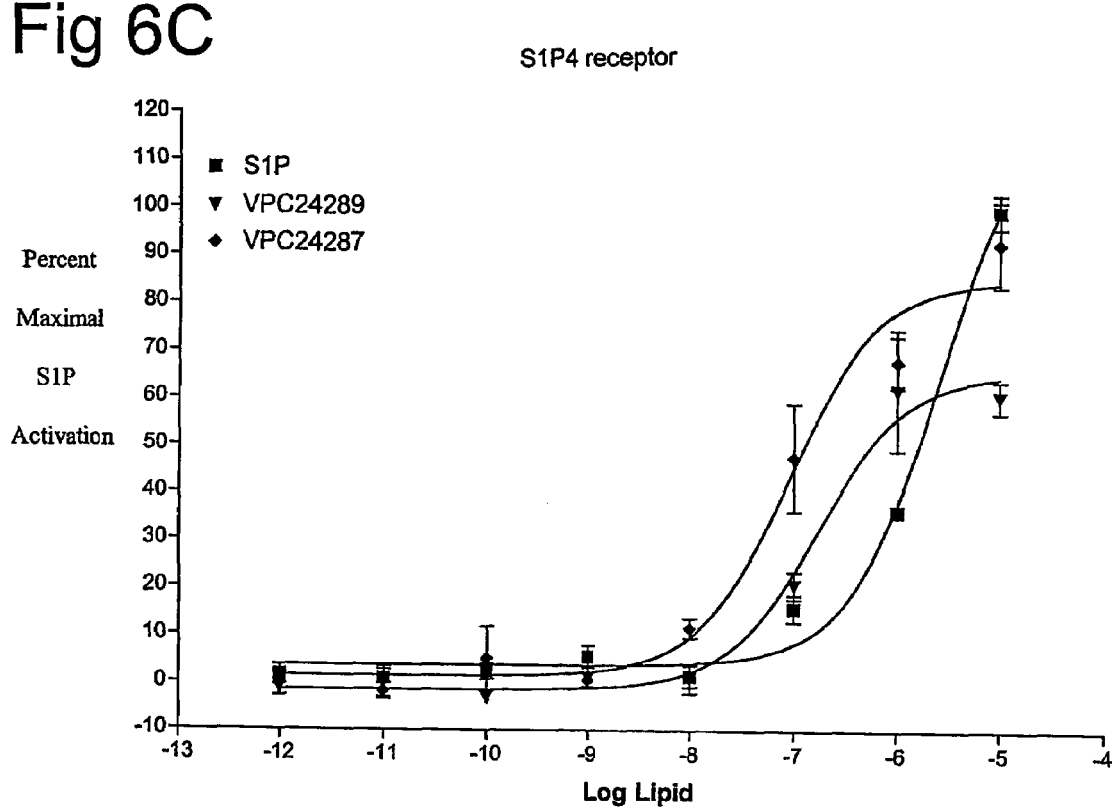
Figure 6D:
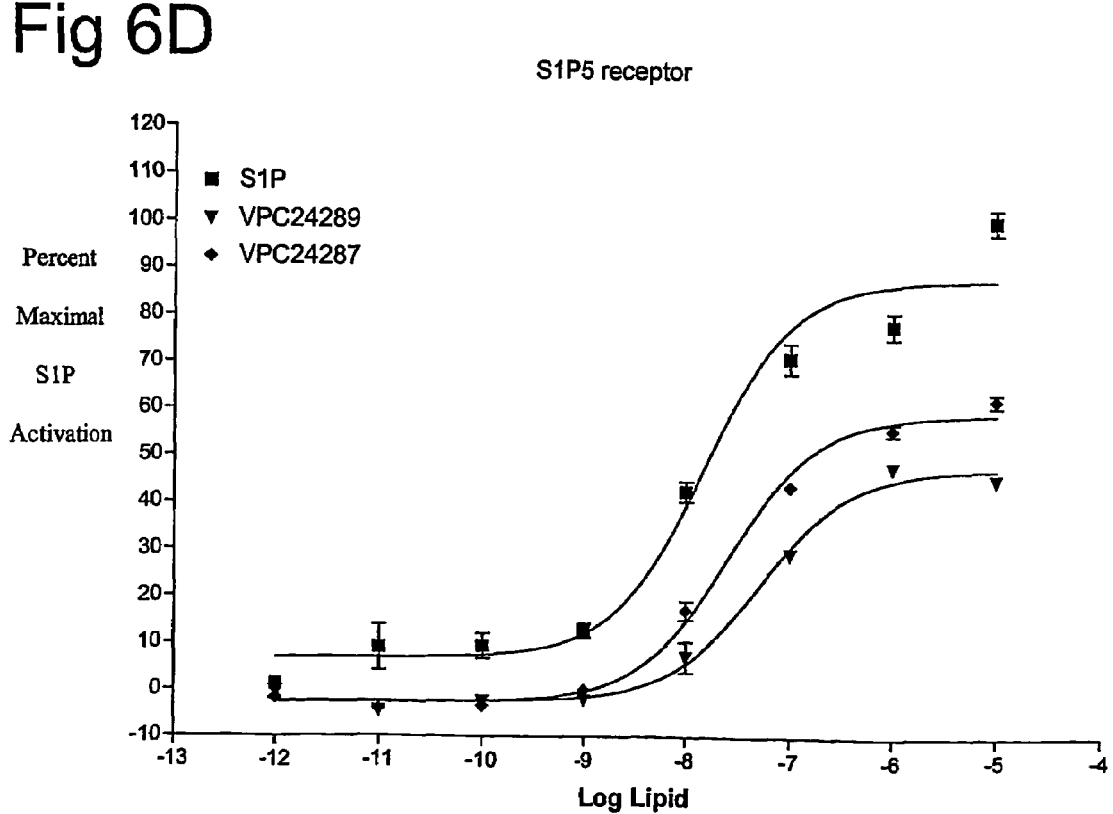

VPC23089 and VPC23019 are isomers, with the VPC23089 compound having the alkyl chain ortho and the VPC23019 compound meta; in both cases the alkyl chain has 8 carbons, but surprisingly, when one goes from ortho to meta, antagonism at S1P1 is realized (compare FIG. 1A with the competition curve FIG. 5A).

Example 6

Preparation of Esters of the Invention

Schemes for preparation of two types of esters, or compounds to be esterified, of the invention are provided. The structures are A and B:

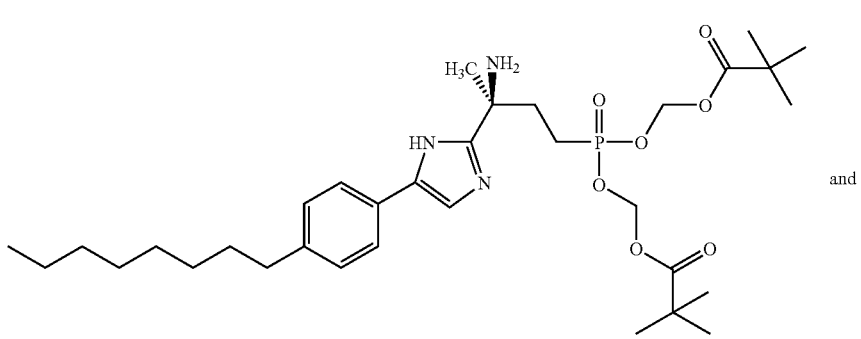

and

A

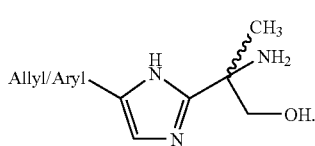 

B

The synthesis of A begins with the construction of three intermediates. Tetrabenzyl methylenediphosphonate 1 is derived from its commercially available tetrachloro-precursor and benzyl alcohol under basic conditions with catalytic tetrazole (Stepinski, D. C. Nelson, D. W. Zalupsid, P. R. Herlinger, A. W. *Tetrahedron* 2001, 57, 8637-8645). Many efforts are reported to synthesize α-methyl serine synthons (Avenoza, A. Cativiela, C. Corzana, F. Peregrina, J. M. Sucunza, D. Zurbano, M. M. *Tetrahedron Asymmetry* 2001, 12, 949-957 and references therein). However, with α-methyl serine, in hand, an extended exposure to benzyl chloroformate, Cbz-Cl, under Schotten-Baumen conditions results in nearly quantitative conversion to the desired compound, 2. Numerous α-bromo aryl ketones, such as compound 3, have been prepared successfully under neat conditions of aluminum chloride and bromoacetyl bromide.

The carboxylic acid moiety of 2 is converted to a practical nucleophile with $Cs_2CO_3$ in ethanol. Following evaporation and reconstitution in DMF, the activated carboxylate is then coupled with 3 to form 2-acyloxy ester 4. The subsequent Davidson cyclization ($NH_4OAc$ at 110° C. in xylenes while affixed to a dean-stark trap) is obtained in higher yields if 4 is isolated by chromatography, but may be performed crude to yield the 4-phenyl-imidazole 5. The primary alcohol of 5 is oxidized under standard Swern conditions and reacted with the stabilized yield of 1 in a Horner-Wadsworth-Emmons reaction. The resulting double bond, Cbz group and dibenzyl phosphonate are easily hydrogenated under an atmosphere (balloon) of $H_2$ over 10% Pd on C. The imidazole and amine are concomitantly protected with 9-fluorenylmethyl chloroformate, Fmoc-Cl to yield 6. Phosphonic acid 6 is esterified under basic conditions in acetonitrile (Ortmann, R. Wiesner, J. Reichenberg, A. Henschker, D. Beck, E. Jomaa, H. Schlitzer, M. *Bioorg. Med. Chem. Lett.* 2003, 13, 2163-2166) (shown is the acid labile pivaloyloxy methyl ester), and finally deprotected with piperidine to yield final compound A:

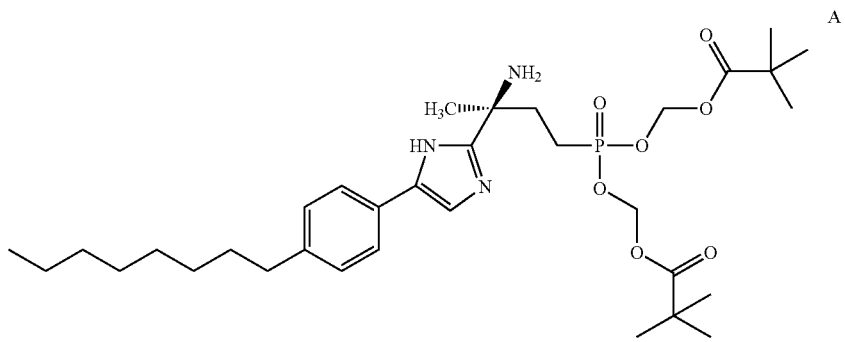

A

A scheme for the preparation of structure A is:
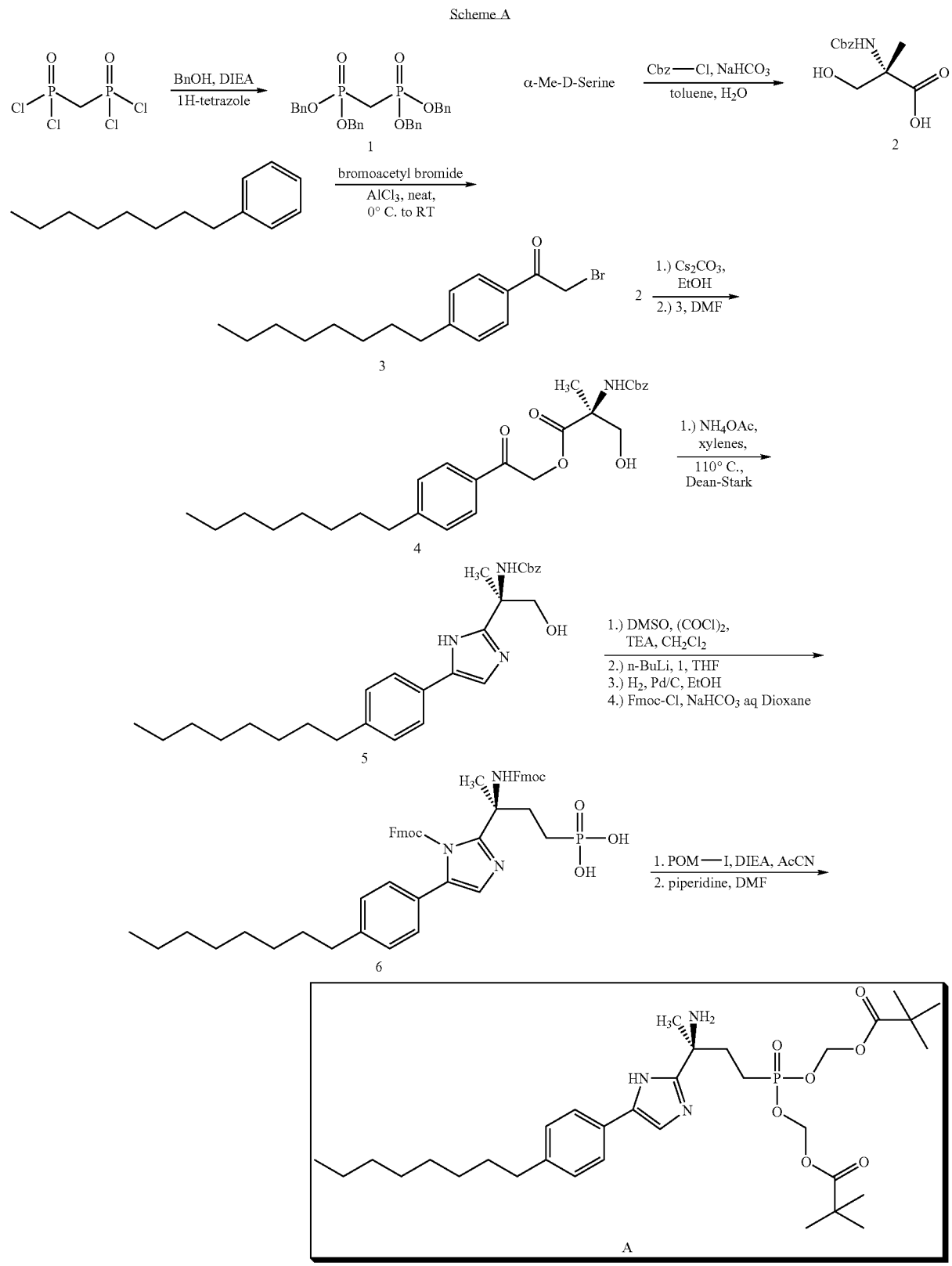

Molecules with the general structure of compound B can be derived from a series of aryl-lithiations to commercially available 1-benzyl imidazole. The first lithiation takes place at the two position and may be quenched with tri-isopropyl borate to give boronate 1 (Fujita, K. Hikichi, S. Akita, M. Moro, Y. *J. Chem. Soc. Dalton Trans.* 2000, 8, 1255-1260). Aryl boronates undergo conversion to chiral aryl amino acids by conditions described by Petasis as a variant of the Mannich reaction (Petasis, N. A. Zavialov, I. A. *J. Am. Chem. Soc.* 1997, 119, 445-446). The formation of 2 specifically takes place with the addition of commercially available (S) or (R)-2-phenylglycinol and pyruvic acid in toluene followed by the hydrogenolysis of the protected amines in the presence of di-tert-butyl dicarbonate. A second lithiation of imidazole 2 allows for iodination taking place at the five position (Iddon, B. Lim, B. L. *J. Chem. Soc. Perkin Trans.* 1 1983, 271-277), producing intermediate 3. This intermediate is now available for treatment with various aryl or allyl boronic acids under Suzuki conditions (Deveau, A. M. Macdonald T. L. *Tetrahedron Lett.* 2004, 803-807 and references therein). Finally, trifluoroacetic acid catalyzed deprotection gives compounds with the structure of B:

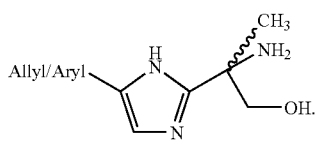

A scheme for the preparation of structure B is:

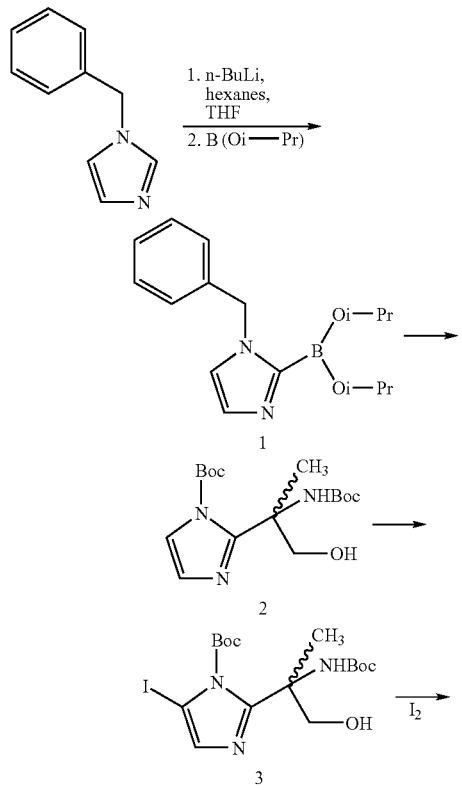

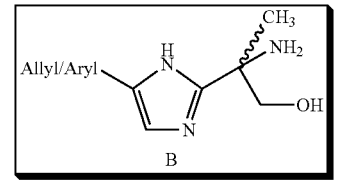

Structure 3 and structure B, as described in the scheme used to synthesize B, can then be subjected to the reactions utilized in the final two steps of the scheme used to prepare structure A above, to obtain the appropriate ester of structure 3 and structure B.

The disclosures of each and every publication cited herein are hereby incorporated herein by reference in their entirety.

Other methods which were used but not described herein are well known and within the competence of one of ordinary skill in the art of clinical, chemical, cellular, histochemical, biochemical, molecular biology, microbiology and recombinant DNA techniques. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound of the formula:

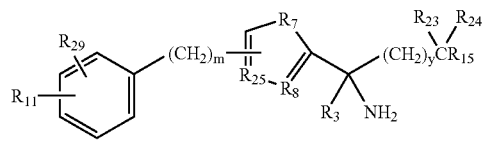

wherein $R_{11}$ is $C_5$-$C_{18}$ alkyl, $C_5$-$C_{18}$ alkenyl, $C_5$-$C_{18}$ alkynyl, $C_5$-$C_{18}$ alkoxy, $C_1$-$C_{10}$ alkyl($C_5$-$C_6$ aryl)$R_{20}$, $C_1$-$C_{10}$ alkyl($C_5$-$C_6$ heteroaryl)$R_{20}$, $C_1$-$C_{10}$ alkyl($C_5$-$C_6$ cycloalkyl)$R_{20}$, $C_1$-$C_{10}$ alkoxy($C_5$-$C_6$ aryl)$R_{20}$, $C_1$-$C_{10}$ alkoxy($C_5$-$C_6$ heteroaryl)$R_{20}$ or $C_1$-$C_{10}$ alkoxy($C_5$-$C_6$ cycloalkyl)$R_{20}$;

wherein $R_{20}$ is H or $C_1$-$C_{10}$ alkyl;

$R_{29}$ is H, halo, $C_1$-$C_{12}$ alkyl, $C_2$-$C_{12}$ alkenyl, $C_2$-$C_{12}$ alkynyl, or $C_1$-$C_{12}$ alkoxy;

$R_7$ is O, S, or $NR_{26}$;

$R_8$ is O, S, or $NR_{26}$;

wherein $R_{26}$ is H, F or $C_1$-$C_4$ alkyl;

$R_{25}$ is CH;

$R_3$ is hydrogen, $C_1$-$C_4$ alkyl, ($C_1$-$C_4$ alkyl)OH, or ($C_1$-$C_4$ alkyl)$NH_2$;

$R_{15}$ is

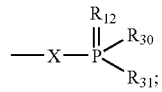

wherein $R_{12}$ is O or S;

X is O, S, $CH_2$, CHOH, CHF, $CF_2$, or

$R_{30}$ and $R_{31}$ are each independently $C_1$-$C_2$ alkoxy,

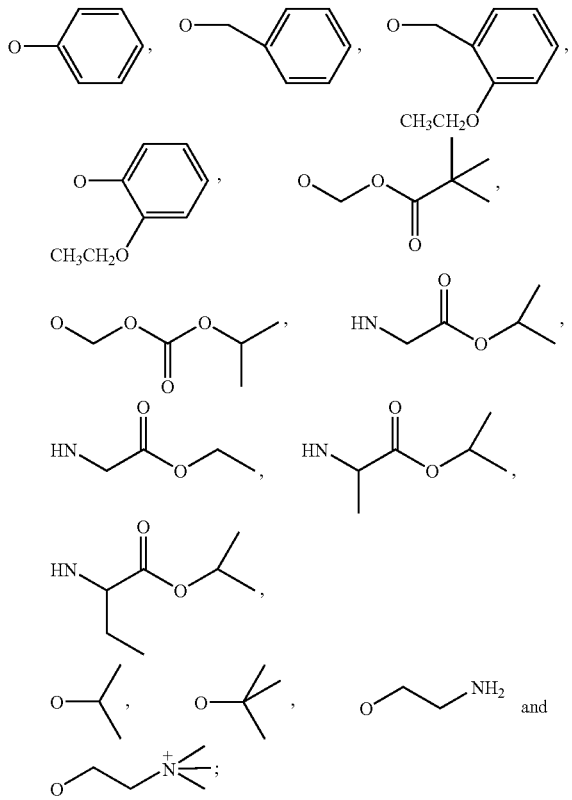

$R_{23}$ is H, F, OH, $C_1$-$C_4$ alkyl, $CO_2H$ or ($C_1$-$C_4$ alkyl)OH;
$R_{24}$ is H, F, $C_1$-$C_4$ alkyl or $PO_3H_2$; or
$R_{23}$ together with $R_{24}$ and the carbon to which they are attached form a carbonyl group; and
y and m are integers independently ranging from 0 to 4; or
a pharmaceutically acceptable salt or tautomer thereof.

2. The compound of claim 1 wherein
m is 0;
y is 0 or 1;
$R_{23}$ and $R_{24}$ are independently H or F.

3. The compound of claim 1 wherein $R_3$ is $C_1$-$C_3$ alkyl or ($C_1$-$C_4$ alkyl)OH; and
$R_8$ is N.

4. The compound of claim 2 wherein
$R_{11}$ is $C_5$-$C_{18}$ alkyl, $C_5$-$C_{18}$ alkenyl, $C_5$-$C_{18}$ alkynyl, or $C_5$-$C_{18}$ alkoxy and
$R_{29}$ is H, halo or $C_1$-$C_{12}$ alkyl; or
a pharmaceutically acceptable salt or tautomer thereof.

5. The compound of claim 2 wherein
y is 0; and
$R_{15}$ is represented by the structure

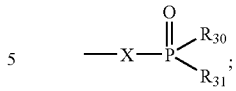

wherein X is $CH_2$, CHOH, CHF, $CF_2$, or

6. The compound of claim 1 of the formula:

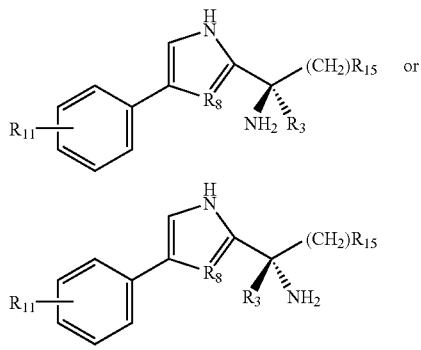

wherein $R_{11}$ is $C_5$-$C_{18}$ alkyl or $C_5$-$C_{18}$ alkenyl; and
$R_8$ is N, or S;
or a pharmaceutically acceptable salt or tautomer thereof.

7. The compound of claim 6 wherein $R_{11}$ is $C_5$-$C_9$ alkyl; $R_{15}$ is

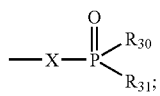

wherein X is O, $CH_2$ or CHF;
$R_{30}$ and $R_{31}$ are independently

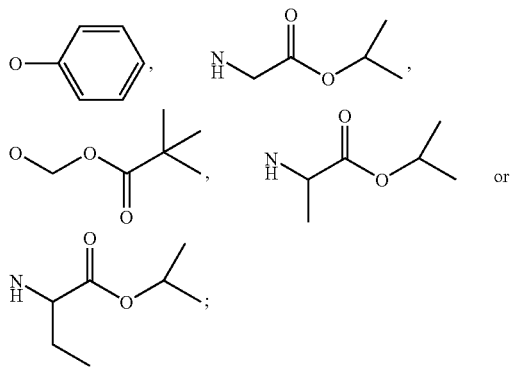

and $R_3$ is $CH_3$.

8. The compound of claim 1 of the formula

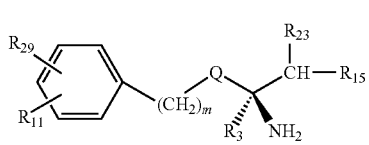

wherein $R_{11}$ is $C_5$-$C_{18}$ alkyl, $C_5$-$C_{18}$ alkenyl, $C_5$-$C_{18}$ alkynyl, or $C_5$-$C_{18}$ alkoxy;

$R_{15}$ is

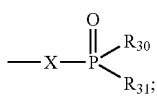

wherein X is O, $CH_2$, CHOH, CHF, $CF_2$, or

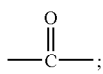

$R_{30}$ and $R_{31}$ are independently $C_1$-$C_2$ alkoxy,

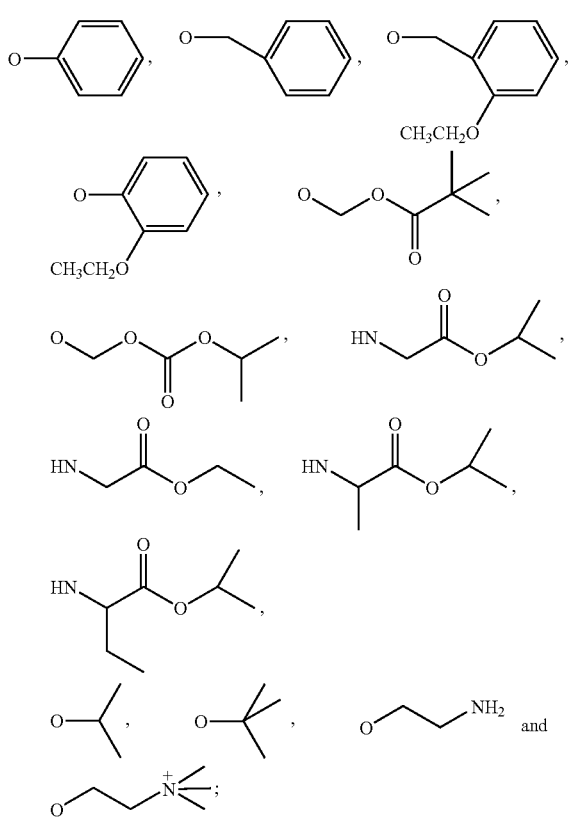

wherein
$R_{29}$ is H, $C_1$-$C_{10}$ alkyl, $C_2$-$C_{10}$ alkenyl or $C_2$-$C_{10}$ alkynyl;
Q is

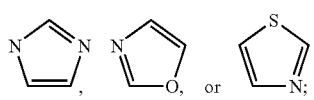

m is 0; and
$R_{23}$ is H or F.

9. The compound of claim 8 of the formula:

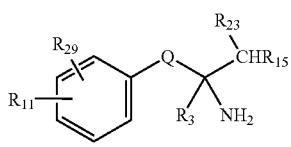

$R_{12}$ is O; and X is O, $CH_2$, CHOH, CHF, $CF_2$, and

10. The compound of claim 8 of the formula:

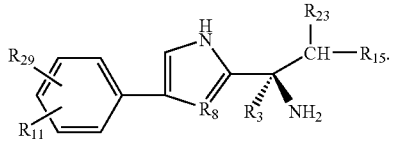

11. The compound of claim 10 wherein $R_3$ is $C_1$-$C_4$ alkyl or ($C_1$-$C_4$ alkyl)OH;
$R_8$ is O, S, or N;
$R_{23}$ is H or F; and
$R_{15}$ is represented by the structure

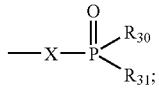

wherein X is O, $CH_2$, CHOH, CHF, $CF_2$ or

12. The compound of claim 11 wherein X is O, $CH_2$, CHF or $CF_2$.

13. The compound of claim 12 wherein X is O.

14. The compound of claim 12 wherein X is $CH_2$, CHF or $CF_2$.

15. The compound of claim 12 wherein $R_{30}$ and $R_{31}$ are the same and are

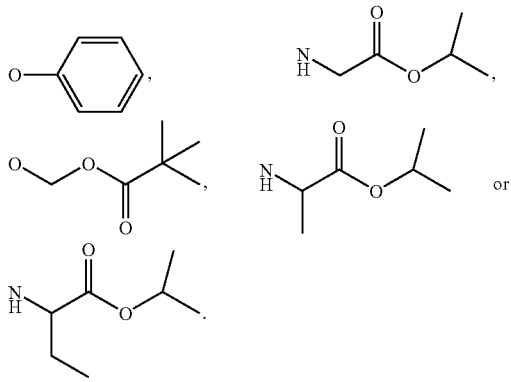

16. The compound of claim 14 wherein $R_8$ is N.
17. The compound of claim 14 of the formula:

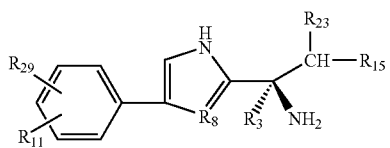

wherein $R_{11}$ is H, $C_5$-$C_{18}$ alkyl, $C_5$-$C_{18}$ alkenyl, $C_5$-$C_{18}$ alkynyl, or $C_5$-$C_{18}$ alkoxy;
$R_3$ is $CH_3$; and
$R_{29}$ is H, $C_1$-$C_4$ alkyl.
18. The compound of claim 17 wherein $R_{11}$ is $C_5$-$C_{18}$ alkyl, or $C_5$-$C_{18}$ alkenyl; and $R_{29}$ H, or $C_1$-$C_4$ alkyl.
19. The compound of claim 17 wherein $R_{11}$ is $C_5$-$C_{18}$ alkyl or alkenyl; and $R_{29}$ is H.
20. A pharmaceutical composition comprising a compound of the formula:

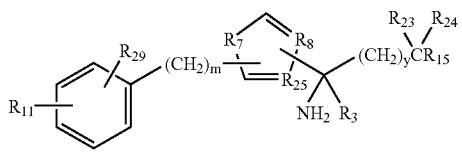

wherein
$R_{11}$ is $C_5$-$C_{18}$ alkyl, $C_5$-$C_{18}$ alkenyl, $C_5$-$C_{18}$ alkynyl, $C_5$-$C_{18}$ alkoxy, $C_1$-$C_{10}$ alkyl($C_5$-$C_{10}$ aryl)$R_{20}$, $C_1$-$C_{10}$ alkyl($C_5$-$C_{10}$ heteroaryl)$R_{20}$, $C_1$-$C_{10}$ alkyl($C_5$-$C_{10}$ cycloalkyl)$R_{20}$, $C_1$-$C_{10}$ alkoxy($C_5$-$C_{10}$ aryl)$R_{20}$, $C_1$-$C_{10}$ alkoxy($C_5$-$C_{10}$ heteroaryl)$R_{20}$ or $C_1$-$C_{10}$ alkoxy($C_5$-$C_{10}$ cycloalkyl)$R_{20}$;
wherein $R_{20}$ is H or $C_1$-$C_{10}$ alkyl;
$R_{29}$ is H, halo, $C_1$-$C_{12}$ alkyl, $C_2$-$C_{12}$ alkenyl, $C_2$-$C_{12}$ alkynyl, or $C_1$-$C_{12}$ alkoxy;
$R_3$ is H, $C_1$-$C_6$ alkyl, ($C_1$-$C_4$ alkyl)OH, or ($C_1$-$C_4$ alkyl)$NH_2$;
$R_{23}$ is H, F, $CO_2H$, OH, $C_1$-$C_4$alkyl, or ($C_1$-$C_4$ alkyl)OH;
$R_{24}$ is H, F, $C_1$-$C_4$alkyl or $PO_3H_2$; or
$R_{23}$ together with $R_{24}$ and the carbon to which they are attached form a carbonyl group;
$R_7$ is O, S, or $NR_{26}$;
$R_8$ is O, S, or $NR_{26}$;
wherein $R_{26}$ is H, F or $C_1$-$C_4$ alkyl;
$R_{25}$ is CH;
wherein $R_{26}$ is H, F or $C_1$-$C_4$ alkyl;
$R_{15}$ is

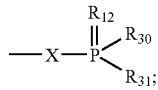

wherein $R_{12}$ is O or S;
X is O, NH, S, $CH_2$, CHOH, CHF, $CF_2$, or

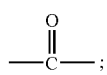

and
each $R_{30}$ is independently and each $R_{31}$ is independently $C_1$-$C_2$ alkoxy,

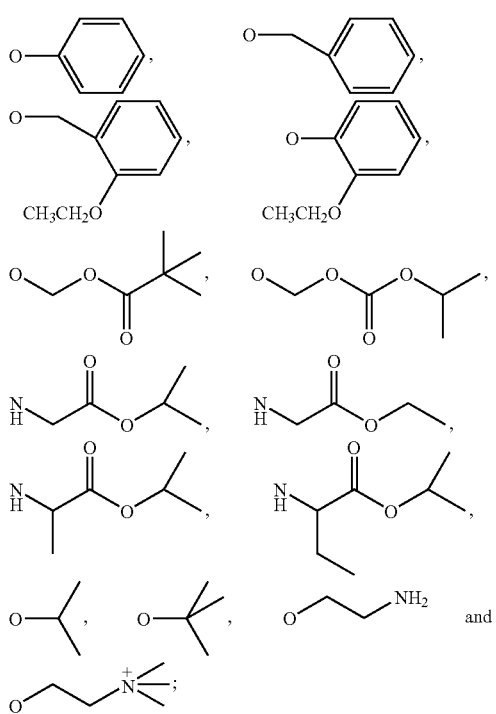

y and m are integers independently ranging from 0 to 4;
a pharmaceutically acceptable salt or tautomer thereof;
and a pharmaceutically acceptable carrier.
21. The composition of claim 20 comprising a compound of the formula:

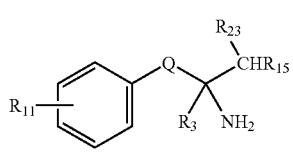

wherein $R_{11}$ is $C_5$-$C_{18}$ alkyl, $C_5$-$C_{18}$ alkenyl, $C_5$-$C_{18}$ alkynyl, or $C_5$-$C_{18}$ alkoxy;
wherein
Q is

wherein $R_7$ is O, S, or $NR_{26}$;
$R_8$ is O, S, or $NR_{26}$;
wherein $R_{26}$ is H, F or $C_1$-$C_4$ alkyl;
$R_{25}$ is CH; and
$R_3$ is H, $C_1$-$C_4$ alkyl or ($C_1$-$C_4$ alkyl)OH;
$R_{23}$ is H, F or $C_1$-$C_4$ alkyl; and
$R_{15}$ is represented by the structure

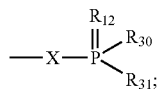

wherein $R_{12}$ is O or S;
X is O, S, $CH_2$, CHOH, CHF, $CF_2$, or

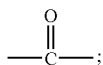

$R_{30}$ and $R_{31}$ are independently $C_1$-$C_2$ alkoxy,

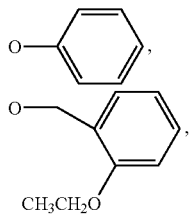 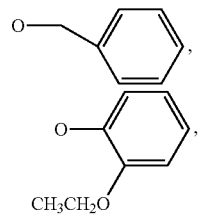

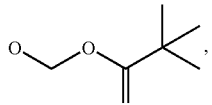 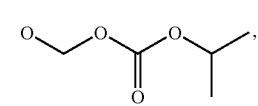

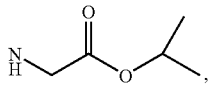 

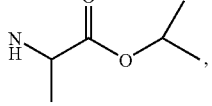 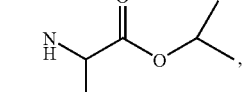

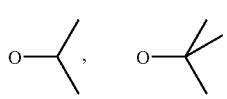 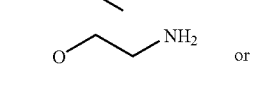 or

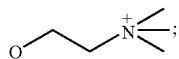

or a pharmaceutically acceptable salt or tautomer thereof; and
a pharmaceutically acceptable carrier.

22. The composition of claim 21 wherein $R_{23}$ is H or F; and $R_{15}$ is

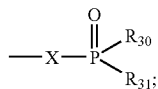

wherein X is O, $CH_2$, CHOH, CHF, $CF_2$, or

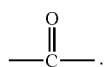

23. The composition of claim 22 wherein Q is

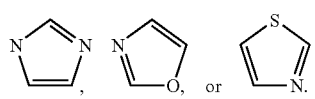

24. The composition of claim 23 wherein
X is $CH_2$, $CF_2$ or CHF; and
$R_{30}$ and $R_{31}$ are independently $C_1$-$C_2$ alkoxy,

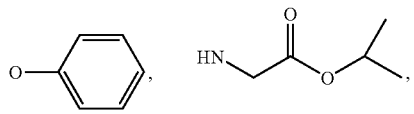

 or

25. The composition of claim 24 wherein Q is

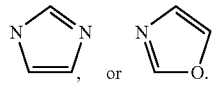

* * * * *

UNITED STATES PATENT AND TRADEMARK OFFICE
CERTIFICATE OF CORRECTION

PATENT NO. : 7,638,637 B2 Page 1 of 1
APPLICATION NO. : 10/578216
DATED : December 29, 2009
INVENTOR(S) : Lynch et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 291 days.

Signed and Sealed this

Ninth Day of November, 2010

David J. Kappos
*Director of the United States Patent and Trademark Office*